US012311016B2

(12) United States Patent
Lustigman et al.

(10) Patent No.: US 12,311,016 B2
(45) Date of Patent: May 27, 2025

(54) BIOMARKERS AND IMMUNOGENIC COMPOSITIONS FOR FILARIAL PARASITES

(71) Applicants: New York Blood Center, Inc., New York, NY (US); The United States of America, as Represented by the Secretary, Department of Health and Human Services, Rockville, MD (US)

(72) Inventors: Sara Lustigman, New York, NY (US); Thomas B. Nutman, Bethesda, MD (US); Sasisekhar Bennuru, Bethesda, MD (US)

(73) Assignees: New York Blood Center, Inc., New York, NY (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/173,288

(22) Filed: Feb. 23, 2023

(65) Prior Publication Data

US 2023/0414731 A1 Dec. 28, 2023

Related U.S. Application Data

(62) Division of application No. 17/076,616, filed on Oct. 21, 2020, which is a division of application No. 16/090,013, filed as application No. PCT/US2017/025554 on Mar. 31, 2017, now abandoned.

(60) Provisional application No. 62/317,243, filed on Apr. 1, 2016.

(51) Int. Cl.

| | |
|---|---|
| ***A61K 39/00*** | (2006.01) |
| ***A61P 33/10*** | (2006.01) |
| ***C07K 14/435*** | (2006.01) |
| ***C07K 16/18*** | (2006.01) |
| ***G01N 33/53*** | (2006.01) |

(52) U.S. Cl.

CPC .......... *A61K 39/0003* (2013.01); *A61P 33/10* (2018.01); *C07K 14/4354* (2013.01); *C07K 16/18* (2013.01); *G01N 33/5308* (2013.01); *A61K 2039/552* (2013.01); *A61K 2039/55505* (2013.01); *A61K 2039/6031* (2013.01); *A61K 2039/70* (2013.01)

(58) Field of Classification Search

CPC .......... A61K 39/0003; A61K 2039/552; A61K 2039/55505; A61K 2309/6031; A61K 2039/70; A61P 33/10; C07K 14/4354; C07K 16/18; G01N 33/5308

See application file for complete search history.

(56) References Cited

U.S. PATENT DOCUMENTS

| | | | |
|---|---|---|---|
| 5,021,342 | A | 6/1991 | Greene et al. |
| 2006/0039921 | A1 | 2/2006 | MacDonald et al. |

FOREIGN PATENT DOCUMENTS

| | | | |
|---|---|---|---|
| WO | 2015/121646 | A1 | 8/2015 |

OTHER PUBLICATIONS

Bennuru et al. "Stage-specific transcriptome and proteome analyses of the filarial parasite *Onchocerca volvulus* and its Wolbachia endosymbiont," mBio 7:1-11, 2016.

Cotton et al. "The genome of Onchocerca volvulus, agent of river blindness," Nature Microbiology 2:1-12, 2016.

Cotton et al. "Genome sequencing of Onchocerca volvulus," UniProt Proteome ID: UP000024404; https://www.uniprot.org/proteomes/UP000024404.

Taylor et al. "Protective immunity induced by vaccination with Onchocerca volvulus tropomysin in rodents," Parasite Immunology 18:219,225, 1996.

Arumugam et al. "Vaccination with recombinant Brugia malayi cystatin proteins alters worm migration, homing and final niche selection following a subcutaneous challenge of Mongolian gerbils (*Meriones unguiculatus*) with B. malayi infective larvae," Parasites & Vectors 7:43-49, 2014.

Arumugam et al. "Vaccination with genetically modified Brugia malayi cysteine protease inhibitor 2 reduces adult parasite numbers and affects the fertility of female worms following a subcutaneous challenge of Mongolian gerbils (*Meriones unguiculatus*) with B. malayi infective larvae," Int J Parasitology 44:675-679, 2014.

Hess et al. "Vaccines to combat river blindness: expression, selection and formulation of vaccines against infection with Onchocerca volvulus in mouse model," 44637-646, 2014.

Hess et al. The immunomodulatory role of adjuvants in vaccines formulated with the recombinant antigens Ov-103 and Ov-RAL-2 against Onchocerca volvulus in mice. PLoS Negl Trop Dis 10(7):e0004797, 2016.

Arumugam et al. "Vaccination of gerbils with Bm-103 and Bm-RAL-2 concurrently or as a fusion protein confers consistent and improved protection against Brugia malayi infection." PLoS Negl Trop Dis 4(10):e0004586, 2016.

Benneru S et al. "Metabolite profiling of infection-associated metabolic markers of onchocerciasis" Mol Biochem Parasitol 215:58-69, 2017.

Benneru S "Understanding hidden antigens and targeting parasitic nematodes" EBioMedicine 2:1010-1011, 2015.

Bennuru S et al. "Mining filarial genomes for diagnostic and therapeutic targets" Trends Parasitol 34:80-90, 2018.

(Continued)

*Primary Examiner* — Robert A Zeman

(74) *Attorney, Agent, or Firm* — Fish & Richardson P.C.

(57) ABSTRACT

Disclosed herein are immunogenic compositions for preventing or treating infection with filarial parasites and biomarkers for diagnosing infection with filarial parasites.

6 Claims, 18 Drawing Sheets

Specification includes a Sequence Listing.

(56) References Cited

OTHER PUBLICATIONS

Patton JB et al. "Development of Onchocerca volvulus in humanized NSG mice and detection of parasite biomarkers in urine and serum" PLoS Negl Trop Dis 12:e0006977, 2018.
Skolnick, J et al. "From genes to protein structure and function: novel applications of computational approaches in the genomic era" TIBTECH 18:34-39, 2000.
International Search Report and Written Opinion PCT/US2017/025554 issued Jul. 5, 2017.
Boslego JW et al. "Gonorrhea vaccines" Vaccines and Immunotherapy, Chapter 17, 1991.
Ellis. Vaccines, W.b. Saunders Company, Chapter 29, pp. 568-574, 1988.
Tamashiro et al. American Journal of Tropical Medicine and Hygiene, 404:368-376, 1989.
Boatin Ba et al. "Control of onchocerciasis" Advances in Parasitology 61:349-394, 2006.
Boto et al., "Homologous and distinctive antigens of Onchocerca volvulus and Dirofilaria immitis: detection by an enzyme-linked immuno-inhibition assay," Journal of immunology, Aug. 1984, 133(2):981-7.
Cafarelli et al., "De novo genome sequencing and comparative stage-specific transcriptomic analysis of Dirofilaria repens," International journal for parasitology, Nov. 2019, 49(12):911-9.
George et al., "Antibody responses against the vaccine antigens Ov-103 and Ov-RAL-2 are associated with protective immunity to Onchocerca volvulus infection in both mice and humans," PLoS Neglected Tropical Diseases, Sep. 16, 2019, 13(9):e0007730, 23 pages.
International Preliminary Report on Patentability in International Appln. No. PCT/US2017/025554, mailed on Oct. 11, 2018, 6 pages.
Limberger et al., "Filarial paramyosin: cDNA sequences from Dirofilaria immitis and Onchocerca volvulus," Molecular and biochemical parasitology, Jan. 15, 1990, 38(2):271-80.
Mejia et al., "Expression of an Onchocerca volvulus Ov33 homolog in Dirofilaria immitis: potential in immunodiagnosis of heartworm infection," Parasite immunology, Jun. 1994, 16(6):297-303.
Needleman et al., "A general method applicable to the search for similarities in the amino acid sequence of two proteins," Journal of molecular biology, Mar. 28, 1970, 48(3):443-53.

BIOMARKERS AND IMMUNOGENIC COMPOSITIONS FOR FILARIAL PARASITES

CROSS REFERENCE TO RELATED APPLICATIONS

The present application is a division of U.S. patent application Ser. No. 17/076,616, filed Oct. 21, 2020, which is a division of U.S. patent application Ser. No. 16/090,013 filed Sep. 28, 2018, which is a 35 U.S.C. § 371 national phase entry of PCT/US2017/025554, filed Mar. 31, 2017, which claims the benefit of U.S. Provisional Patent Application 62/317,243 filed Apr. 1, 2016, the entire contents of all of which are incorporated by reference herein.

SEQUENCE LISTING

A Sequence Listing is submitted herewith and incorporated by reference herein as an XML file created on Jun. 26, 2023, entitled "1958427-00357_Sequence_Listing.xml" and having a size of 71 KB.

STATEMENT REGARDING FEDERALLY SPONSORED RESEARCH

This invention was made in part with government support under Grant/Contract Number AI42328 awarded by the Division of Microbiology and Infectious Diseases, National Institute of Allergy and Infectious Diseases, National Institutes of Health; the Division of Intramural Research (DIR) of the National Institute of Allergy and Infectious Diseases, National Institutes of Health. The government has certain rights in the invention.

BACKGROUND

Onchocerciasis (river blindness) is a neglected tropical disease, caused by infection with *Onchocerca volvulus*, that has been targeted for control and elimination through mass drug administration (MDA) of ivermectin that ultimately interrupts transmission. The ultimate success of MDA for onchocerciasis will largely depend on additional tools (macrofilaricidal drugs, vaccines, sensitive diagnostic biomarkers) that in turn rely on a comprehensive understanding of the biology of *O. volvulus* and the *O. volvulus*-human host interaction.

Because of the genetic similarity between *O. volvulus* and *Dirofilaria immitis*, the causative agent of heartworm in dogs, it is expected that the *D. immitis* orthologs of protective *O. volvulus* proteins will provide protection in dogs against infection with *D. immitis* as well. Vaccination of 'at risk' dogs is an increasingly important activity as dogs are becoming resistant to ivermectin, the current prophylactic drug for canine heartworm.

SUMMARY

The present disclosure relates to immunogenic compositions for preventing or treating infection with filarial parasites and biomarkers for diagnosing infection with filarial parasites.

Thus, disclosed herein are immunogenic compositions for preventing or treating infection with a filarial parasite, wherein the filarial parasite is *Onchocerca volvulus*, and wherein the immunogenic composition comprises at least one filarial parasite protein having at least 85%, 90%, 95%, or 98% sequence identity to the full length mature protein of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), or OVOC8227 (SEQ ID NO:30).

Also disclosed herein are immunogenic compositions for preventing infection with a filarial parasite, wherein the filarial parasite is *Dirofilaria immitis*, and wherein the immunogenic composition comprises at least one filarial parasite mature protein having at least 85%, 90%, 95%, or 98% sequence identity to the full length of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), OVOC8227 (SEQ ID NO:30), OVOC9988 (SEQ ID NO:31), or OVOC4230 (SEQ ID NO:32), or an ortholog thereof. In some embodiments, the ortholog comprises a filarial parasite protein having at least 85%, 90%, 95%, or 98% sequence identity to the full length of one of SEQ ID NOs:33-49.

In some embodiments, an immunogenic composition further comprises an adjuvant. In certain embodiments, the immunogenic composition comprises at least two, at least three, at least four, at least five, at least six, at least seven, at least eight, at least nine, or at least ten filarial parasite proteins. In some embodiments, the at least two filarial parasite proteins are present in the immunogenic composition in a mixture. In certain embodiments, the at least two filarial parasite proteins are present in the immunogenic composition as a fusion protein comprising the amino acid sequences of the at least two filarial parasite proteins. In some embodiments, the fusion protein optionally further comprises at least one linker sequence separating the at least two filarial parasite amino acid sequences.

Also disclosed herein are methods of preventing infection with, or transmission of, *O. volvulus*, the method comprising administering an immunogenic composition disclosed herein to a subject in need thereof, wherein the immunogenic composition prevents the infection or prevents transmission of the infection to another subject. In some embodiments, the immunogenic composition further includes an adjuvant.

In some embodiments, the immunogenic composition is administered to a subject at risk of *O. volvulus* infection, and the administration prevents infection with *O. volvulus* and/or prevents transmission of *O. volvulus*. In some embodiments, the subject is a human.

Also disclosed herein are methods of preventing an infection with *D. immitis*, the method comprising administering an immunogenic composition disclosed herein to a canine subject in need thereof, wherein the immunogenic composition prevents the infection.

In some embodiments, the immunogenic composition is administered to a subject at risk of *D. immitis* infection, and the administration prevents infection with *D. immitis.*

Also disclosed herein are methods of detecting infection with *O. volvulus*, comprising identifying in a specimen from a subject at least one filarial full length mature protein having at least 85%, 90%, 95%, or 98% sequence identity to OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC8422 (SEQ ID NO:14), OVOC6395 (SEQ ID NO:15), or OVOC10384 (SEQ ID NO:13) or an immunoreactive fragment thereof.

Also disclosed herein are methods of detecting infection with *O. volvulus*, comprising identifying in the blood of a subject, antibodies to at least one filarial protein having at least 85%, 90%, 95%, or 98% sequence identity to the full length mature protein of OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC10384 (SEQ ID NO:13), OVOC8422 (SEQ ID NO:14), OVOC9988 (SEQ ID NO:31), or OVOC6395 (SEQ ID NO:15), or an immunoreactive fragment thereof.

In certain embodiments, the immunoreactive fragment is OVOC10469_Pep2 (SEQ ID NO:51), OVOC3261_Pep1 (SEQ ID NO:52), OVOC3261_Pep3 (SEQ ID NO:53), OVOC10469_Pep1 (SEQ ID NO:54), OVOC10469_Pep3 (SEQ ID NO:55), OVOC3261_Pep2 (SEQ ID NO:56), OVOC5127_Pep1 (SEQ ID NO:57), OVOC5127_Pep2 (SEQ ID NO:58), OVOC5127_Pep4, (SEQ ID NO:59), OVOC5127_Pep5 (SEQ ID NO:60), or OVOC5127_PepX (SEQ ID NO:61).

In certain embodiments, the specimen comprises blood, a skin biopsy, or urine.

In some embodiments, the method comprises at least two, at least three, at least four, at least five, at least six, at least seven, at least eight, at least nine, or at least ten filarial parasite proteins. In some embodiments, the at least two filarial parasite proteins comprise Ov16 and OVOC3261. In some embodiments, the at least four filarial parasite proteins comprise Ov16, OVOC3261, OVOC10469, and OVOC5127.

In some embodiments, the filarial protein or antibody to the filarial protein are detected by a method selected from the group consisting of ELISA, dipstick tests, lateral flow, microfluidic devices, luciferase immunoprecipitation systems, luminex, multiplex-formats, polymerase chain reaction, and microarrays.

BRIEF DESCRIPTION OF THE DRAWINGS

FIG. 1A depicts the number of *O. volvulus*-specific genes (light gray) and proteins (dark bars) identified across the stages by transcriptomic and proteomic analyses. ND denotes samples that were not analyzed. FIG. 1B depicts the number of *Wolbachia* (wOv) proteins identified across the *O. volvulus* stages.

FIG. 2A depicts a scatter plot of representative proteins with significant IgG4 reactivity in infected individuals, plotted as normalized intensity. FIG. 2B depicts scatter plots of representative proteins with significant IgG1, IgG3 and IgE responses in putatively immune individuals, plotted as ratios to normal sera. The four columns of data for each protein are, from left to right: Putatively Immune; Normal; Infected individuals; Endemic Normal. P values are represented by *($p \leq 0.05$), ($p \leq 0.01$), *($p \leq 0.001$), ****($p \leq 0.001$).

FIG. 3A: Ov16; FIG. 3B: OVOC10469; FIG. 3C: OVOC3261, FIG. 3D: OVOC5127; FIG. 3E: Ov16; FIG. 3F: Ov16+OVOC10469; FIG. 3G: Ov16+OVOC10469+OVOC3261. FIG. 3H depicts the positivity (in black) for each protein based on ROC (receiver operating curves) values. The false negatives for Ov16 (gray, boxed) can be picked up using combination of the proteins (OVOC10469, OVOC3261 and OVOC5127). The white denotes samples not assayed for that protein.

FIG. 4A: Ov-103; FIG. 4B: Ov-RAL-2; FIG. 4C: Ov-CPI-2M. Each dot represents larval recovery from an individual animal. Data presented are mean±S.D. Asterisk represents statistical difference in larval recoveries; P 0.05.

FIG. 5A depicts Ov-RAL-2/103 fusion protein expressed in *E. coli* and *P. pastoris* expressed protein. FIG. 5B depicts Ov-RAL-2/CPI-2M expressed in *E. coli*. Each dot represents larval recovery from an individual animal. Data presented are mean±S.D. Asterisk represents statistical difference in larval recoveries; P 0.05.

DETAILED DESCRIPTION

Figure 1A:
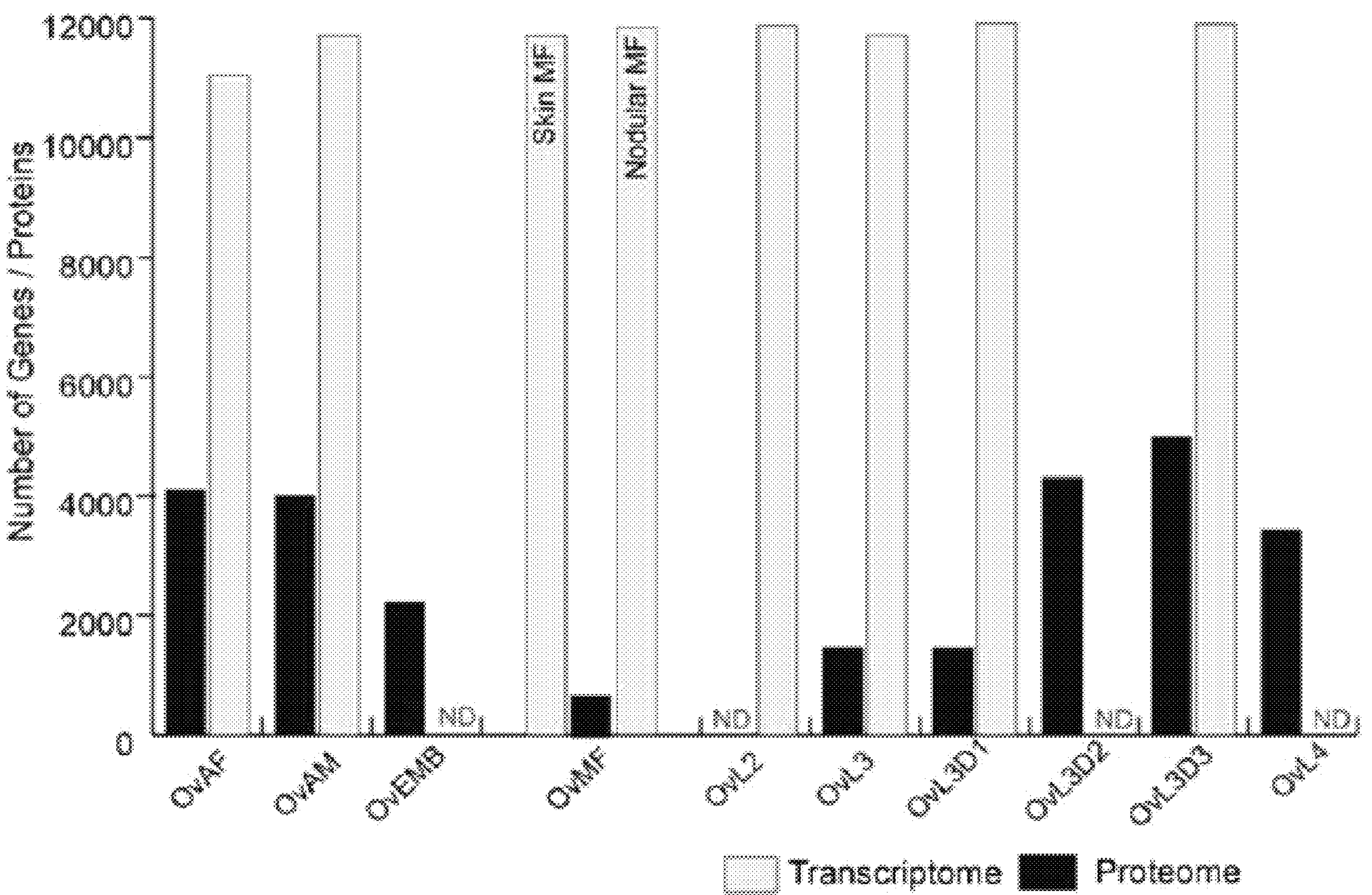
FIG. 1A-B depicts an overview of transcriptome and proteome of *Onchocerca volvulus*.

Onchocerciasis, or river blindness, caused by infection with *Onchocerca volvulus*, is a neglected tropical disease (NTD) that is associated with significant morbidity and disability in the 17 million people estimated to be infected. Infection leads to severe and disfiguring skin disease, lymphadenopathy and visual impairment (including blindness). Onchocerciasis was the first NTD targeted for control in 1974 by the World Health Organization (WHO) and is now one of the six NTDs targeted for elimination. Elimination efforts for *O. volvulus* are presently aimed by controlling transmission through ivermectin-based mass drug administration (MDA) programs, that have largely eliminated onchocerciasis in the Americas and that have made significant progress toward that goal in some regions of Africa. However, according to a new WHO evaluation, elimination would require an estimated 1.30 billion ivermectin treatments, lasting until 2045, and a recent report has suggested that onchocerciasis cannot solely be eliminated through MDA with ivermectin. Moreover, ivermectin is contraindicated in areas of marked co-endemicity with *Loa loa*, where the risk of severe adverse events is associated with high levels of circulating *Loa loa* microfilariae (mf). Furthermore, the potential for ivermectin resistance, the lack of macrofilaricidal activity by ivermectin, and the long timeline (>20 years) for transmission interruption has prompted research into the development of new tools (macrofilaricidal drugs, diagnostics, vaccines, etc.), the basis of which relies on a fundamental understanding of the parasite biology.

Humans are the only definitive host for *O. volvulus*. Because there are no existing small animal models for propagating the life cycle of *O. volvulus*, approaches that require sufficient amounts of stage-specific parasite material have been difficult, as the adult parasites must be obtained surgically from subcutaneous nodules and microfilariae from human skin. Moreover, the larval stages must be obtained from the infected blackflies—a process that to date requires feeding of newly hatched naïve black flies on infected microfiladermic humans. Nevertheless, using parasite material from most of the life cycle stages, a comprehensive profile of the stage-specific transcriptomes and proteomes of *O. volvulus* has been developed. Systematic comparisons across the parasite stages and across related nematodes and 'immunomics" has enabled the identification of novel vaccine and diagnostic candidates.

Systems biology aims at understanding biological processes by integrating various omic's data. Compared to transcriptomic data, attaining complete coverage at the protein level is fraught with technological limitations as well as the dynamic nature of any proteome. Although a difference in transcript (RNA) and protein recovery from the various stages is expected, normalization (RPKM and spectral abundance) provides provisional evidence for relative abundance of any particular gene/protein in a given stage. Using a combination of transcriptomic and proteomic analyses comprehensive stage-specific analyses of *O. volvulus* was undertaken. This dataset provides an in-depth resource for understanding and analyzing the biological pathways that are critical for the development of the various stages of the parasite in the vector and human hosts, host-*O. volvulus* interaction, and for the identification of novel biomarkers and targets for interventions.

Natural immunity against *O. volvulus* can be acquired in a few individuals within affected populations; these individuals are known as putatively immune and exhibit protective immune response against L3 larvae, suggesting that E/S products released by molting larvae and/or surface proteins of L3 larvae are an important source of protective antigens. The identification of proteins that are highly expressed by the mf and that are specifically recognized by sera from protected individuals who never developed a clinically relevant infection also suggests other suitable vaccine candidates. The identification of *O. volvulus*-unique proteins that are adult and/or mf stage-specific identified by infected individuals, provided additional novel biomarkers needed for better mapping the prevalence of infection and for post-control surveillance.

As used herein the term "transcriptome" refers to the full range of messenger RNA, or mRNA, molecules expressed by an organism at a certain time.

As used herein, the term "proteome" refers to the entire set of proteins expressed by a genome, cell, tissue, or organism at a certain time.

The life cycle of *O. volvulus* includes the following stages: nodular microfilariae (NodMF), skin microfilariae (SknMF), embryos (OvEMB), larva L1 (OvL1), larva L2 (OvL2), larva L3 (OvL3), molting L3s (L3 Day 1 and L3 Day 3), larva L4 (OvL4), adult male (OvAM), and adult female (OvAF).

Analyses of transcript levels or protein abundance for each of the stages identified 363 proteins that were found as core elements by having been present across all somatic stages. Functionally, proteins involved in metabolism, cytoskeletal processes and protein modification comprised more than 50% of these core genes. Proteins shared between OvEMB and OvAF are likely to play a role in embryogenesis. Similarly, proteins identified exclusively during the L3 to L4 transition highlight the machinery required during the developmental molt, and possibly adaptation to the human host environment. Based on *C. elegans* RNAi data, *O. volvulus* homologs of *C. elegans* that exhibit phenotypes of embryonic lethality (EMB), larval arrest (LVA), larval lethal (LVL), molting defective (MLT), or lethal (LET) were observed to be clustered not only in embryos, microfilariae (and thereby adult females), and L3 larval stages but also in adult males. This could either be due to *C. elegans* being primarily a hermaphroditic organism or to differences between gene families of parasitic and free-living nematodes.

Similarly, the *O. volvulus* genome encodes orthologues of the most critical genes essential for molting (based on *C. elegans*), orthologues that appear to be highly expressed during the in vitro molting process of the L3 larvae. However, it also highlights other proteins, some of which have already been shown to be essential for molting and/or other developmental processes of filarial parasites. For example, embryogenesis and molting in filarial parasites is dependent on the activity of cathepsin L-like cysteine proteases (CPLs).

Establishment of infection in humans depends on the successful molt from L3 to L4 larvae and subsequent development into adults. During molting, CPLs are stored in the glandular esophagus and their release during molting helps breakdown the old cuticle and drives synthesis of a new cuticle by processing the pro-proteins. Comparative analyses suggest an expansion of CPL-like enzymes in the *O. volvulus* genome. Significant transcriptional regulation of CPL and CPZ molecules was observed in L2 and L3 larvae compared to other stages. Inferring from *Brugia malayi*, a related filarial parasite, these enzymes are probably needed for the L2 to L3 molt in the black fly. Interestingly, the GO gene categories of nucleotide binding (GO:0000166), molecular function (GO:0003674), and phosphoprotein phosphatase activity (GO:0004721), were the most represented categories of differentially expressed genes during L2/L3 and L3/L4 molting. Gene set enrichment analysis (GSEA) identified immunologically important classes of molecules as enriched in L3 larval stages, and a set of extracellular matrix-related genes distinct from the ones overexpressed in adult female worms. The collagens making up the cuticle are regulated by a number of factors, one of which is prolyl-4 hydroxylase, a family that is expanded in the *O. volvulus* genome, and that is expressed in a stage-specific manner.

In contrast to those gene families upregulated during development, nuclear hormone receptors (NHR), known to play an important role in other nematode developmental processes, are comparatively less expanded in *O. volvulus* but still appear to play a role in molting and embryogenesis, as seen in *B. malayi*. Indeed the *O. volvulus* ecdysone receptor (EcR, Accession No. OVOC9104) and NHR RXR (Accession No. OVOC2435) are upregulated during the L3 to L4 developmental molt. Furthermore GSEA indicate enrichment of OVOC351 and OVOC353 (other potential NHRs) in adult female worms (p-value $<0.0001$, FDR$<1\%$). Similarly, the orthologues of the *C. elegans* NHRs-nhr-6 (OVOC8200), nhr-23 (OVOC464), nhr-25 (OVOC2839), nhr-41 (OVOC4741) and nhr-85 (OVOC827)—known to be involved in molting and metamorphosis, are present in the *O. volvulus* genome and detected as transcripts or proteins during the in vitro molting of L3 to L4. In addition, NHRs implicated in neural differentiation (OVOC635, OVOC3708) and sex determination (OVOC5276) were upregulated in the molting stages reflecting their probable role in molting, growth, and sex determination.

Protein OVOC2265 has a rather unique expression profile in the nodular microfilariae (mf) that corresponded with the proteome of embryonic stages. Among the embryo-enriched transcripts and proteins, OVOC11613 (immunodominant antigen or major antigen), and OVOC9384 (Oveg1) have been shown to be related to embryogenesis as well.

The *O. volvulus* sequences disclosed here correspond to the WS245 release of the genome by WormBase. The *D. immitis* sequences disclosed herein correspond to the WPBS1 release of the genome by WormBase. Subsequent genome releases by WormBase may have nucleotide or amino acid revisions.

I. Biomarkers

Thus provided herein are biomarkers for infection with a filarial parasite. In certain embodiments, the filarial parasite is *O. volvulus*.

In certain embodiments, if the filarial parasite is *O. volvulus*, the biomarker is a protein having at least 85%, at least 90%, at least 95%, or at least 98% sequence identity to the full length mature protein of OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC10384 (SEQ ID NO:13), OVOC8422 (SEQ ID NO:14), or OVOC6395 (SEQ ID NO:15).

In addition, the biomarker can also include proteins and peptides sharing a sequence identity or substantial sequence identity to the biomarker proteins provided herein.

As used herein, "sequence identity" or "identity" in the context of two protein or peptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art.

The term "substantial identity" in the context of a protein or peptide indicates that a protein or peptide comprises a sequence with at least 85%, 86%, 87%, 88%, 89%, 90%, 91%, 92%, 93%, or 94%, or even 95%, 96%, 97%, 98%, or 99% sequence identity to the reference sequence over a specified comparison window. In certain embodiments, optimal alignment is conducted using the homology alignment algorithm of Needleman and Wunsch (Needleman and Wunsch, JMB, 48:443, 1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, also provided herein are proteins and peptides that are substantially identical to the proteins and peptides presented herein.

In certain embodiments, the term "sequence identity" refers to identity across the entire amino acid sequence of one of SEQ ID NOs:1-66 but can include proteins or peptides which have additional amino acids at the C-terminus or N-terminus of the protein or peptide and which have at least 85%, at least 90%, at least 95%, or at least 98% sequence identity to the portion of the sequence which is the same length as the disclosed sequences.

Accordingly, some embodiments disclosed herein comprise a method of diagnosing an infection with a filarial parasite comprising: (a) providing a blood sample from at least one subject suspected of having a filarial parasite infection; and (b) contacting the sample with at least one protein selected from OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC8422 (SEQ ID NO:14), OVOC6395 (SEQ ID NO:15) or OVOC10384 (SEQ ID NO:13); wherein if the sample contains specific antibodies which bind to the at least one protein, the subject has an active filarial parasite infection. In certain embodiments, the method includes contacting the sample with at least two, at least three, at least four, at least five, at least six, at least seven, at least eight, at least nine, or at least ten filarial parasite proteins.

Additionally, some embodiments disclosed herein comprise a method of diagnosing an infection with a filarial parasite comprising: (a) providing a tissue or fluid sample from at least one subject suspected of having an filarial parasite infection; (b) providing a binding agent which binds to at least one filarial parasite-associated protein selected from OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC8422 (SEQ ID NO:14), OVOC6395 (SEQ ID NO:15) OVOC10384 (SEQ ID NO:13); and (c) detecting the proteins, individually and/or in combination, associated with the filarial parasite infection in the subject and contained in the sample; wherein if the sample contains at least one filarial parasite-associated protein, the subject has an active filarial parasite infection. In certain embodiments, the fluid sample is urine, blood, serum, plasma, or a skin biopsy. In some embodiments, the method includes detecting at least two, at least three, at least four, at least five, at least six, at least seven, at least eight, at least nine, or at least ten filarial parasite proteins.

Also disclosed herein are immunoreactive fragments of filarial parasite proteins which can be used in the methods disclosed herein. The immunoreactive fragments include, but are not limited to, OVOC10469_Pep2 (SEQ ID NO:51), OVOC3261_Pep1 (SEQ ID NO:52), OVOC3261_Pep3 (SEQ ID NO:53), OVOC10469_Pep1 (SEQ ID NO:54), OVOC10469_Pep3 (SEQ ID NO:55), OVOC3261_Pep2 (SEQ ID NO:56), OVOC5127_Pep1 (SEQ ID NO:57), OVOC5127_Pep2 (SEQ ID NO:58), OVOC5127_Pep4, (SEQ ID NO:59), OVOC5127_Pep5 (SEQ ID NO:60), and OVOC5127_PepX (SEQ ID NO:61).

Ideally, several methods, including ELISA, dipstick tests, lateral flow, microfiuidic devices, luciferase immunoprecipitation systems (LIPS), and microarrays can be used to detect filarial parasite-associated biomarkers in patients with filarial parasite infections.

ELISA is a widely used method for the detection of specific antibodies and proteins in a biological sample. It involves the immobilization of an antibody (primary antibody), or an antigen, to a solid support, such as plastic microplates, and detecting binding of components of a patient sample to the immobilized antibody or antigen, followed by the addition of secondary antibody or antibodies, the latter usually being conjugated to a detectable moiety in order to facilitate measurement.

Hence, according to some embodiments, the immune affinity procedure may be an ELISA immunoassay selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays.

In one embodiment, detection is effected through capture ELISA. Capture ELISA (also known as "sandwich" ELISA) is a sensitive assay to quantify picogram to microgram quantities of substances such as hormones, cell signaling chemicals, infectious disease antigens and cytokines. This type of ELISA is particularly sought after when the substance to be analyzed may be too dilute to bind to the microtiter plate (such as a protein in a cell culture supernatant) or does not bind well to plastics (such as a small organic molecule). Optimal dilutions for the capture antibody, samples, controls, and detecting antibodies as well as incubation times are determined empirically and may require extensive titration. Ideally, one would use an enzyme-labeled detection antibody. However, if the detection antibody is unlabeled, the secondary antibody should not cross-react with either the coating antibody or the sample. Optimally, the appropriate negative and positive controls should also be included.

Detection of the biomarkers, or of any fragment or derivative thereof, may be performed using antibodies specific to said biomarkers. These antibodies may be labeled directly or indirectly by a detectable moiety.

As used herein in the specification, the term "detectable moiety" refers to any element, molecule, or a portion thereof, the presence, absence or level of which may be monitored directly or indirectly. One example includes radioactive isotopes. Other examples include enzymes which can catalyze color or light emitting (luminescence) reactions, fluorophores, and gold or magnetic labels. The detection of the detectable moiety can be direct provided that the detectable moiety is itself detectable (i.e. can be directly visualized or measured), such as, for example, in the case of fluorophores. Alternatively, the detection of the detectable moiety can be indirect. In the latter case, a second moiety that reacts with the detectable moiety, itself being directly detectable is preferably employed. The detectable moiety may be inherent to the antibody. For example, the constant region of an antibody can serve as an indirect detectable moiety to which a secondary antibody having a direct detectable moiety can specifically bind.

Thus, secondary antibodies are particular suitable means for the detection of the anti-biomarker antibody. This secondary antibody may be itself conjugated to a detectable moiety. One of the ways in which an antibody can be detectably labeled is by linking the same to an enzyme. The enzyme, in turn, when exposed to an appropriate substrate, will react with the substrate in such a manner as to allow its detection, for example, by producing a chemical moiety, which can be detected, for example, by spectrophotometric, fluorometric, or by visual means. Enzymes which may be used to label the antibody include, but are not limited to, horseradish peroxidase, alkaline phosphatase, malate dehydrogenase, staphylococcal nuclease, δ-5-steroid isomerase, yeast alcohol dehydrogenase, α-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase, or any other enzyme which can be conjugated to an antibody and its reaction with a substrate, measured or detected.

The detection may be accomplished by colorimetric methods, which employ a chromogenic substrate for the enzyme. Detection may also be accomplished by visual comparison of the extent of enzymatic reaction of a substrate in comparison with similarly prepared standards.

The solid support to which the first antibody is bound may be any water-insoluble, water-insuspensible, solid support. Examples of suitable solid support include, but are not limited to, large beads (e.g., of polystyrene), filter paper, slides, chips, test tubes, and microtiter plates. The first antibody may be bound to the solid support by covalent bonds or by adsorption. The advantage in using a solid support is that no centrifugation step is needed for the separation of the solid and liquid phase.

The solid support mentioned above may include polymers, such as polystyrene, agarose, SEPHAROSE®, cellulose, glass beads and magnetizable particles of cellulose or other polymers. The solid-support can be in the form of large or small beads or particles, tubes, plates, slides, chips or other forms.

As a solid support, a test tube, the inner walls of a test tube or a microtiter plate are coated with a first antibody, e.g., antibodies specific to a peptide or protein disclosed herein, or of any fragment or derivative thereof.

In a further embodiment, dipstick assays may be used to detect filarial parasite biomarkers. Dipstick assays use the lateral flow format, wherein capture antibodies are striped or banded onto nitrocellulose membrane and a wicking pad draws the sample up through the dipstick, whereby the filarial parasite biomarkers interact with a filarial parasite biomarker antibody, or combination of antibodies. Other antibodies specific to filarial parasites, or other proteins of interest may be included. Subsequent analysis of enzyme activity and protein quantity may be done using standard methods known to a person skilled in the art, or as discussed above regarding ELISAs.

In another preferred embodiment, microfluidic devices, which may also be referred to as "lab-on-a-chip" systems, biomedical micro-electro-mechanical systems (bioMEMs), or multicomponent integrated systems, may be used for detecting filarial parasite biomarkers. Such systems miniaturize and compartmentalize processes that allow for detection of filarial parasite biomarkers, and other processes.

Array-based assays and bead-based assays may be used with microfluidic device. For example, a binding agent can be coupled to beads and the binding reaction between the beads and filarial parasite biomarker can be performed in a microfluidic device. Multiplexing, or detecting more than one filarial parasite biomarker at once, can also be performed using a microfluidic device. Different compartments can comprise different binding agents for different populations of filarial parasite biomarkers, where each population has a different bio-signature.

In another embodiment, microarrays are used to detect filarial parasite biomarkers. Microarrays are typically small, high throughput chips generally made of a solid support structure, typically glass slides, nitrocellulose, or microtiter plates. Generally, antibodies to specific biomarker are bound to the solid support; however, other molecules, such as, but not limited to other proteins, aptamers, DNA, RNA, sugars or lipids can be bound to the solid surface as well. Detection of the captured biomarker can also be accomplished as discussed above for ELISA detection.

In another further embodiment, recognition of filarial parasite specific biomarker is achieved through an immune affinity procedure such as Western blot, immuno-precipitation, FACS, biochip array, lateral flow, time resolved fluorometry, ECL procedures, luminex, LIPS, multiplex-immunoassay formats or any procedure based on immune recognition known to one of ordinary skill in the art.

II. Immunogenic Compositions

Also provided herein are immunogenic compositions for preventing infection with, or preventing transmission of, a filarial parasite. In certain embodiments, the filarial parasite is *O. volvulus*. In other embodiments, the filarial parasite is *D. immitis*. As used herein, "preventing transmission of" refers to the inability of an infected subject, who has been immunized with an immunogenic disclosed herein, to transmit infectious parasites to another subject via an intermediate vector.

In certain embodiments, the filarial parasite is *O. volvulus*, and the immunogenic composition comprises as least one protein having at least 85%, at least 90%, at least 95%, or at least 98% sequence identity to the full length mature protein of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), OVOC8227 (SEQ ID NO:30), OVOC9988 (SEQ ID NO:31), OVOC4230 (SEQ ID NO:32), or an immunogenic fragment thereof, or a nucleic acid encoding the protein. In certain embodiments, the filarial parasite immunogenic composition for preventing infection with, or preventing transmission of, *O. volvulus* is not OVOC9988 (Ov-RAL-2), OVOC4230 (Ov-103), or OVOC7453 related (Ov-CPI-2M). In some embodiments, the immunogenic composition includes at least two, at least three, at least four, at least five, at least six, at least seven, at least eight, at least nine, or at least ten filarial parasite proteins. The immunogenic composition can comprise the filarial parasite proteins in a mixture or as fusion proteins which include sequences from two or more filarial parasite proteins assembled in a single polypeptide sequence. If multiple filarial proteins are assembled into a fusion protein, one or more linker sequences can be included.

In other embodiments, the filarial parasite is *D. immitis*, and the immunogenic composition comprises at least one protein having at least 85%, at least 90%, at least 95%, or at least 98% sequence identity to the full length mature protein of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), OVOC8227 (SEQ ID NO:30), OVOC9988 (SEQ ID NO:31), or OVOC4230 (SEQ ID NO:32), an ortholog thereof, or a nucleic acid encoding the protein or ortholog. In some embodiments, the ortholog comprises one of the proteins of Table 6, or an immunogenic fragment thereof. In some embodiments, the immunogenic composition includes at least two, at least three, at least four, at least five, at least six, at least seven, at least eight, at least nine, or at least ten filarial parasite proteins. The immunogenic composition can comprise the filarial parasite proteins in a mixture or as fusion proteins which include sequences from two or more filarial parasite proteins assembled in a single polypeptide sequence.

As used herein, the term "immunogenic composition" refers to a substance which induces a specific immune response against an immunogen (protein) in an individual who is in need of an immune response to the immunogen. As used herein the term "immunogen" refers to any substrate that elicits an immune response in a host. Thus, the disclosed immunogenic compositions comprising filarial parasite proteins are useful for inducing an immune response against a filarial parasite. In certain embodiments, the immune response is a protective immune response. In other embodiments, the immune response is a therapeutic immune response. A non-limiting example of an immunogenic composition is a vaccine.

In certain embodiments, the immunogenic composition comprises a protein disclosed herein along with additional sequences to enhance immunogenicity.

In certain embodiments, the immunogenic composition is a fusion protein which includes several filarial parasite proteins. In some embodiments, the immunogenic composition is a mixture of one or more filarial parasite proteins. In some embodiments, the immunogenic composition includes at least two, at least three, at least four, at least five, at least six, at least seven, at least eight, at least nine, or at least ten filarial parasite proteins.

Certain amino acid sequences disclosed herein may include a signal sequence. As is understood by a person of skill in the art, expressed filarial proteins useful as immunogenic composition or biomarkers disclosed herein will not include a signal sequence. Thus, in certain embodiments, the amino acid sequences are referred to as "mature" proteins, which are proteins without a signal sequence. In some embodiments, the protein sequence will be recited as less than the entire amino acid sequence disclosed herein to reflect the absence of the signal sequence.

The disclosed filarial parasite immunogenic compositions and proteins include conservative variants of the proteins and fusion proteins. A conservative variant refers to a peptide or protein that has at least one amino acid substituted by another amino acid, or an amino acid analog, that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, physicochemical property, or the like, or any combination thereof. A conservative substitution can be assessed by a variety of factors, such as, e.g., the physical properties of the amino acid being substituted (Table 1) or how the original amino acid would tolerate a substitution (Table 2). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present specification.

TABLE 1

| Amino Acid Properties | |
|---|---|
| Property | Amino Acids |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

| Amino Acid Substitutions | | | |
|---|---|---|---|
| Amino Acid | Favored Substitution | Neutral Substitutions | Disfavored substitution |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

A filarial parasite immunogenic composition can also comprise conservative variants to the disclosed proteins or fusion proteins. In aspects of this embodiment, a conservative variant of a filarial parasite protein or fusion protein can be, for example, an amino acid sequence having at least 75%, at least 80%, at least 85%, at least 90%, at least 95%, at least 97%, at least 98%, or at least 99% amino acid sequence identity to the filarial parasite protein or fusion protein. In other aspects of this embodiment, a conservative variant of a filarial parasite protein or fusion protein can be, for example, an amino acid sequence having at most 75%, at most 80%, at most 85%, at most 90%, at most 95%, at most 97%, at most 98%, or at most 99% amino acid sequence identity to the filarial parasite protein or fusion protein.

In other embodiments, a conservative variant of a filarial parasite protein or fusion protein amino acid sequence can have, for example, 1, 2, 3, 4, 5, 6, 7, 8, 9, 10, 11, 12, 13, 14, or more conservative substitutions, to the amino acid sequence of the filarial parasite protein or fusion protein. In other embodiments, a conservative variant of a filarial parasite protein or fusion protein amino acid sequence can be, for example, an amino acid sequence having at least 1, at least 2, at least 3, at least 4, at least 5, at least 6, at least 7, at least 8, at least 9, at least 10, at least 11, at least 12, at least 13, at least 14, or at least 15 conservative substitutions to the amino acid sequence of the filarial parasite protein or fusion protein. In yet other embodiments, a conservative variant of a filarial parasite protein or fusion protein amino acid sequence can be, for example, an amino acid sequence having at most 1, at most 2, at most 3, at most 4, at most 5, at most 6, at most 7, at most 8, at most 9, at most 10, at most 11, at most 12, at most 13, at most 14, or at most 15 conservative substitutions to the amino acid sequence of the filarial parasite protein or fusion protein. In further embodiments, a conservative variant of a filarial parasite protein or fusion protein amino acid sequence can be, for example, an amino acid sequence having from 1 to 15, 2 to 15, 3 to 15, 4 to 15, 5 to 6 to 15, 7 to 15, 1 to 12, 2 to 12, 3 to 12, 4 to 12, 5 to 12, 6 to 12, 7 to 12, 1 to 10, 2 to 10, 3 to 10, 4 to 10, 5 to 10, 6 to 10, 7 to 10, 1 to 8, 2 to 8, 3 to 8, 4 to 8, 5 to 8, 6 to 8, 1 to 6, 2 to 6, 3 to 6, 4 to 6, 1 to 4, 2 to 4, or 1 to 3 conservative substitutions to the amino acid sequence of the filarial parasite protein or fusion protein.

In certain embodiments, the immunogenic compositions further comprise or are administered with an adjuvant. Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59 ® (an oil-in-water emulsion adjuvant, Novartis AG); MONTANIDE® ISA 51 or 720 (a mineral oil-based or metabolizable oil-based adjuvant, SEPPIC); aluminum hydroxide, -phosphate, or -oxide; HAVLOGEN® (an acrylic acid polymer-based adjuvant, Intervet Inc.); polyacrylic acids; oil-in-water or water-in-oil emulsion based on, for example a mineral oil, such as BAYOL™ or MARCOL™ (Esso Imperial Oil Limited), or a vegetable oil such as vitamin E acetate; a saponin; CpG oligodeoxynucleotide adjuvants; or a glucagon-like peptide (GLP) adjuvant. However, components with adjuvant activity are widely known and, generally, any adjuvant may be utilized that does not adversely interfere with the efficacy or safety of the immunogenic composition.

Immunogenic compositions according to the various embodiments disclosed herein can be prepared and/or marketed in the form of a liquid, frozen suspension, or in a lyophilized form. Typically, vaccines and/or immunogenic compositions contain a pharmaceutically acceptable carrier or diluent customarily used for such compositions. Carriers include, but are not limited to, stabilizers, preservatives, and buffers. Suitable stabilizers are, for example SPGA, TWEEN® compositions (such as are available from A.G. Scientific, Inc.), carbohydrates (such as sorbitol, mannitol, starch, sucrose, dextran, glutamate, or glucose), proteins (such as dried milk serum, albumin, or casein), or degradation products thereof. Examples of suitable buffers include alkali metal phosphates. Suitable preservatives include thimerosal, merthiolate, and gentamicin. Diluents include water, aqueous buffer (such as buffered saline), alcohols, and polyols (such as glycerol).

Also disclosed herein are methods for inducing an immune response to a filarial parasite using the disclosed proteins. Generally, the vaccine and/or immunogenic composition may be administered subcutaneously, intradermally, submucosally, intranasally, or intramuscularly in an effective amount to prevent infection from the filarial parasite and/or treat an infection from the filarial parasite. An effective amount to prevent infection is an amount of immunizing protein that will induce immunity in the immunized animals against challenge by infective stage larvae or microfilariae such that infection is prevented or the severity is reduced. Immunity is defined herein as the induction of a significant higher level of protection in a subject after immunization compared to an unimmunized group. An effective amount to treat an infection is an amount of immunizing protein that induces an appropriate immune response against filarial parasite such that severity of the infection is reduced.

Protective immune responses can include humoral immune responses and cellular immune responses. Protection against filarial parasite is believed to be conferred through serum antibodies (humoral immune response) directed to the surface proteins and/or proteins secreted during the early development in the human host, probably through antibody-dependent cellular cytotoxicity (ADCC) and cell-mediated immune responses. Cellular immune responses are useful in protection against filarial parasite infection with CD4+ T cell responses of the Th1, Th2 and/or Th17 type being particularly important. Additionally, the disclosed proteins and/or immunogenic compositions can be administered using immunization schemes known by persons of ordinary skill in the art to induce protective immune responses. These include a single immunization or multiple immunizations in a prime-boost strategy. A boosting immunization can be administered at a time after the initial, prime, immunization that is days, weeks, months, or even years after the prime immunization. In certain embodiments, a boost immunization is administered 2 weeks, 1 month, 2 months, 3 months, 4 months, 5 months, or 6 months or more after the initial prime immunization. Additional multiple boost immunizations can be administered such as weekly, every other week, monthly, every other month, every third month, or more. In other embodiments, the boost immunization can be administered every 3 weeks, every 4 weeks, every 5 weeks, every 6 weeks, every 7 weeks, every 8 weeks, every 9 weeks, every 10 weeks, every 11 weeks, or every 12 weeks. In certain embodiments, boosting immunizations can continue until a protective anti-filarial parasite antibody titer is seen in the subject's serum. In certain embodiments, a subject is given one boost immunization, two boost immunizations, three boost immunizations, or four or more boost immunizations, as needed to obtain a protective antibody titer. In other embodiments, the adjuvant in the initial prime immunization and the adjuvant in the boost immunizations are different.

Further, in various formulations of the proteins and/or immunogenic compositions, suitable excipients, stabilizers, and the like may be added as are known by persons of ordinary skill in the art.

The disclosed proteins, immunogenic compositions, and methods may be used to prevent filarial parasite infection in a subject susceptible thereto such as, but not limited to, a human, or a domesticated animal.

EXAMPLES

Example 1. Transcriptome and Proteome of *Onchocerca volvulus*

Parasite and Serum Samples. Parasite materials used for RNAseq and proteomic analyses were collected at the research facility at the Tropical Research Station, Kumba, Cameroon, and in Ecuador and Guatemala. Written informed consent was obtained. In cases of illiteracy, the participant made a thumbprint and a literate witness signed. Institutional Review Board (IRB) approvals were obtained from the National Institutes of Health, the New York Blood Center and the Tropical Research Station, Kumba. The individuals who consented to participate in the study were born, or had resided for more than 10 years, in endemic areas, and were confirmed to have, or not, microfilaria in their skin snips as well as any other clinical symptoms of disease, such as dermatitis, nodules and/or ocular lesions. In order to identify the putatively immune individuals, biopsies of the mf-individuals were also tested for the presence of the 150-mer DNA repeats specific for *O. volvulus* using PCR and Southern blot. Samples were collected before the introduction of ivermectin or from subjects that had not received ivermectin treatment prior to the studies. Adult worm samples were obtained from nodules excised during nodulectomies. Briefly, individual and cleaned freshly obtained nodules were immersed in 0.5% collagenase (Sigma Aldrich, grade IV) in RPMI-1640 containing 10% FCS supplemented with 200 units of penicillin and 200 μg/mL streptomycin. The flat tubes containing the nodule were then placed in a rocking water bath and incubated at 35° C. until the tissue was digested completely. Alternatively, frozen nodules were thawed, cleaned and digested with LIBERASE® TL (Roche) in Hanks Balanced Salt Solution (HBSS) supplemented with 3 mM $CaCl_2$. When digested, the liberated adult worms were unraveled from residual tissue with mounted needles under a dissecting scope, and then washed in several changes of RPMI-1640 or HBSS. The cleaned adult worms were stored at −80° C. until use.

L3 larvae were produced at the Tropical Medicine Research Station, Kumba, Cameroon. They were obtained from *Simulium damnosum* flies 7-8 days after infection with skin microfilariae. After dissection and washing, the larvae were cryopreserved and shipped to the USA. Fresh L3 larvae were also cultured in vitro in groups of 10 larvae in 96-well plates containing a 1:1 mixture of Iscove's modified Dulbecco medium and NCTC-135, 20% FCS and antibiotic-antimycotic (Life Technologies, Gaithersburg, MD) for 3-days at 37° C. Larvae were collected after 1, 2 or 3 days in culture, washed with Tris-EDTA and snap frozen in liquid nitrogen.

Nodular and skin microfilariae were also purified. Embryonic stages were purified from mf and eggs that were extruded into the medium during the cleaning process. The medium was collected and centrifuged at 1000 rpm for 10 min at room temperature. The pellet containing the mix of microfilariae and embryonic stages was resuspended and layered on LSM (MP Biomedicals, CA) and centrifuged at 500 rpm for 15 min with the brake off. The purified embryonic stages that formed the pellet were washed and stored at −80° C. until use.

Transcriptome Sequencing, Assembly and Analyses. High-throughput transcriptome data were generated from the RNA of *O. volvulus* stages: nodular microfilariae (NodMF), skin microfilariae (SknMF), L2 (OvL2), L3 (OvL3), L3 day 1 (OvL3D1), L3 day 3 (OvL3D3), adult male (OvAM), and adult female worms (OvAF). For all larval stages and adult worms, RNA was prepared using TRIzol® and lysing matrix D (1.4-mm ceramic spheres) and a FASTPREP24 ® (MP Biomedicals). RNA-seq libraries were prepared following the RNAseq protocols of the Illumina mRNA-Seq Sample Prep kit and the Illumina TRUSEQ® kit. Transcriptome libraries were sequenced on Illumina HiSeq 2000 machines. De novo assembly was done and is reproduced here with slight modifications. Reads were trimmed of low quality regions (<13), and only those with an average quality of 20 or more were used. Illumine primers were removed from the sequences following a parallel BLASTN of the reads against HiSeq TrueSeq adapters. Resulting reads were assembled with the ABySS software (Genome Sciences Centre) using various kmer (k) values (every fifth from 21 to 91). Because the ABySS assembler tends to miss highly expressed transcripts, the SOAPdenovo-Trans assembler was also used, again with odd kmers from 21-91. The resulting assemblies were joined by an iterative BLAST and cap3 assembler. Coding sequences (CDS) were extracted using an automated pipeline based on similarities to known proteins or by obtaining CDS containing a signal peptide. CDS and their protein sequences were mapped into a hyperlinked Excel spreadsheet. Signal peptide, transmembrane domains, furin cleavage sites, and mucin-type glycosylation were determined with software from the Center for Biological Sequence Analysis (Technical University of Denmark). Reads were mapped into the contigs using BLASTN with a word size of 25, masking homonucleotide decamers and allowing mapping up to three different CDS if the BLAST results had the same score values. Genes that had blast scores <30% of max possible score (self blast) in other nematodes with an e-value greater than 1E-05 were considered as 'unique'. To be *O. volvulus* unique, the genes were compared with the genomes of *O. flexuosa* and *O. ochengi*. Automated annotation of proteins was based on a vocabulary of nearly 290 words found in matches to various databases, including Swissprot, Gene Ontology, KOG, Pfam, and SMART, Refseq-invertebrates and a subset of the GenBank sequences containing nematode protein sequences, as well as the presence or not of signal peptides and transmembrane domains. Protein repeats were analyzed using repseq and reptile (www.reptile.unibe.ch) algorithms. Further manual annotation was done as required.

Transcriptome data (RPKM) from Excel spreadsheets was imported into JMP Genomics (SAS, Inc.) for general assessment of distribution analyses, correlations, principal component analyses, analysis of variation (ANOVA), hierarchical clustering, and heatmap generation, parallel co-ordinate plots. Heatmaps of clustering analyses were also done in R using array of packages. Differential expressing of genes was analysed using DESeq. Two replicate samples Ov1F (male) and Ov4F (female), were observed to not be exclusively male or female (pre-analyses) and were excluded from all stage-specific analyses. However, they were used for differential expression analyses with the rationale that any contaminating female transcripts present in the male sample would result in the differentially expressed genes with lower adjusted p-values to drop off and thus enriching for highly expressed genes. Likewise, any male transcripts in the female (including contributions from stored sperm and embryos) would lead to drop-off of lower range of genes and selecting for the most highly regulated genes.

Protein Depletion, Denaturation, Digestion, and Desalting. For proteomic analyses, additional stages of embryos (OvEMB), L3D2 (OvL3D2), and L4 larvae (OvL4) were also analyzed. Total soluble proteins from all the stages were extracted using the UPX universal protein extraction kit (Protein Discovery) as per manufacturer's instructions and quantified using PIERCE® BCA assay (ThermoFisher Scientific). Extracted protein samples were prepared for digestion using the filter-assisted sample preparation (FASP) method. Briefly, the samples were suspended in 1% SDC, 50 mM Tris-HCl, pH 7.6, 3 mM DTT, sonicated briefly, and incubated in a Thermo-Mixer at 40° C., 1000 RPM for 20 min. Samples were centrifuged to clarify and the supernatant was transferred to a 30 kD MWCO device (Millipore) and centrifuged at 13000×g for 30 min. The remaining sample was buffer exchanged with 1% SDC, 100 mM Tris-HCl, pH 7.6, then alkylated with 15 mM iodoacetamide. The SDC concentration was then reduced to 0.1%. Samples were digested overnight using trypsin at an enzyme:substrate ratio of 1:100 at 37° C. in a Thermo-Mixer at 1000 RPM. Digested peptides were collected by centrifugation. Twenty micrograms of the digested peptides were desalted using reversed phase stop-and-go extraction (STAGE) tips. Peptides were eluted with 80% acetonitrile, 0.2% trifluoroacetic acid and lyophilized in a SPEEDVAC® (ThermoFisher) to near dryness, approximately 1 hr.

Protein Array Construction. The following cDNA libraries from OvAM (SAW98MLW-OvAM), OvAF (SAW98MLW-OvAF), OvL2 (SAW98MLW-OvL2), OvL3 (SAW94WL-OvL3), molting L3 (SL96MLW-OvML3), and MF (SAW98MLW-OvMf) were obtained from the NIH/NIAID Filariasis Research Reagent Resource Center (www-.filariasiscenter.org) and used to amplify selected gene products. Molting larvae transcripts that were not amplified successfully from the cDNA libraries were subsequently obtained from oligodT cDNA prepared from RNA purified from OvL3D1, OvL3D2 or OvL3D3 (SUPERSCRIPT® III First-Strand Synthesis System, Invitrogen). In vivo recombination cloning was performed. Briefly, PCR primers were designed as 40 mer oligonucleotides with 20 sequence specific bases and a 20-base adapter sequence. The adapter sequences were designed to be homologous to the cloning site of the linearized T7 expression vector pXT7 and allow the PCR products to be cloned by homologous recombination in *E. coli* DH5a cells. PCR reactions were set up using HOT MASTER MIX® (5 Prime) plus DMSO (5%). The recommended cycling conditions were used and PCR products were checked for correct size using an agarose gel. PCR products were mixed with linearized pXT7 vector and were transformed into DH5a competent cells. DNA was purified using QIAPREP 96 Turbo® Miniprep Kit (Qiagen). Resulting clones were checked for insert on an agarose gel and were sent for sequencing (Retrogen).

Chip Fabrication. Proteins were expressed using a coupled in vitro transcription and translation (IVTT) system, *E. coli* based cell-free Rapid Translation System (RTS) 100 High Yield Kit (5 Prime), from the *O. volvulus* expressible clone library following the manufacturer's instructions with the exception of adding detergent to the IVTT master mix at a final concentration of 0.1% Brij 78. Shortlisted *O. volvulus* proteins were synthesized using IVTT in disulfide-bond folded formats and printed onto an array. Known immunogenic proteins (purified recombinant proteins) were also printed as positive controls.

Approximately 1 nL of unpurified IVTT reactions were spotted onto 8-pad nitrocellulose coated ONCYTE® Avid Slides (GraceBio Labs) using an OmniGrid Accent microarray printer (Digilab) equipped with a Avid™ 946 Printhead and 946MP4 Spotting Pins (Arraylt). Each IVTT expressed protein includes an N-terminal 10× polyhistidine (HIS) epitope tag and C-terminal hemagglutinin (HA) epitope tag. Microarray chip printing and protein expression were quality checked by probing random slides with mouse anti-polyHIS (Sigma), rat anti-HA (Roche) and rabbit anti-*E. coli* (LifeSpan BioSciences). Antibodies were diluted 1:1,000 in a 3 mg/mL *E. coli* DH5a lysate solution in protein arraying buffer (GVS Filter Technology) and incubated at room temperature for 30 min. Chips, FAST® Slide Holders (GVS Filter Technology) and FAST® Slide Incubation Chambers (GVS Filter Technology) were assembled and nitrocellulose pads were hydrated using 100 μL blocking buffer for 30 min at room temperature with rocking. Blocking buffer was removed, pre-incubated antibodies were added and chips were incubated for 2 hr at room temperature, washed three times with 1×TBS-0.05% TWEEN® 20, followed by incubation with Cy5-conjugated goat anti-mouse IgG Fcγ, Cy5-conjugated goat anti-rat IgG Fcγ or Cy5-conjugated goat anti-rabbit IgG Fcγ (Jackson ImmunoResearch) diluted 1:400 in blocking buffer for 1 hr at room temperature with agitation. Chips were washed three times with 1×TBS-0.05% Tween 20, three times with 1× TBS, and once with water. Chips were air dried by centrifugation at 500×g for 10 min, stored in a light proof desiccator for at least 2 hr and scanned on a GENEPIX® 4300 with Autoloader (Molecular Devices) using the 635 nm laser. Resulting 16-bit TIFF images were quantified using GENEPIX® Pro Microarray Analysis Software (Molecular Devices) and a GENEPIX® Array List (GAL) file. Spot and background intensities were measured and median spot values minus local background (M635-B) values were exported as comma delimited file (CSV).

Probing Samples. Serum samples were diluted 1:100 for IgG and 1:50 for IgE in a 3 mg/mL *E. coli* DH5α lysate solution in protein arraying buffer and incubated at room temperature for 30 min. Chips, FAST® Slide Holders and FAST® Slide Incubation Chambers were assembled and nitrocellulose pads were hydrated using 250 μL blocking buffer for 30 min at room temperature with rocking. Blocking buffer was removed, pre-incubated serum samples were added and chips were incubated overnight at 4° C. with agitation. The following day, chips were washed three times with 1×TBS-0.05% TWEEN® 20, followed by incubation with biotin-conjugated anti-human secondary antibodies against IgG1, IgG3, IgG4 or IgE (Sigma Aldrich) diluted (1:1,000 for IgG, 1:500 for IgE) in blocking buffer for 1 hr at room temperature with agitation for one hour. Chips were washed three times with 1×TBS-0.05% TWEEN® 20, followed by incubation with streptavidin-conjugated SURELIGHT™ P-3 (Columbia Biosciences) at room temperature protected from light with agitation. Chips were washed three times with 1×TBS-0.05% TWEEN® 20, three times with 1×TBS, and once with water. Chips were air dried by centrifugation at 500×g for 10 min, stored in a light proof desiccator for at least 2 hr and scanned on a GENEPIX® 4300 with Autoloader using the 635 nm laser. Resulting 16-bit TIFF images were quantified using Innopsys Mapix Software and a GAL file. M635-B values were exported for each slide as GPR files.

Data Analysis. Software developed in R (Antigen Discovery Inc) was used to process the individual GPR files in batch to create a single matrix of the raw data and to perform automated data quality checks. The raw data were normalized by dividing the IVTT protein spot intensity by the sample specific median of the IVTT control spots printed throughout the chip, then taking the base-2 logarithm of the ratio. The normalized data provides a relative measure of the specific antibody binding to the non-specific antibody binding to the IVTT controls. Normalized data was imported into JMP Genomics (SAS) and analyzed for antigen reactivity and significance (ANOVA) between the clinical groups and isotypes, and adjusted for multiple comparisons. Significant proteins were graphed in Prism 6.0 (GraphPad).

Figure 1B:
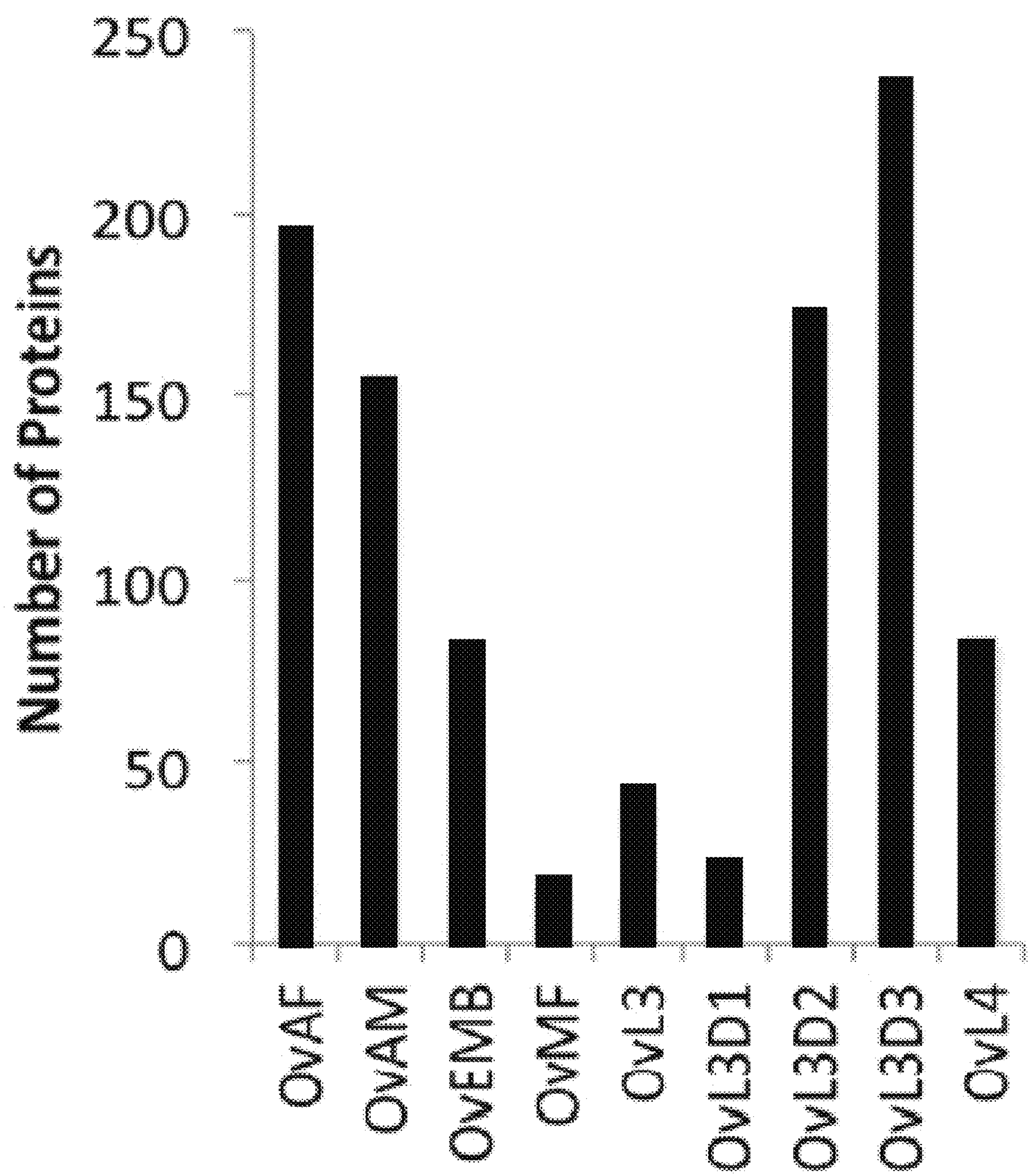

Transcriptional profiling by RNAseq resulted in the identification of transcripts corresponding to 99% of the predicted genes (FIG. 1A) across all the stages in the parasite lifecycle. Over 75% of the genes had 100% transcript coverage in all the stages except the adult female which may have been related to the age/condition of the worm(s) inside the nodule, degradation of RNA during the digestion of the nodules, or the fact that the majority of the adult female worm is comprised of uterine tissue and embryos. Several transcripts with less than 1 RPKM were subsequently identified and verified by mass spectrometry (in proteomic analyses) and thus have not been excluded. Shotgun proteomics identified proteins with a median coverage range of ~10-15% from each of the stages profiled. A total of 7,774 *O. volvulus* proteins were identified across all the stages (FIG. 1A) resulting in the validation of over 64% of all predicted proteins. Though there were no differences in the number of transcripts identified in each of the stages, maximal proteomic coverage was observed during the L3 to L4 development and in the adult male and female worms (FIG. 1A). This approach also resulted in the identification of 465 of the 785 putative *Wolbachia* proteins (FIG. 1B). *Wolbachia* is a genus of bacteria which infects some nematodes. *Wolbachia* species have been found to be endosymbionts of *O. volvulus* adults and microfilariae, and are thought to be the driving force behind most of *O. volvulus* morbidity. Overall r-values for correlations across all of the stages between the transcriptome's RPKMs and proteome abundance ranged from values that are considered acceptable for global comparisons.

Multivariate analysis revealed stage specific transcript profiles that segregated the vector-derived stages (OvL2, OvL3), the early human developmental stages performed in vitro (L3 to L4 molting: L3D1, L3D3), the adult male (OvAM), the adult female (OvAF) and the microfilarial stages (SknMF—mf obtained from skin, NodMF—mf obtained from nodules). Infected nodules often contain more male worms than female worms which has been attributed to adult male migration between nodules. The proteomic analyses indicate a probable bias towards a male-like expression profile as the worms develop from L3 to L4 and to young adults. Hence it was hypothesized that it is also likely that proportionately more male worms develop from a single infection. Indeed, structural gender differentiation can be observed in in vitro developing L4 larvae. Notable among transcriptional and proteomic profiles was the observation that, compared to all other stages, the adult males have higher transcript abundance levels with many differentially expressed genes.

Example 2. Stage-Specific Functional Enrichment

Functionally, the total putative proteome was classified into functional categories. Forty-four percent of *O. volvulus* genes have no yet known function. The distinctive biology of *volvulus* is likely to be underpinned by genes with potentially novel functions and with relatively few homologues in other helminth parasites. Approximately 9% (1173) of the predicted genes in the *O. volvulus* genome encode unique genes with less than 30% homology with other nematodes. 92% of these 'unique' genes are hypothetical or genes of unknown function of which 7% are potentially secreted. Clustering of these unique and divergent genes based on transcript and protein abundances indicates distinct subsets that are enriched in specific stages, and that these clusters have signatures of being able to be secreted ("secreted-divergent"). Although largely uncharacterized, the stage specificity of their expression is an indication of their developmental regulation and may allow for functional assignments in the future.

Gene Set Enrichment Analysis (GSEA) demonstrated that the female stages were associated with pathways linked to detoxification and the extracellular matrix. This enriched subset of extracellular matrix related genes was primarily comprised of collagens and chitin. Although the microfilariae are an integral part of the fertile adult female, genes corresponding to NADH dehydrogenase activity (GO: 0008137) and cytochrome-c oxidase activity (GO:0004129) were highly represented in adult females. In contrast, the microfilarial stages showed significant enrichment for processes associated with protein synthesis (ribosomal proteins) and protein modification with cyclophilins and chaperones (heat shock proteins) being the major contributors. These are likely the machinery required for cellular morphogenesis that occurs after being ingested by the blackfly vector.

Example 3. Secretome and Host-Parasite Interactions

The *O. volvulus* genome encodes ~20% of genes predicted to be secreted by classical secretion and about ~42% through non-classical secretion. All filarial helminths are known to release excretory/secretory (E/S) products that are critical components in the helminth arsenal of proteins that perform diverse functions that include: 1) modulating the host immune response; 2) host tissue remodeling; 3) alteration in host tissue nutritional status; or 4) enhancement of larval tissue migration. The *O. volvulus* genome encodes many of these immunologically relevant genes. Among the examples of the stage-specific enrichment of these immune-related gene products are the L3-enriched or mf-enriched cystatins and serpins that have been shown to interfere with antigen processing and presentation to T cells; the OvAM-enriched expression of indoleamine 2,3 dioxygenase (100); and the developmentally regulated L3/L4-enriched homolog of suppressor of cytokine signaling 7 (SOCS7; OVOC678). Proteases (serine, aspartic, cysteine and metallo-) are integral to host invasion, developmental molts and migration in a number of nematodes. Serine protease inhibitors also play an important role in controlling the molting process and immune evasion. The analysis of the Ov genome revealed the presence of 18 serine protease inhibitors, nine of which are highly expressed during the L3 to L4 molt. Four of these are SPI-like, probably having resulted from a duplication event of Ov-SPI-1 and Ov-SPI-2; their marked expression during the L3 to L4 molt is consistent with not only their role in early larval development but also in their putative role in immune evasion during their early adaptation to their human host. Interestingly, two of the serpins are also highly expressed in adult males indicating a potential role in spermatogenesis, while one is highly expressed in both nodular and skin mf.

Example 4. Immunomics

Figure 2A:
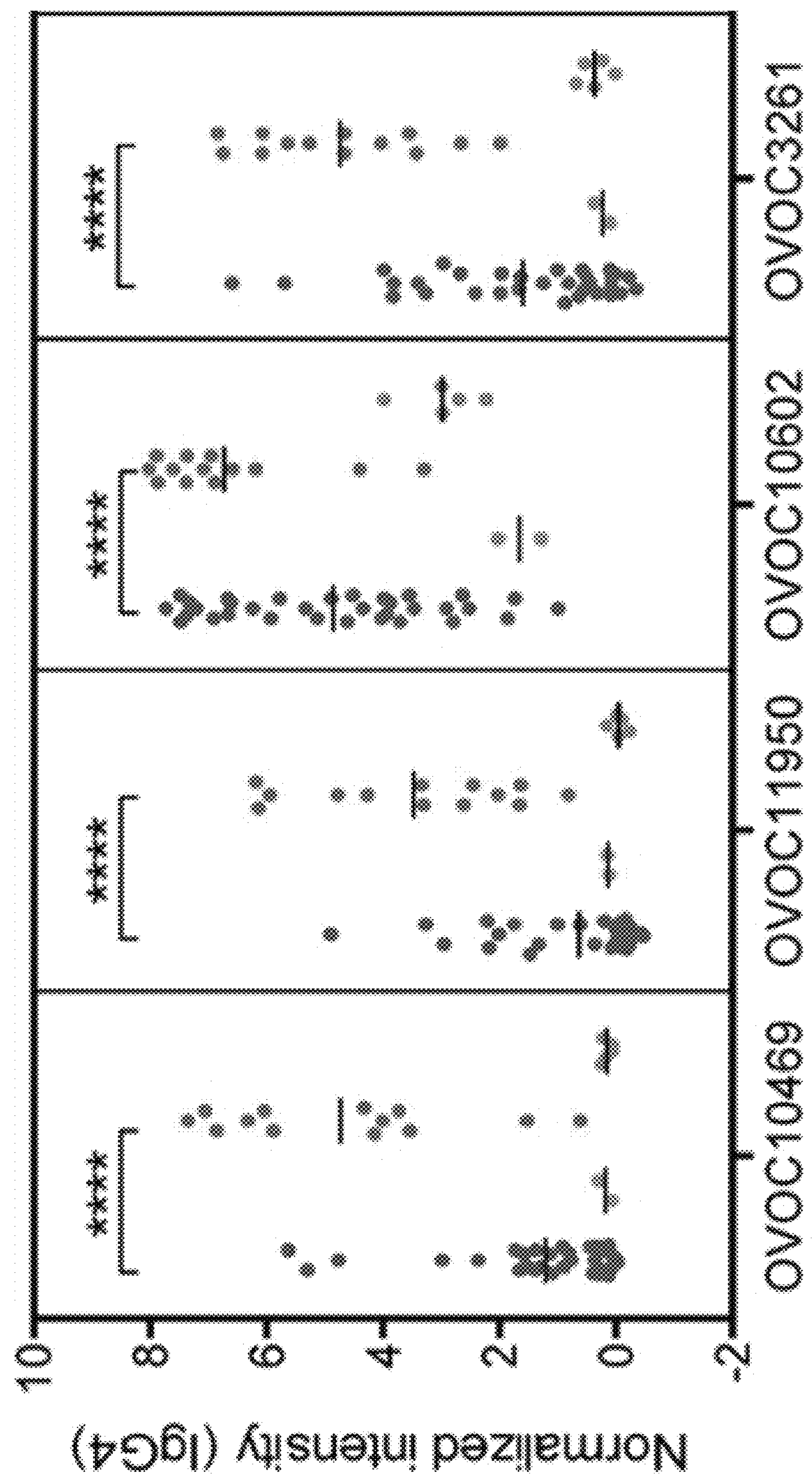
FIG. 2A-B depicts immunoreactivity of disclosed *O. volvulus* proteins.
Figure 2A:
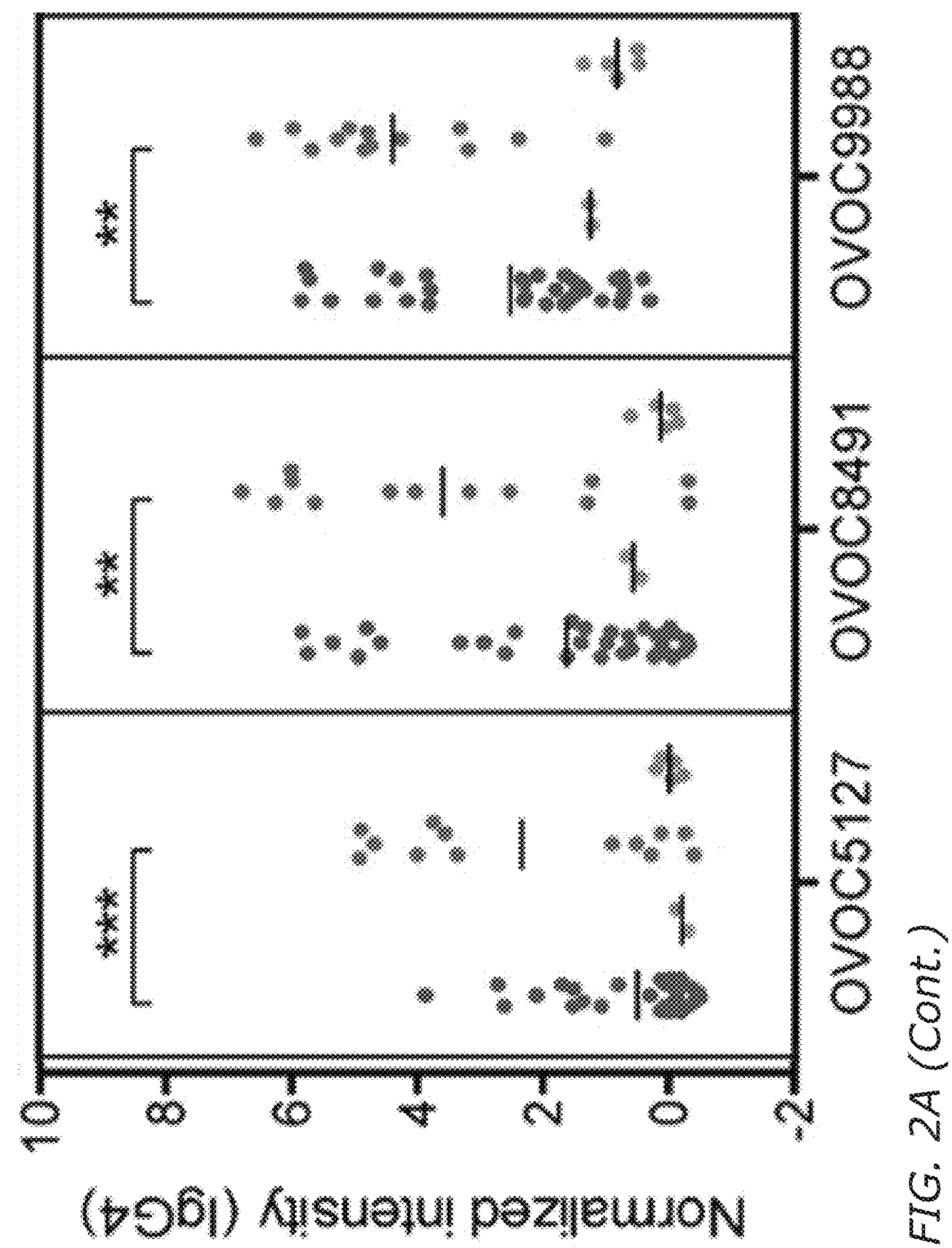
Figure 2B:
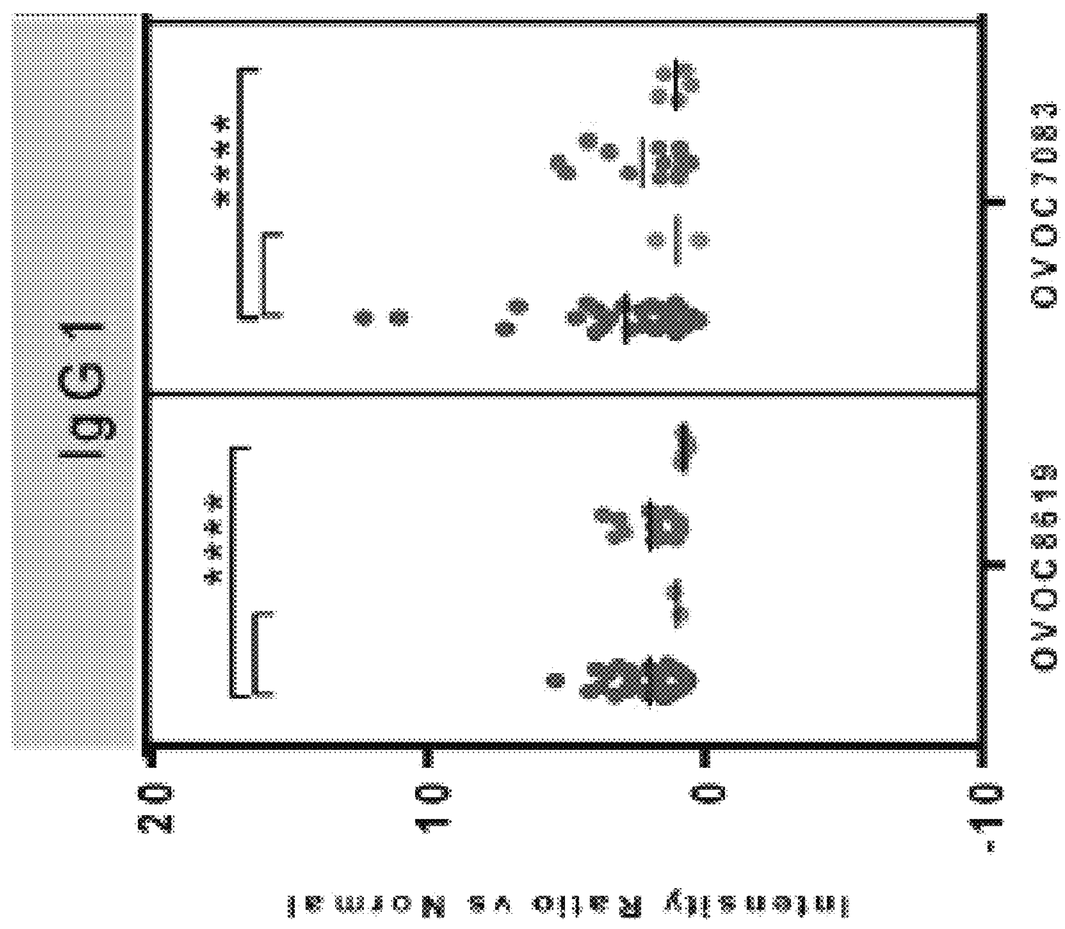
Figure 2B:
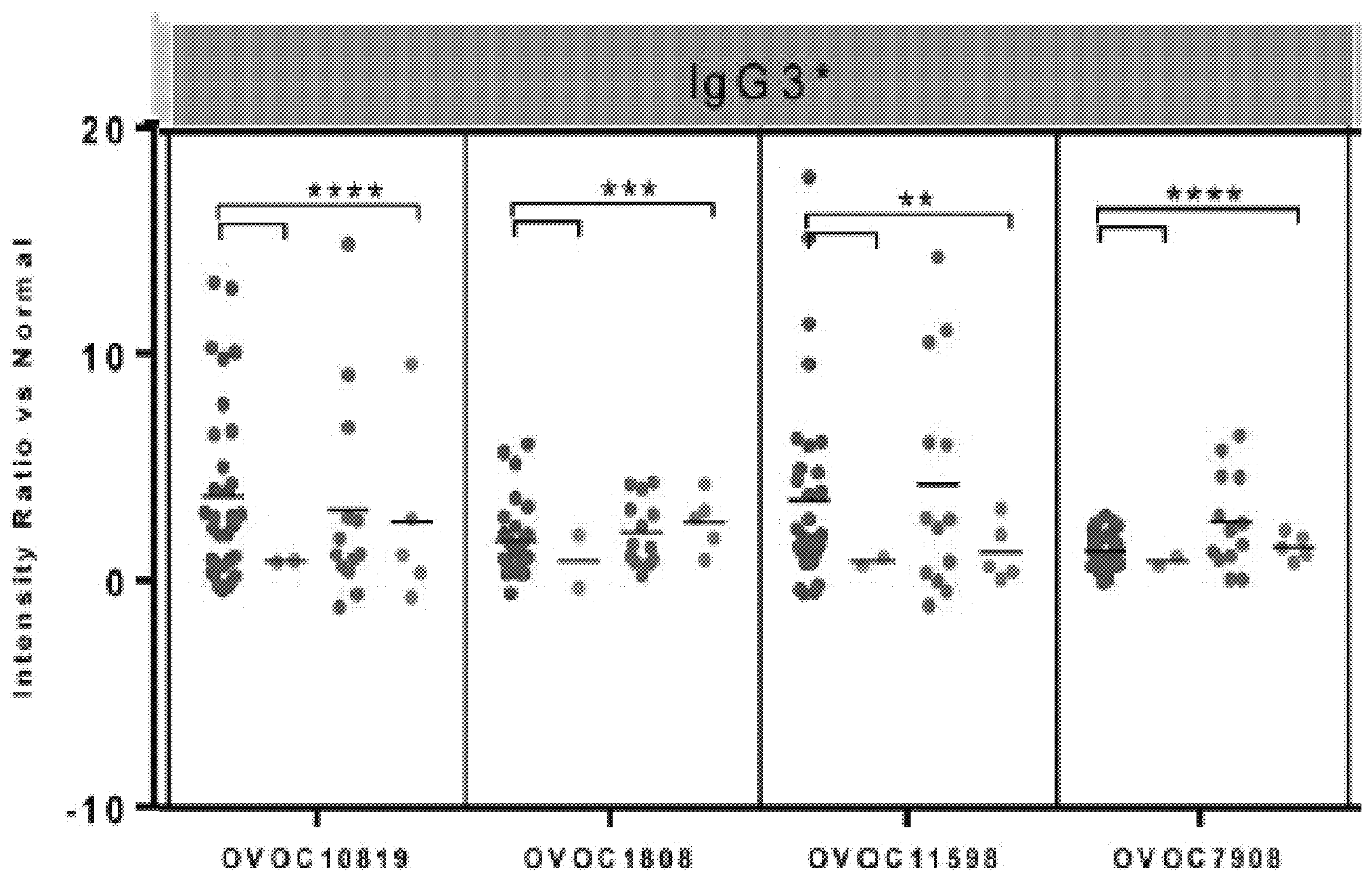
Figure 2B:
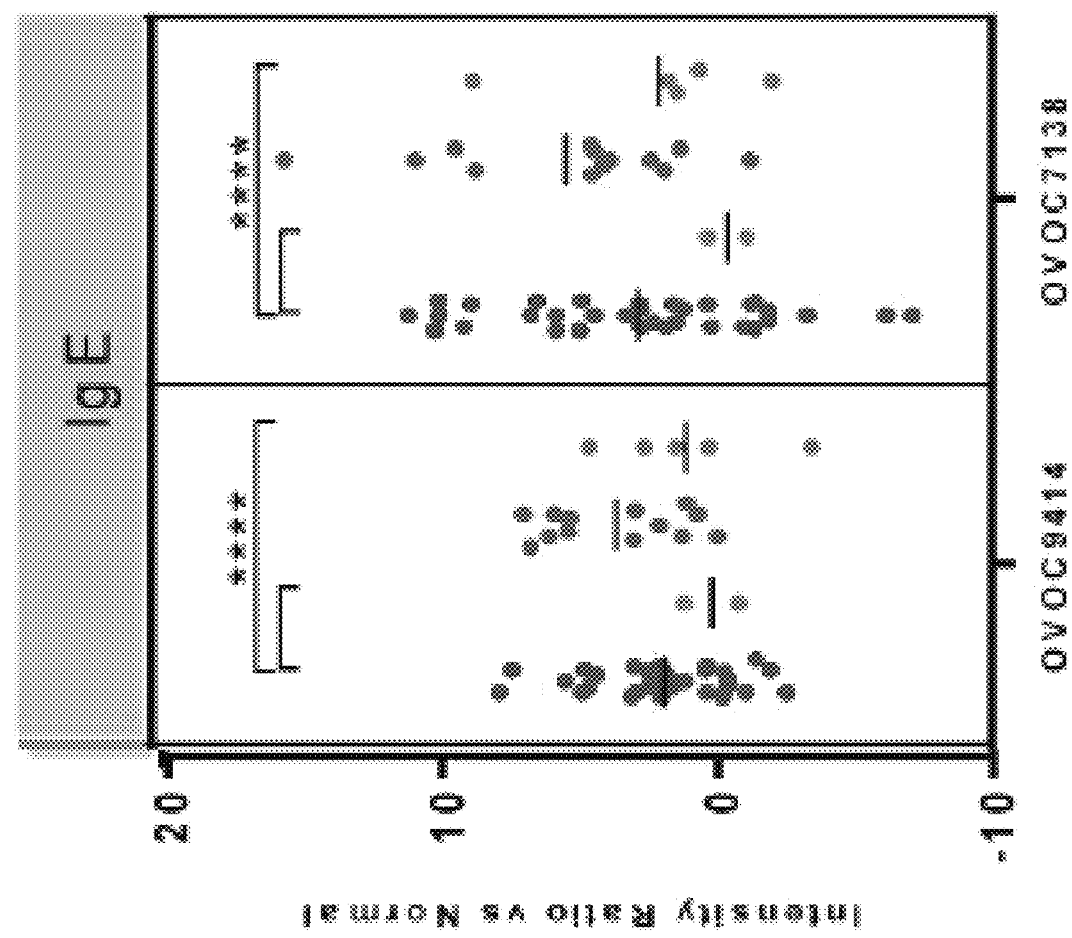

Using an immunomics approach, host antibody responses to candidate parasite antigens were profiled. Selected (397) proteins (based on their elevated expression in infective stage larvae and during molting and/or in microfilariae and/or adult stages) were printed as protein microarrays, quality checked, and assessed for isotype-specific responses (IgG1, IgG3, IgG4, IgE) with 52 individual sera comprising *O. volvulus*-infected, putatively immune, and control individuals from Ecuador, Guatemala, and Cameroon. After normalization, clusters specific for IgG4, IgG3 and/or IgG1, and with or without IgE reactivity were identified. Heretofore unrecognized biomarkers of active infection were identified (e.g. OVOC10469, OVOC10602, OVOC11950, OVOC3261, OVOC5127, OVOC8491, OVOC9988) as seen in FIG. 2A and Table 3. Further analyses led to the identification of potential novel vaccine candidates (e.g. OVOC10819, OVOC5395, OVOC11598, OVOC12235, OVOC8619, OVOC7083) (FIG. 2B and Table 4), based on IgG1 and/or IgG3 reactivity (with little to no IgE reactivity).

TABLE 3

*O. volvulus* biomarker sequences

| SEQ ID NO. | Protein Description | Sequence |
|---|---|---|
| 1 | OVOC10469 Secreted protein | NIAFAPNPKDSNNELFADAESALGSEYAQFVEQSKQHKPVYFSDNQNTLETIKLE SIPNPETETAYPMFICGFLGCMKKMNSVEEYLEHFKMHEKQGY |
| 2 | OVOC11950 Secreted protein | YPTEKETVEPIDTMVKDDIDLVKAEVAEAEEADVEKEVAELTEEEAAEIAEVL DEMEEEFFAFLLFDFILDLFRETLEKNSESQEASIDEVMPEIQGVSAEEA |

TABLE 3-continued

*O. volvulus* biomarker sequences

| SEQ ID NO. | Protein Description | Sequence |
|---|---|---|
| 3 | OVOC10602 Conserved secreted protein | FRTQSIGIRGRLMCGSKPASNERIKLWEEDSDDLLDQGYTDENGEFLLKGDTVELTPIDPVFKVYHDCDDGIKPGKRKVKFKIPKSYITEGKTPKKIFDLGTLNLETIFNDEERELIVT |
| 4 | OVOC3261 Secreted protein | SYCEDWDPEDFPSFVLKLSQNATEEFCELYEMEMEVPINKFYDMLRKWAEKYSVQAETNRFIAEEMNYDKMQSKVLMERLQASNGTTEVKGVLEKALKLQESMHLSPDYIQNVIDTMMENLPIDKQNEATLLWNSLYPDDIYNECGPRF |
| 5 | OVOC5127 DNA binding protein | APPNRDTADDLQNADMQRQWEQEQRQREEVQKEEIAKYVKYMRYLETVLNILQATPQWKEAMQSMTQEEMRGGKIAEMVDKLEPHIIEQLAKAKILELQRLEQEIKDQLNADGGATHNIKVSEILTVCLKEGFKKPSNLGIPEHLDFNNWETFSQEDLRKLIVKIVTDMDELEEQRKQDFKQYEMKKKAEEDHKMQAKMIQTEREEYIRQMEEQRRRHNKHEPLKHPGSRNQLRKVWEDTDKLDKDAYDPTTLFGLHDRNNDGYWSYDELNTIFLPEIEKLNNFSDVERLEELYRMRDHVMKQMDTDGDHRISRAEFLADREAQEEKPDQGWEDIGDKDQYTKEELEIFEKEYAKQQGWGEYAYSTPAPTPDPSRMIQPDQAPMQRLDAPSDQVGDMFAQQSHQIPVKHVEPIQSVQQQQMDEVNS |
| 6 | OVOC8491 Fatty acid retinoid binding protein 2 | FPTEANPAVGTDNAHEDNLTTEEKMQLKKFAKTNAANFSLTDPEFIDGLKNEAAGLFSKLTGLRDIINAKLDTMQPESRLFIEKLLRRFLAAFSHDGLMNILESLKGFGKEVIDMFDGLSRPIQNDILNAFPLVGSYITSDIARLMLRKLAELDLLSRKSTLTPTVDQFNDDSGKHFPRPQVIEPEEPENSDPEDAQSTDYGKKKVVTTTTFPIITGEEDEILVKKIVENK |
| 7 | OVOC6759 Conserved secreted protein | IPLPEELDYDGEIPNCRDGEKPLLAADIGVYTCDKNCPKGFRCEYRTMDSTSKKGICCPNLKELAKIYSEDEEVDKSIKKSNI |
| 8 | OVOC451 Filarial antigen Av33 | MISCFALPFPHVCYMAYCTQVIASIMKGWNQNFRFSTVIYLFRNIFSSSVISCVNMILSSTFYALLFVSAVVIVEAMPASESTYSVIIIRINDTTCKIEDGVVSVNGQVIGNLTEEQKEELEAYNVQTQGWFQQLHQKIEELFKTFFGSIKSMWKHSPISGSESSPQSSTPDNIITDKLDDQDRRLKDQGDSENSSLFGLKLPSFCKVN |
| 9 | OVOC12329 Conserved secreted protein | FRSLKIGRKQSTAVKGVLTCNGKPAVNVKVKLYNDSQGRYVENSMDEGKTDSEGRFLLQGHETSITSIDPILKLYHNCDVENAQCLKRFSILIPNDFVSEGLEPKKTFDMGTLNLGGKFFDEGRECAS |
| 10 | OVOC3337 Glycine-rich cell wall structural protein-like | QIIGSFNGNYAGDGSLNNNANSFGERTTTTRSTSRPSLPPRPGYPSRPGYPFKPGFPPRGPPIPYPHGKPSGPRYPCYGGYGGYGHPGYGPFGGNGYLGYTVCSGRGEFGGYGPGLGGGTGLGGLGPGEFGGYGPGLGGGTGLGGLGPGGFGGIGPGLGGGGGLGGPGRGGFAGYGPGLGGGRGLGGPGPGGFDGYGPGLGGRPYPGGYGRFYGPGPYPGDRLDPRGLSESGRPRTRLASYNRNDRGTQFSYIRDR |
| 11 | OVOC10264 Beta-galactoside-binding lectin | MTNEYETNYPVPYRSKLTESFEPGQTLLVKGKTAEDSVRFTINLHNTSADFSGNDVPLHISVRFDEGKIVFNTFSKGEWGKEERKSNPYKKGDDIDIRIRAHDSKYTIYVDQKEVKEYEHRVPLSSVTHFSIDGDVLVTYIHWGGKYYPVPYESGLSGEGLVPGKSLLIFATPEKKGKRFHINLLKKNGDIALHFNPRFDEKAIVRNSLIAGEWGNEEREGKMILEKGIGFDLEIKNEEYAFQIFINGERYATYAHRLDPREINGLQIGGDLEVSGIQMR |
| 12 | OVOC4230 Conserved secreted protein | DLLSEAGDFFTKHFTDIKSLFAKDEKQLQQSVDRVKDLLATIQDKMSMLQPLANDMQKTTLGKIGDLISQVNSFRETMSNPKMDFTNKENKWEELLKKIFVTEGLNKVIPLLQKLKNSAPTTFATYLFTCIVPVLINTLRE |
| 13 | OVOC10384 | MARINRLNFLLCIVHANITSAPNPKDSNDELFADAESALGSEYAQFVEQSKQHKPVYFSDNQNTLETIKLESIPNPETETAYPMFICGFLGCMKKMNSVEEYLEHFKMHEKQGY |
| 14 | OVOC8422 secreted protein | FSWKFGERLDEPVLMLRDLRAKEISPPSYMKRFESDTNEQLLRYILHPKMLRRHDLSNALFYQPLWKMR |
| 15 | OVOC6395 Protein LOAG_00657 | MEGSPIKETRGLEATPVFEMVRSATLTFLLAVSTVLVVSRPNVLLPPKLPWDSDWRQKPPPFPPEPPPEFKGILPPEIFAKLTAIHQDQSLTIPQKIVKIEEIMNSLPEDVLQRLPLPPVFRLLPQNVQEMIKTVRTTKNLTMEEKWLQMIILIESLPKQQHRLLQQMLPKFSLGPLPDFQDIIPKEDWDKLTAVYQDTNLDNIEKLRRVDEIIDALPDSIRQKIPLSPPFQKLPDHIQQQLQIIHTERGLTTEQRFRKMKAIIESLPWDMKKLMFQP |
| 51 | OVOC10469_Pep2 | EQSKQHKPVYFSDNQNTLETIKLESIPNPETETA |
| 52 | OVOC3261_Pep1 | CPSLSSYCEDWDPEDFPSFV |
| 53 | OVOC3261_Pep3 | LPIDKQNEATLLWNSLYPDDIYNECGPRF |
| 54 | OVOC10469_Pep1 | AFAPNPKDSNNELFADAESALGSEY |

TABLE 3-continued

| SEQ ID NO. | Protein Description | Sequence |
|---|---|---|
| *O. volvulus* biomarker sequences | | |
| 55 | OVOC10469_Pep3 | GCMKKMNSVEEYLEHFKMHEKQGY |
| 56 | OVOC3261_Pep2 | INKFYDMLRKWAEKYSVQAETNRFIAEEMNYDKMQS |
| 57 | OVOC5127_Pep1 | APPNRDTADDLQNADMQRQWEQEQRQREEVQKEEI |
| 58 | OVOC5127_Pep2 | TDMDELEEQRKQDFKQYEMKKKAEEDHKMQAIQTEREEYIRQMEEQRRRHNKHEPLKHPGSRNQLR |
| 59 | OVOC5127_Pep4 | DREAQEEKPDQGWEDIGDKDQYTKEELE |
| 60 | OVOC5127_Pep5 | TPAPTPDPSRMIQPDQAPMQRLDAPSDQVG |
| 61 | OVOC5127_PepX | VSEILTVCLKEGFKKPSNLGI |

TABLE 4

| SEQ ID NO. | Protein Description | Sequence |
|---|---|---|
| Immunogenic composition *O. volvulus* protein sequences | | |
| 16 | OVOC8619 Adhesion-regulating molecule | LIKVFPEISANMSVMFANSRSNQANNGYLVEFKAGRSNLQAGSTVDRRKVVADKTKGLVFIKQSSDQLMHFCWKNRETGAVVDDLIIFPGDTEFLRVRECTDGRVYMLKFKSTDEKRLFWMQDGKTDKDDENCKKVNETLNNPPAPRAAARGGADRADVSSFGTLAALGSAGAESELGALGNLDQSQLMQLLSLMNHTNSTSASEATNLLPQLPLVADTSHPMTSEDSGTTSTHGATPSNTPANGIVADSSSNNAMQLSQLKEIIASITPPDGSGRKPSIDFTDVLCCADKINDVLRKYAEQLIPHLPSQEPIYNNQEELQQTLRTPQFRQAADIFGHALQTGQLAPVLRQFGIDGNTATAAGNGDMVAWAAQFTTAENGKEITAKTETSPSQPGMESDVEDEETNEKAIRETEKNRTDDHMDLD |
| 17 | OVOC7083 Secreted protein | MNYKAPIELQQLLSITKMLSLSVLLLFTSMAIMARPPNSDEIKELRQQQLNESKDDYDTLPDVNHIPESFKESLKKQKMLYLDMLRQHNL |
| 18 | OVOC4111 Mediator of RNA polymerase II transcription subunit 15 | LSVPAGLRPAKKVGDPKEQIVPGKQQQLQQQQQQQLLQQQQQQQQQQQQQQQQQQQQQQQQQQQQQQEQQEELQQLQESEETGEEHRQQQQQQHDEALTLSPTPKVPPNLSIRSRMMAALSASVGESNKEKNSSNDETDNSSKSTNSPSKPPIIFPKANKKTVVGKIAPSGISKGSARVIVAPPSKLGTNNFGLNTVLQTNLVDSRGRIMKNVNSVPIKVPSSAEMRNARTRHTARQVESDADKVVPIKFGSTSRRR |
| 19 | OVOC1808 | NNSNLDISMREKNAVNAIEKQDLPRSHRFKRQYSCGQCGGGGGPPVVVSPCQQCKGGGAGVSAIGGAGGISAIGGGVSAIGGGFGGGGGDTVAVVCCGATGLKGMFRNWWLHIPLLLLPMSMSWIKALFL |
| 20 | OVOC11598 Secreted protein | YYVPDNYWPLRIIGYHHIPVMINMWYLFQTEISNIGVDAVLVQSPLYRTLTPDVVHDIISINVEPNHTVVVEQSNPMLQASSVEQAPAAAPLSITLIAPGITISRTHKVDTYKSTMEMYDADKLHSNEIFKRRVRKMVLPPSRGEEVRKPPSSTDGYESENVESYGQKGVEQAPPEIEQYVKKKK |
| 21 | OVOC3901 Immuno-globulin I-set domain containing protein | MKYCLSSIIAATIATTTTATAIIATTITAATISVAPFHASSPSSSLSSSSFSSFFLVLPLITTILLIVPEQAHSTATVTEHRSPPDLSIPSQTEFRVPVGTKQFRLICPVKEKNDDLLMIQWKKNDEPIGFDFNNRFKLARSDRELKIRNPQLSDGGIYQCQVVNGFGHRELNFTVTFYDPAMENDQNTDSTLTLTTKASPPIWKNETEIRNWMINPVRITIGGALLLKCPAKGNPLPHITWLRDGKVLEREITYHSSAILYLSDVQPSEGGKYICKLENEHGSIEASFHVYVENFFEGLDGESWSIDQTNAQLYPVIDEPFNNTVRVGRTAQFQCKVKNQQQPLIKWLKRVEDPNAIRQTNANATLIHANNMHLLLLEKPETSAELSDGISLNRLIIPNVRYEHSGTYLCVVTNARGDIAYRSAYLNVIARSDHGELSNLYFYGGLLVLIVVFTLITYAVHFLRKNQAAKSTESAPGITNIRYSFSLRPPPPNLPPPKAPALPSERQQLMPNNQPCDRYTVNSAAATYYPQFATPDKKLQKIITESGTRPTPIRRTNGGDTKYRLKDDYISSPKWVHAKGDNIEVEMDQNLLKNRSTHCHNPVSIAYGRIDNIDRQQQKSFLTIGNLQKR |
| 22 | OVOC10819 Secreted protein | KEIIWDCYGDYEECVAESSKMDHVDVNNVESRNIIEFCSDHTQNILPCLATKLGLIKSMSVSMFSLLLTICEAETRNNRPAATEVQQILKHLARLYAYFCAYSNVIDLRYNKECFRYLKKRCILNKPDDSCIFHHCGEKNLNLSESSPFIQQHKTTIINQLNQSATFKNYHHRITTIFTVIITFISMIQ |

TABLE 4-continued

| SEQ ID NO. | Protein Description | Sequence |
|---|---|---|
| Immunogenic composition *O. volvulus* protein sequences | | |
| 23 | OVOC5395 Protein Bm1_06245 | MYNQENHDKRRNDDRFILSLPFGTNVENKSYFKPIKLSNPYSDKYLEVNKK SSDDSDQNLNQALSVPQSNYDQSSESLSIDDSDLIDDSTSAAQLSTSSPISV TSASTSSFYPTLNIGNGMEISAKYAKLEQSQGIKSDQSTSRVSDRYKKYTA VKRRLSELYGIIEEKDEQLRVVRNELNGKDLEIGKLCDKIRALEYNCGRLQS MIESAGDESDQNQVKLHEIINERDGLLIRNASLSRQIEFEKREWSIERERLS MDLDDVTRELELQKMILNGESISEIVQRWQTKVFELEGMITDRDRAIRAQQ VQISKLKESIAETDRISCADSSESQTKFDFPSFTYIKRLLLQYLTRLADLHFSS DEERMQLVRNMSSILHLSDEEQRQVWANLKSKIQIS |
| 24 | OVOC12235 Conserved secreted protein | QCPTGSVSLLSGYRCTSSIQCQTIIPGSYCYYGVCCTGGSDVLSKTVSYGG YCTMTVQCSTTGATCISNICQCDINSHYNGHSCVSISNFCPSNQVFIKGECY RKVTYGFLCNYTQQCGYIGAFCIGNICSCQLDYTFDGSKCIPRSRICPANQI AIGGQCYPSARFGERCLYSEQCIDRWYRSLSCVNGFCNIRNDDDISKPKC RNPRAEVEYVNGTAKNCLYWPCTVGYFCEYAGGMNGGRYICCGTNANKI YGKVQLYPGTGTPLQCTEIGRCPFPDTPNCVMSYRYGYKVCCSTLN C |
| 25 | OVOC7908 Lateral signaling target protein 2 homolog | QETSEQPGLTVEIIAEQQDATTADQEVTTTVDTHHQHQHQTDKVVKSRQIT GDEQTTTTTTAINLNETITNSTTDSNSTIITTTLDLQESTTTGTTDNHHHHHH HHHHHE |
| 26 | OVOC7430 RhoA GTPase effector DIA/ *Diaphanous* | MKQTTAWGNALCVLCNCHQPQIICPPPPPAVCPRVVCPPPRPPVCPPIYC PPPVVCPPPPVCPPVPFCHSQICPPCGTHTVPVAVVGCCKGCACSVRFKR DSSSVNGLMLKKNLLCNNDQLMTIMEKKIGTNATEAAFAIKKEADSELKAKF SVFCAMNDLIYVAHAESFCQHKKGDIICFAYKS |
| 27 | OVOC8936 Microfilarial sheath protein | MDCKLILPFYILLANLEANAFHLSGYRSRSYLQGIQPYDIQPLDVQPQFIRVQ TLKSQDIQPYSIQSRSEDQPCEGCKITISCGSKNCKSKKLPYVYKPIFKLLST RSTKKPVFTLPTQPPAQWDCPCPCHVPQRCRMCSACHESYI |
| 28 | OVOC5806 Conserved plasma membrane protein | NRIISRRLSLFIQQYCCNNISQIYRLNDCKYSKVKMEIDKKIFIIVSKTEWCNE AIKVVFGKSAEAIRNNSDAISWLASYNYTGSMDLRSKWPYDAYFDNVTRTA HGLARIDLLCHKKRPQLGPRIWKRSVQKIKQKKDRPFAVNTYGNNKGLFTIT VGVLLYAAFGTCFLIANLAYLFGIYIIYDASIIDEVS |
| 29 | OVOC4665 Conserved secreted protein | IGENPMDVNAIAGIIGGISNMMQNNVETIDVPSSQIMGRWYQVYKAAIAFDV YRTDIFCPVAYFKPNSVMGEDGFSIEEAYRVITKNGPVETYKRDLNKVGTG QYWMYTEEYFYPRQFNIISVGPNYTNTTDGSEEEKQYQYMVVTDGNRLSL SVYARHPMIFYQKYNEEVVKFLEHAGFGGKVFWNSPKPIYQGADCEWPSE KEVFARRVLKNQELAKNGGLDTATKSGSFGGSSQATDVRSSITEILQNPQL ALQKLVQGH |
| 30 | OVOC8227 HAD-superfamily hydrolase | MTIIKSMLKITHVIFDLDGLLIDTEVVFSKVNQCLLSKYDKKFTPHLRGLVTG MPKKAAVTYMLEHEKLSGKVDVDEYCKKYDEMAEEMLPKCSLMPGVMKL VRHLKTHRIPMAICTGATKKEFEIKTRHHKELLDLISLWVLSGDDPAIKRGKP APDPFLVTMDRFKQKPEKAENVLVFEDATNGVCAAIAAGMNVVMVPDLTY MKIPEGLENKINSVLKSLEDFKPESVGLPAYDASSNE |
| 31 | OVOC9988 Serine/ threonine protein kinase DDB_G0280133 | IPQRRQQQQQQQQQQQRDEREIPPFLEGAPPSVIDEFYNLLKTDENKTDQ QTEADVEAFINRLGGSYKVRFTQFMEEVKKARADYERIHQQAVARFSPAA KDADARMSAIADSPHLTTRQKSQQIQAIMDSLSESVRREIINALSPQE |
| 32 | OVOC4230 Conserved secreted protein | DLLSEAGDFFTKHFTDIKSLFAKDEKQLQQSVDRVKDLLATIQDKMSMLQP LANDMQKTTLGKIGDLISQVNSFRETMSNPKMDFTNKENKWEELLKKIFVT EGLNKVIPLLQKLKNSAPTTFATYLFTCIVPVLINTLRE |
| 62 | OVOC7453 (CPI2M) | KNPSKMESKTGENQDRPVLLGGWEDRDPKDEEILELLPSILMKVNEQSKD EYHLMPIKLLKVSSQVVAGVKYKMDVQVARSQCKKSSNEKVDLTKCKKLE GHPEKVMTLEVWEKPWENFMRVEILGTKEV |

Natural immunity against *O. volvulus* can be acquired in a few individuals in affected populations and these individuals are known as putatively immune. Consequently, they exhibit protective immune response against L3 larvae, suggesting that E/S products released by molting larvae and/or surface proteins of L3 larvae are an important source of protective antigens. The identification of proteins that are highly expressed by the mf and that are specifically recognized by sera from protected individuals who never developed a patent infection opens up new possibilities for also developing a safe anti-transmission or therapeutic vaccine. The identification of Ov-unique proteins that are adult and/or mf stage-specific that are recognized by sera of Ov-infected individuals provided additional novel biomarkers needed for better mapping the prevalence of infection and for post-control surveillance.

It is anticipated that *O. volvulus* proteins, or orthologs thereof, will provide protection against infection with *D. immitis*. *D. immitis* orthologs of *O. volvulus* proteins are provided in Table 5.

TABLE 5

*D. immitis* orthologs of *O. volvulus* proteins

| SEQ ID NO. | Protein Description | Ortholog of | Sequence |
|---|---|---|---|
| 33 | nDi.2.2.2.t 00004 Proteasomal ubiquitin receptor ADRM1 homolog | OVOC8619 | MRTASQLTFMLFLVLKKKFKNIDKLFSQISVNMSVMFANSRS SQANSGYLVEFKAGRSNLQAGSTVDKRKVVADKTKGLIFIKQ SSDQLMHFCWKNRETGTVVDDLIIFPGDTEFLRVKECTDGRV YMLKFKSTDEKRLFWMQDGKTDKDDENCKKINETLNNPPAP RAAARGGADRAGASSFGTLAALGSAGADSELGALGNLDQN QLMQLLSLMNHTNSASASEAANLLPQLPLVADTPNPVASEES GTTSTQGATPSNTPANGIIAGSSSNNAVQLSQLKEIIASITPPD GSIRKPSVDFTDVLCCADKINDVLGKYAERLIPHLPNQEPIYN NQEELQQTLRTPQFRQAVDIFGHALQTGQLAPILRQFGIDSN TAIAAGNGDLIAWATQFTTSENEKEIAVKTETLPFHPGMESDV EDEETNEKAVRESDKNRTDDHMDLD |
| 34 | nDi.2.2.2.t 03357 | OVOC7083 | MLPTLYINNAVIRPVLSETKKVKVQNISSPFLIFLLLSITKMLSLS VLLLFISMATMARPPNPDEIKELHEQQLNDSKDDYDMLPDVG HIPESFKESLKKQKMLYLDMLRQQSL |
| 35 | nDi.2.2.2.t 05919 | OVOC4111 | MISSRLRITIPESIVIFGIFCFFIFFCFLSFFFFFTLWSHRDTINFQ TDFMTETIKFIVYAVVILRMMFFDIVCFYSFLMMTIVLINTSNGL SVPAGLRPAKKVGDPREQIVPGKEQQQQREQQQQQQQQLQ EEEQQQQQQHDEVSNLRPTPKVPPNLSIRSRMMAALSASPV EPNKEKNSSKVETDSFSKPPIIFSKGNKKTVPGKIAPSGSSKG NARVIVAPPADLGKNNYGLNTVLQTNLVDSHGRIMKNVNSVPI KVPSSAEMKNARTRHTARQVESDADKVVPIKFGSTSRRR |
| 36 | nDi.2.2.2.t 07753 | OVOC1808 | MMRIKWIILLLLLLLLPIITAEFSAPVGTNSSLTIFDKDKQVLLRSD RLKRQCGPCGVAPSPVIVCCGAAGLKEIFRSWWLHIPLLLLP MSTSWLKTMVC |
| 37 | nDi.2.2.2.t 06812 | OVOC11598 | MFRLLIAIQILRFCQANYINDVYWKRSIIGYQHIPIILNICYLLQTE VSNKGVVDALFLHSPTYHRVEMSEETDNIESIADKSNITVANKP NLMIYPADFQVSSNERASASIPITITITSSGDTIIKSFKHKHQSNE IFKRRVAKMAIAPVNAPEVENLAPEVENPSPSTAGYESKTEEQ APSESGQYGKRRK |
| 38 | Fibroblast growth factor receptor-like 1 nDi.2.2.2.t 10368 | OVOC3901 | MYNLAKLLENEHGSIEASFHVYVENFFEGLDGESWSIDQTNA QLYPIIDEPFNNTVRVGRTAQFQCKVKNQQQPLIKWLKRIDDP NAIRQANANATLIHANNMHLLLLEKPETSAELSDGISLNRLIIPN VRYEHSGTYLCVVTNAHGDIAYRSAYLHVIARSDHGMLSNIYF YGGILVLIVVFTLITYAVYFLRKNQAAKNSESAQDITNTRYSFSL RPPPPNLPPPKAPALPSERQQLMSDNQPCDRYAVNSAATTYY PQFATPDKKLQKIITESGGTRPTPIRRTNGGDTKYRLKDEYINS PKWVHTKGDNIEVEMDQNLLKNRSSHCYNPISGAYGRTDNID RQQQKSFLTIGNLQKR |
| 39 | nDi.2.2.2.t 02919 | OVOC10819 | MLKLANTEIFFIAFLVYSKEIILNCYEDYKECVATSNKTNHVNMD NVNPQNLIEFCFDHTQNILPCLVTKLGLTKGISVSIFSLFLSTCE LEAQNNKSSSTTEMQQILRHLLRLYAYFCAYSNIIDLHRNRECF RYLMKRCVLNKPDESCMFYHCGKIHFNLSKSSRKILFTRQHDT TKIVNLGNKMNQLATFNNHQVRSAVVVTLIITFIDMIQ |
| 40 | nDi.2.2.2.t 01093 | OVOC5395 | MYSQENQDDKRRNDERIALSVPYNNTNIMDRSYFKPIKLSYPY SDECLEVNKKSSDDSDQRLSQNSSTPQSNYDQSSERLSIDDS DLIDDSTSAAQLSTSSPISVTSASTSSFYPTLNIGNGMEMNAKY AKIEQSEGIRSDQSSTLRISDKYKKYTAIKRRLSELCGIIEEKDK QLRVVRNGLNEKDLEIGKLCDKIRALEYNCGRLQAVIESVGDE SDQNQIKLHEIINERDGLLVRNASLSRQIEFEKREWSIERERLS MDLDDVTRELELQKMILNGENISEIVQRWQTKVFELEGMIADR DRAIRAQQVRISKLKQSLAEADRISCDDSSESQTKLDSPSFTCI KRLLLQYLTSSDEERIQLLRNVSTMLHLSDDEQHQVLTNLKSRI QIS |
| 41 | nDi.2.2.2.t 11596 | OVOC12235 | XKCRDQRAEVEYVNGSAKNCLYWPCTVGYFCEYTESRNGGH YICCGTNANNIYGKVKVYPGTNKPLHCSIMNTCPFLDTPNCVM SHRYGYKVCCSTMNC |

TABLE 5-continued

*D. immitis* orthologs of *O. volvulus* proteins

| SEQ ID NO. | Protein Description | Ortholog of | Sequence |
|---|---|---|---|
| 42 | nDi.2.2.2.t 05701 | OVOC7908 | MLMKQSDSCVDYFYDQYKGQEYVKDDAFNTQNITDNFRKSS SDIAQLMNSQIELISQPEKVNEDSAKSSHYNDDLQKSIEDDTVE ATQRKKDEKLLEFLHSLIVSTIPKTIHLEGNSVNLLTLTTTITPIAII TTKNTSGTANAITTRKYKKYKLNAFVNISSDTLTELPKFLPENF NSTNFANVEKTEKFSNSKQVATDSIFSLKESAYLETPVIRDFSS ANDSAKTDPLFTRNYVDKQIDMNTTKFNKNLKKSRLTTISTSNL TTVLSQLQTTTSISTTTSVTTTISTSITIPELTLVSQSHRHLHHYH HHHHHQYENYDHESPIIVTALFDIGRGKWPRYTRTYEQYMNY LKHLLKLENCLVIYTDSRGAEFVRQTRNVHNTQIFEISMHDLPL YRYREEMKGIIQREQKDWQFSPKTRYHPEANSADYNIIVNSKP YFLYNATQNVRFRTSDRMFVWIDAGYGHGRKGIIPDHCHWRP RLQRDRMTIIQLTPKHDKVSRYSITDLYRVDWVVLSGGFIAGD SHTINRFYRFYQKLFMELLDSGRIDDDQTILTLMLKHYTTLFNPI SSNGDWYALFRLFPCHDRQ |
| 43 | nDi.2.2.2.t 04336 | OVOC7430 | MKQATTWGSICEMCPCAAKPICPPPVICPPRICPPPVICPPQIC PPCPPRICPPPVICPPQICPPCPPQICPPCPKPQPPPPPPPPV LPSLPPTSFKPMITCCRTCICYIRRKRDSLNDYDRIHDINPVCN NDQLMMIMKKKIRTNVTESTIAIKKAADSMLQAEFNVFCAINDL THVAHAEHFCQYKKDNSVFDSFLFRSTLKGLIEECREGVRWW PGSLGDLDFSHISLYRAHKYIGNEEMNRSTKTKISFTRINKKWR LGHTGKKYNKVRFSRNIAKKFIGVCNIIRLKKSVSRSVRPFENQ KSTSFNVFQLLVPKEKVEIVVDDTQAEEMNSETAQEVQLFNVR KSNADSKTDGEKDTADLDVILLTNEECSSSRQENLNKDEPEIVI LDDSAPSKSDLNTSDEIICLQDLKMVNEVPTFSVTPKQKTVKEL PRETRTYGTRRGRQSRAYCEDLRKFPSIRNPVSSSSSSIHAKN MPEFVDLLTQGTLLICKKWLRRWDIVQSGVIGGNPLRICSYNV LCQQTAYKTPELYIHLTKPGRAYELTWENRWRLLTREFSMIGA DIFCLQEVQYDHYDQFFRPYFEAAGFFGKYKKRTNNLLDGCAI FYKSHLQLLHYRYIEYFLNIDSVLNRDNVGQLIRLKDMRSGREF CVVNTHLLFNKRRGDVKLAQLAILLANIDQECGPESGQECPYIL CGDFNFHPYSPIYNFIMNGEICFTNLRRGDISGQGNAGGPFVS VNLLPEDVKIARNCRFNYLKNRTMLLPSLNCWSHPLCFNSVY QNMNGETRPMISTYHSIEAVNPDFIFYSVKSKRVQQSMLPHSV PAMNVSEREIRLIRRLSLPDMNELAGTLGPWPNSTTPSDHIPLI ADFVLQ |
| 44 | nDi.2.2.2.t 10647 | OVOC8936 | MYCKLIISFYMLLSIANMTHLVGYRPQIYLQGIPQNIQSHDIQRL DMQQQSLKLPDTELYSIPSHDNQLQGLQLYDMQFQGKQSKG SEKLCSGCKISINCSGKKCVPMRTRKPIVTTPSPLSTQRPVLTR PRLLADCPCPCHVSRQCRICQPCQESFI |
| 45 | nDi.2.2.2.t 03537 | OVOC5806 | MFVGMRLYLAIDVLLLLVLRIKSNRIILHRFSLFIQQHCCNNISQI HRLNDCKYSKVRMKIDKKILIIVSKTEWCNEAIKVVFGKSAEAR RNRSDAISWVTPYNFTGLMNLHSKWRYDAYFDNVTRTAHGLA RIDLLCPKRRSHSGRRILKRSIQENKQEKSRRSFTVNIYGSSKG IFTITVGVVIYAIFGVCFLITNMAYLSGIYTVHNTSVIPEDKKRKE TSKRKEIL |
| 46 | nDi.2.2.2.t 01073 | OVOC4665 | MISVFLLLTVIVSYVETIGENPMDINALAGIIGGISNMMQNNVETI DVPSSQIMGQWYQVYKAAISFDAYKTDMFCPVAYFKPNSVMG EDGFSIEEAYRVITKNGPVETFKRDLNKVGTGQYWMYTEEYF YPRQFNIIGVGPNYTNATDGREKENLYEYMIVTDANRLSLSVY ARHPMIFYQKYNEEVVKFLEHAGFGGRVFWNSPRPIYQGTDC EWPSEKEVFARRVLKNQEAARNTGLETATKSGLFGSSLTTDA YNPIKEMLQNPQLALQKLVQGH |
| 47 | nDi.2.2.2.t 00378 | OVOC8227 | MTVIKSMLNITHVIFDLDGLLINTEIVFSQVNQCLLSKYGKKFTS HLRGLVTGMPKKAAVAHILEHERLSEKIDVDEYCKKYDEMAEE MLPKCSLMPGVMKLVRHLKAHSIPMAICTGATKKEFELKTRCH KELLDLISLRVLSGDDPAVKRGKPAPDPFLVTMERFKQKPEKA ENVLVFEDATNGVYAAIAAEESKIVK |
| 48 | nDi.2.2.2.t 01674 | OVOC9988 | MILEQLEVPPFLVGAPQSVIKQFYDLLKADETKTDAQTEADVE AFINRLGGTYKTRFDQFKQEIKQGKAAYERLHQQAVAKFSKEA READAKMSAIADSPSLTTQQKTQQIQAIMD |
| 49 | nDi.2.2.2.t 06953 | OVOC4230 | MLKYGILLILITVGAYCDLLSEAGDFFSKHFTDFKSLFASDEKQL QQNMDRVKDLLATIQDKMTILKQLADNSQKSTLEKITDIISQVN DFRENVFNSNVDFNQKKTKWEEVVTKIFVTDGLNKVIPLLQKA KNSAPATFITYLLTCIVPLLINALRE |

Example 5. Immunoreactivity of *O. volvulus* Proteins

Figure 3A:
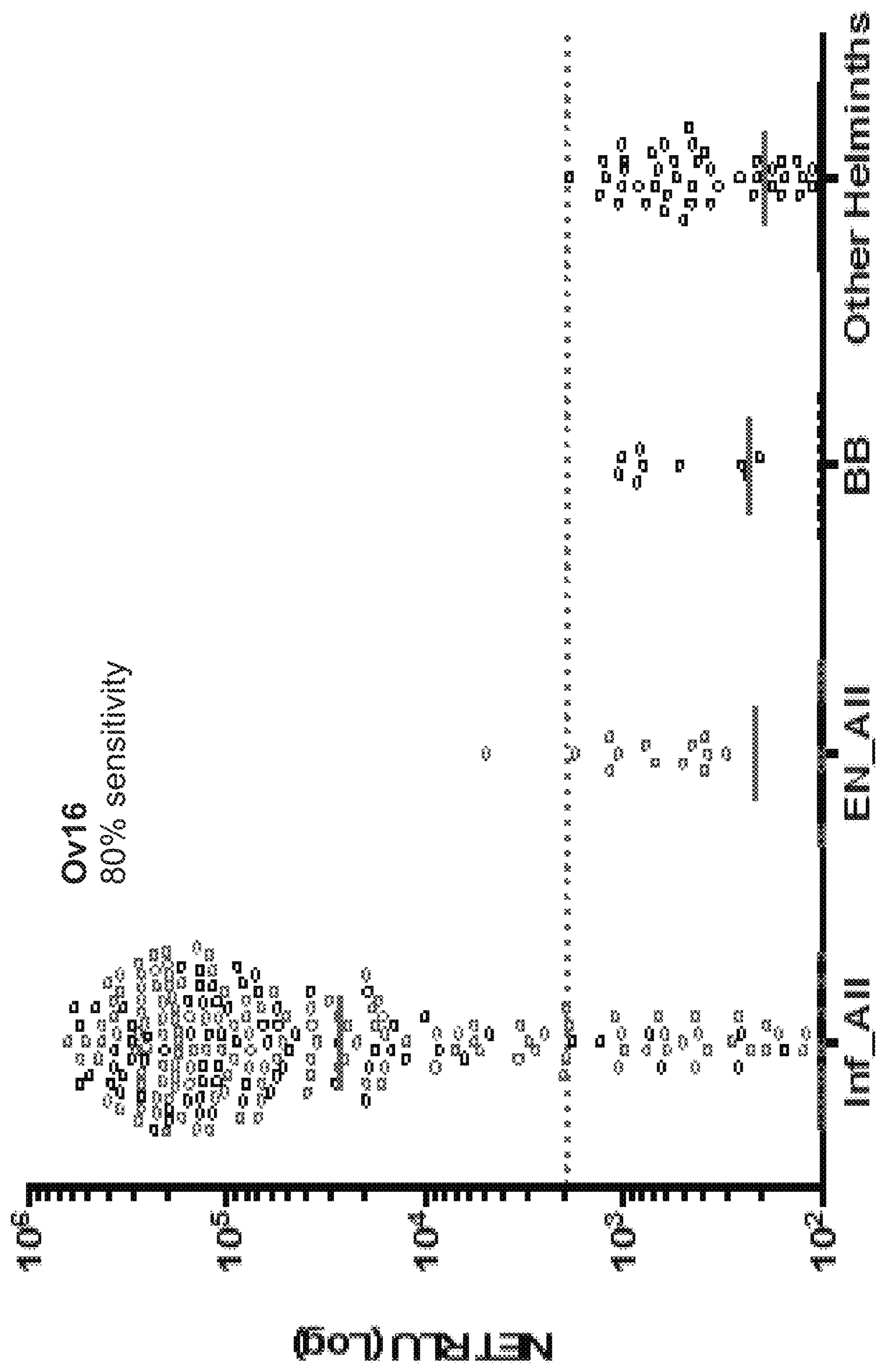
FIG. 3A-H depicts the sensitivity of the biomarkers for *O. volvulus* infection.
Figure 3B:
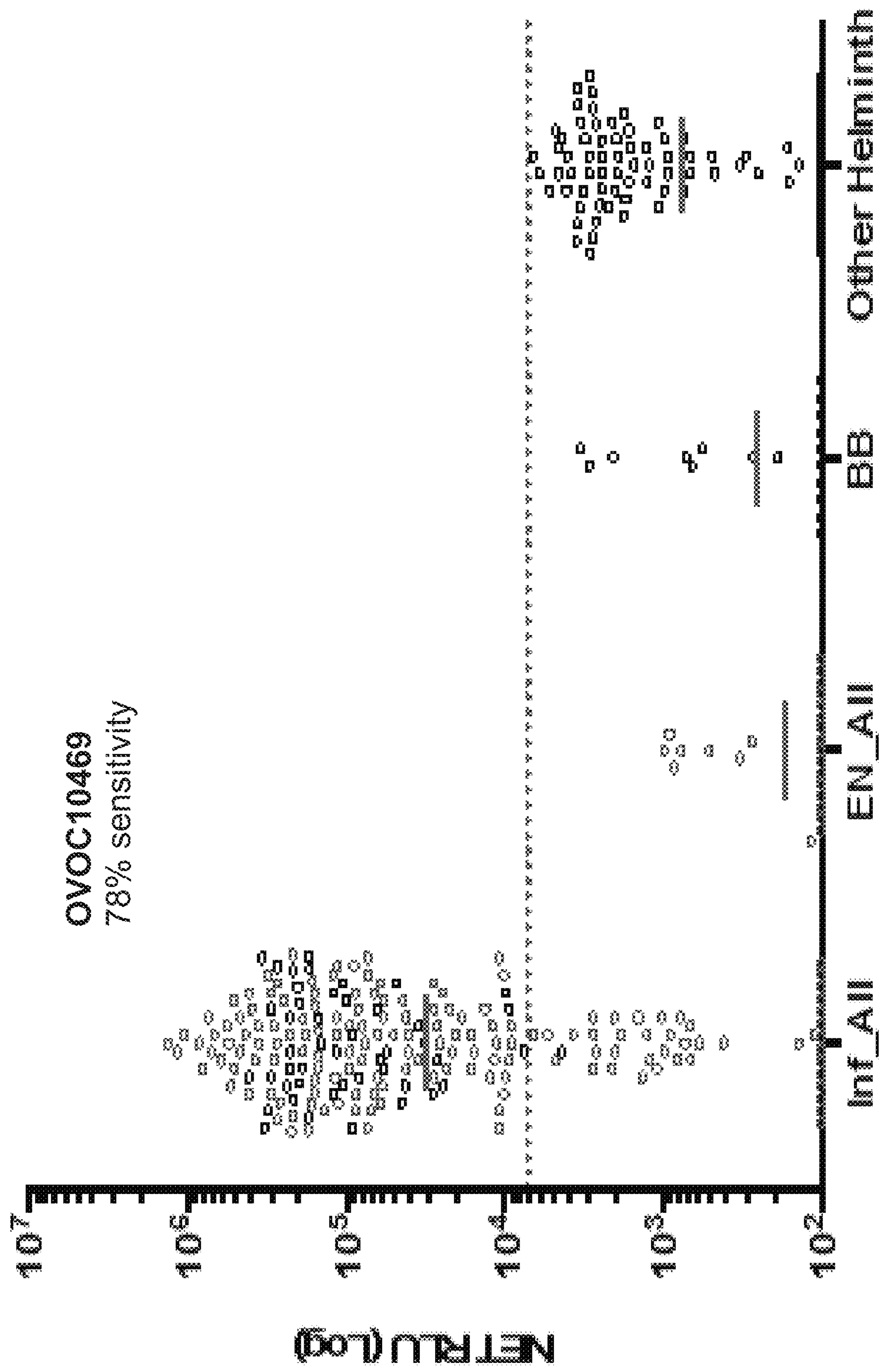
Figure 3C:
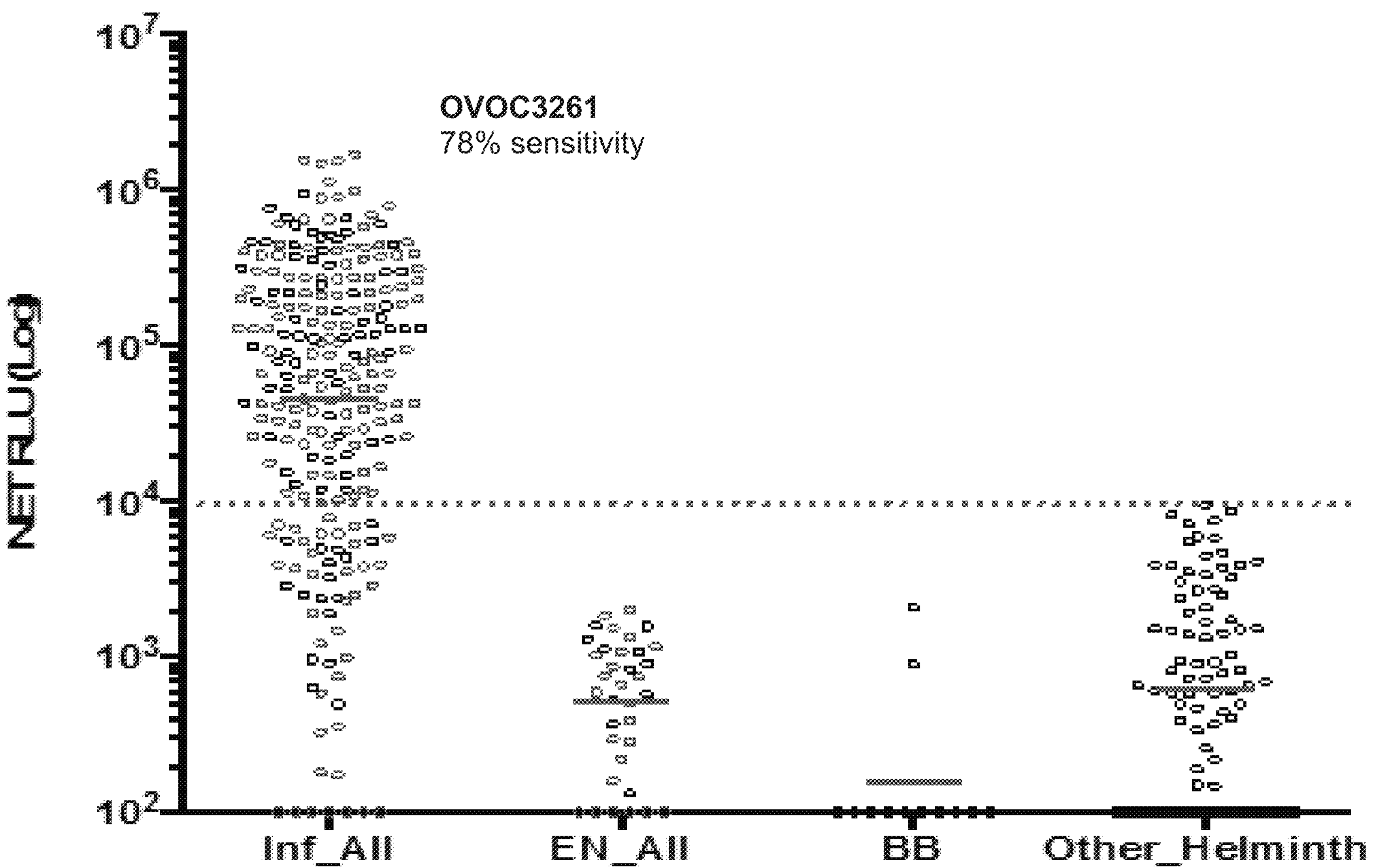
Figure 3D:
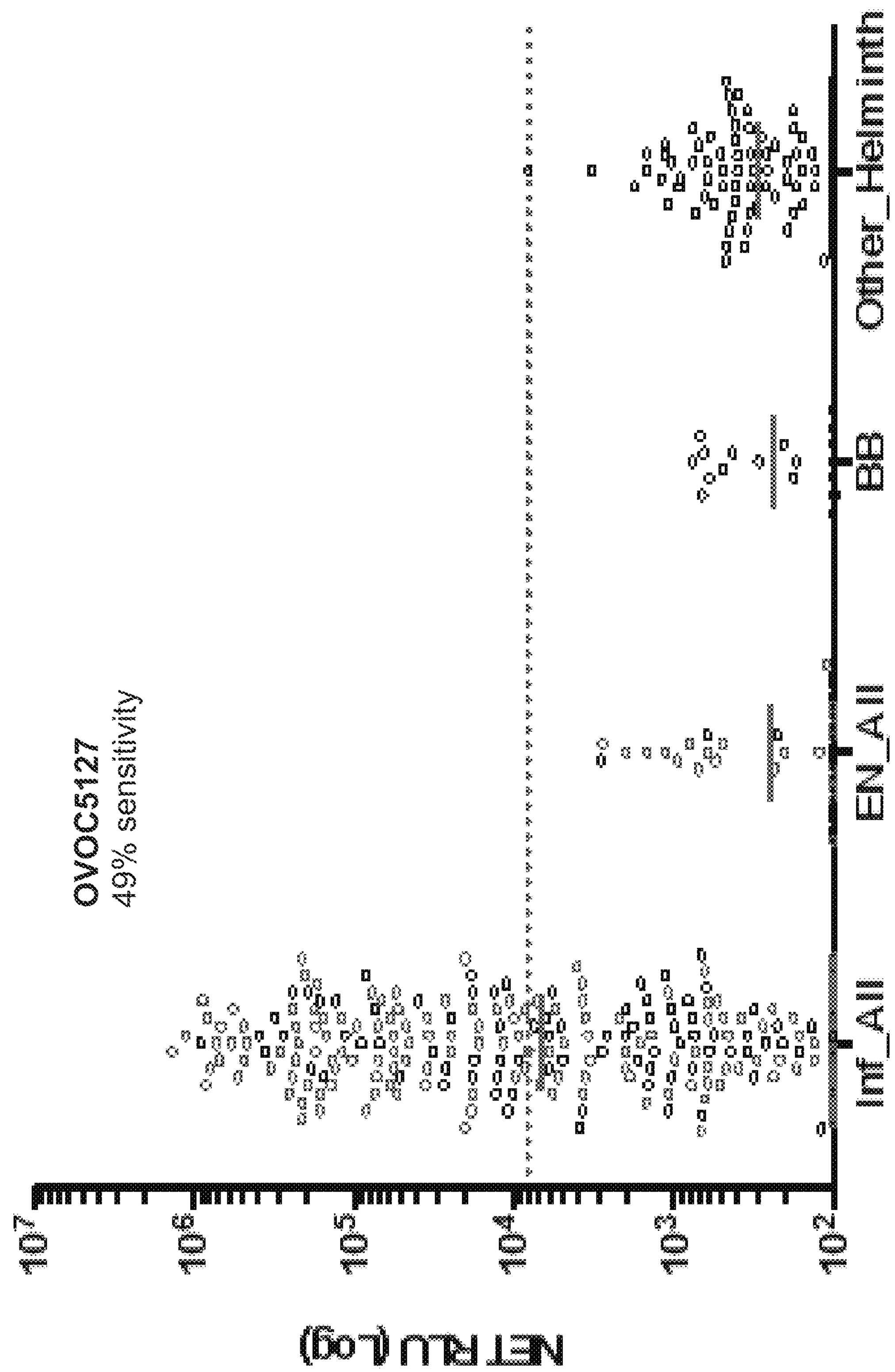
Figure 3E:
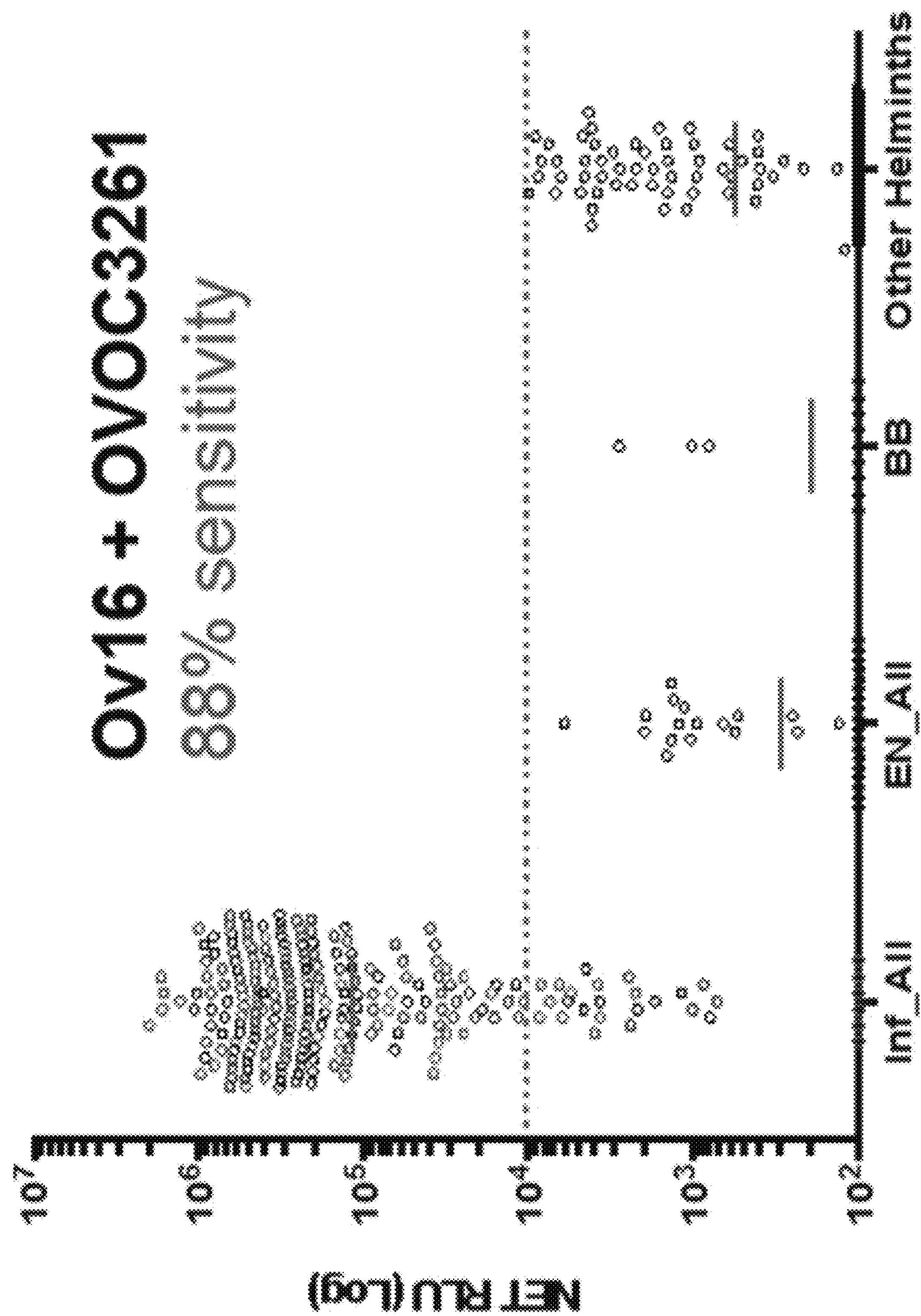
Figure 3F:
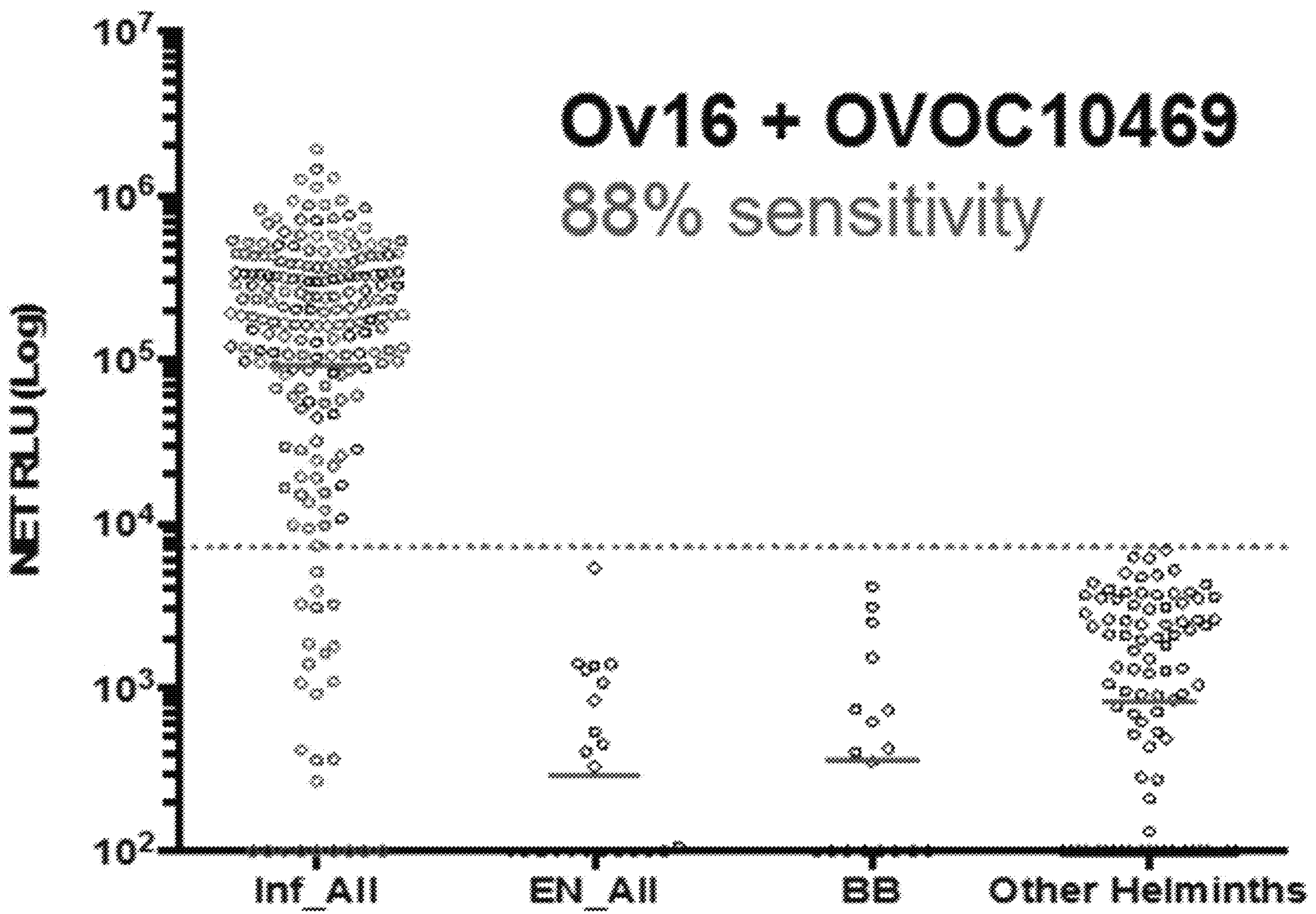
Figure 3G:
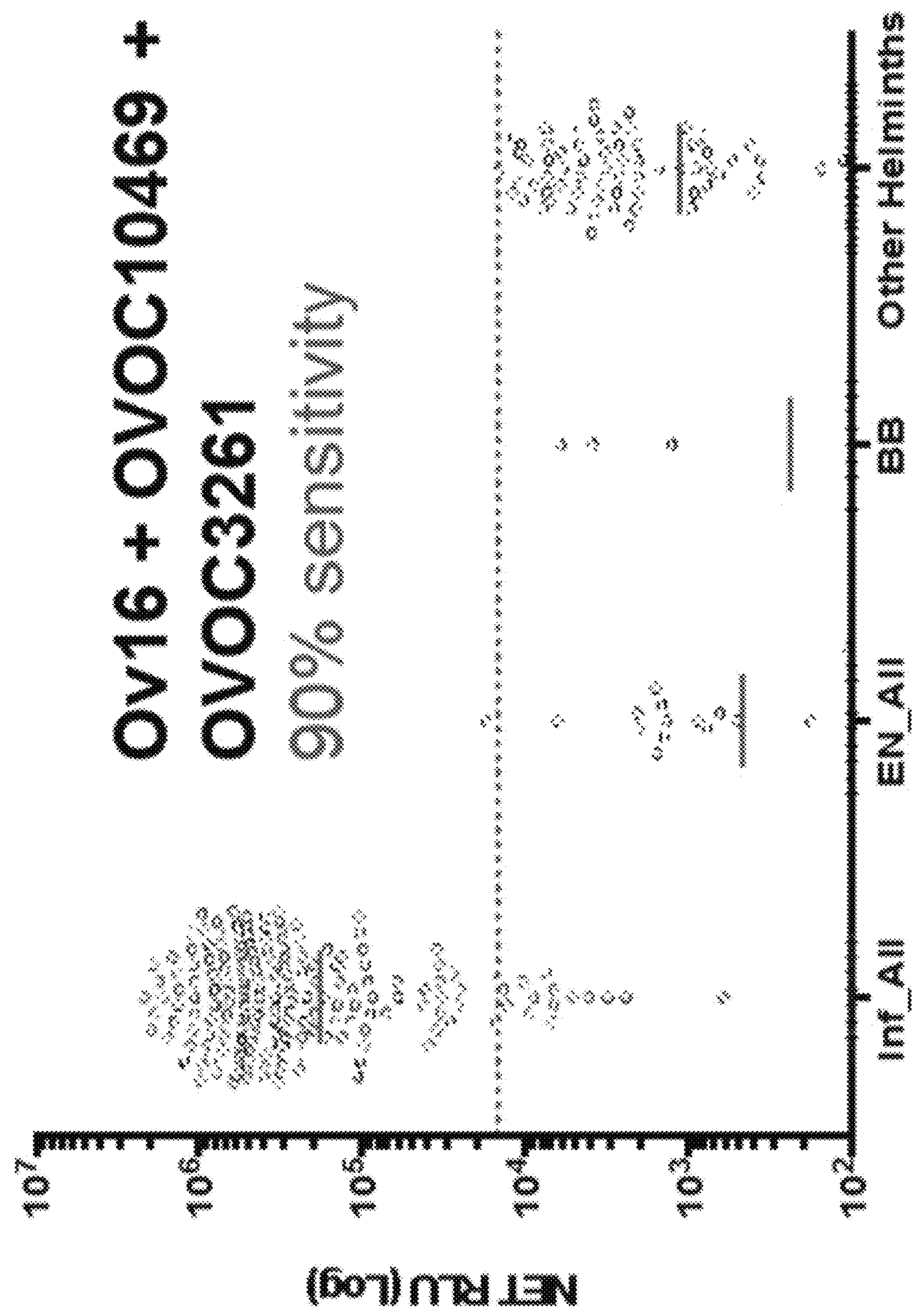
Figure 3H:
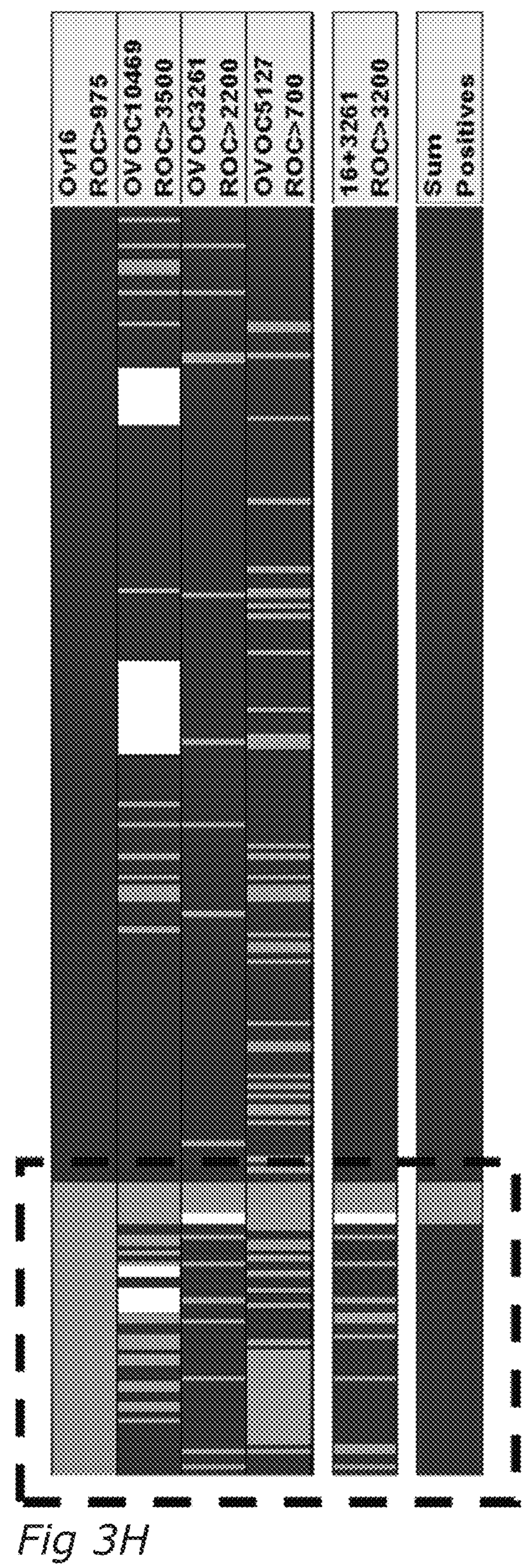

Among the biomarker sequences listed in Table 3, OVOC3261, OVOC5127 and OV10469 were tested for their individual immunoreactivity using a variety of *Onchocerca* microfilaria positive infected sera (truly infected) and a variety of control sera (non-infected (EN_all, BB), infected with unrelated human filarial pathogens or *S. stercoralis*) in immunoassays. As can be seen in FIG. 3, when using a cutoff that gave 100% specificity, OVOC10469 had 78% sensitivity (FIG. 3B), OVOC3261 had 78% sensitivity (FIG. 3C), and OVOC5127 had a sensitivity of 49% (FIG. 3D). Combinations of these newly identified proteins were tested in combination with the known Ov16 (KISAE-NANCKKCTPMLVDSAFKEHGIVPDWSTAPTKL VNVSYNNLTVNLGNELTPTQVKN QPTKVSWDAEP-GALYTLVMTDPDAPSRKNPVFREWHHWLIINIS-GQNVSSGTVLSDYIGSG PRKGTGLHRYVFLV YKQPGSITDTQHGGNRRNFKVMDFANKHHLGNPV AGNFFQAKHED; SEQ ID NO:63) (Table 6), it can be seen that the sensitivity increases for all of these combination compared to Ov16 alone. Each individual positive sera was tested against each of the antigens and in combination with all four. As can be seen in Table 6, the combination gets to 97 percent sensitivity (8/245 mf positives being false negatives).

TABLE 6

Reactivity of Ov-infected samples with *O. volvulus* biomarkers

| | Ov16 | OVOC10469 | OVOC3261 | OVOC5127 | Ov16 + OVOC3261 | Combination of 4 biomarkers |
|---|---|---|---|---|---|---|
| Positive | 187 (77%)* | 167 (81%) | 219 (91%) | 172 (70%) | 225 (94%) | 235 (97%) |
| Negative | 53 (23%) | 40 (19%) | 22 (9%) | 71 (29%) | 16 (6%) | 8 (3%) |
| Not tested | 2 | 38 | 4 | 2 | 4 | 2 |

*number of samples (percent of samples tested)

Further analysis demonstrated that OVOC3261, OVOC10469, OVOC8491, OVOC11950, OVOC10602 are microfilaria-specific. Moreover, most of these antigens are relatively invariant based on non-synonymous SNPs and that antibodies of the IgG and $IgG_4$ isotypes of two of these (OVOC3261 and OVOC10469) only appear after microfilariae appear in the skin of experimentally infected chimpanzees.

Example 6. Immunization of Mice with *O. volvulus* Proteins

Yeast codon optimized DNAs encoding for *O. volvulus* proteins Ov-CPI-2M (OVOC7453), Ov-103 (OVOC4230), and Ov-RAL-2 (OVOC9988), minus the signal peptides at the N-terminus, were synthesized and subsequently subcloned in-frame into the yeast expression vector pPinkα-HC (Life Technologies) with XhoI/KpnI sites and *E. coli* expression vector pET41a (EMDMillipore) with the fusion GST deleted (NdeI/XhoI). The correct open reading frame (ORF) was confirmed by double-stranded sequencing using the vector flanking primers (5'AOX1/CYC1 for pPinkα-HC and T7 promoter/T7 terminator for pET41a). For expression in yeast, the recombinant plasmids were linearized with AflII digestion and then transformed by electroporation into PichiaPink strain #4 with protease A and B knockout (pep4/prb1⁻) to prevent *P. pastoris*-derived protease degradation. Yeast transformants were selected on *P. pastoris* adenine dropout (PAD) selection plates. The expression of recombinant filarial antigens with hexahistidine (6His)-tag at the C-terminus was induced with methanol and the soluble recombinant proteins secreted into the culture were purified with immobilized metal ion affinity chromatography (IMAC). For expression in *E. coli*, the recombinant constructs cloned into pET41a were transformed into BL21 (DE3) (EMDMillipore) and recombinant proteins were induced with 1 mM isopropyl-β-thiogalactoside (IPTG) and purified with IMAC.

In order to test the synergistic protection of two or three *O. volvulus* protective antigen combinations, protective *O. volvulus* antigens Ov-103, Ov-RAL-2 and Ov-CPI-2M, were fused together as a triple antigen (Ov-103-RAL-2-CP12-M) or as two double antigens (Ov-103-RAL-2 and Ov-RAL-2-CP12-M) by using a flexible linker (KGPDV-PETNQQCPSNTGMTD; SEQ ID NO:50) obtained from Na-ASP-1 structure between two pathogenesis-related (RP) domains. The yeast codon optimized fusion DNAs were subcloned into either yeast expression vector pPICZαA (Life Technologies) or *E. coli* expression vector pET41a with GST knockout. The recombinant fusion proteins were expressed and purified using the same methods described above except for the use of yeast strain *P. pastoris* X-33.

TABLE 7

| SEQ ID NO. | Protein Description | Sequence |
|---|---|---|
| 64 | Ov-103-RAL2-CPI2M fusion protein | **DLLSEAGDFFTKHFTDIKSLFAKDEKQLQQSVDRVKDLLATIQDKMSMLQ**<br>**PLANDMQKTTLGKIGDLISQVNSFRETMSNPKMDFTNKENKWEELLKKIF**<br>**VTEGLNKVIPLLQKLKNSA**KGPDVPETNQQCPSNTGMTDPQRRQQQQQ<br>QQQQQQRDEREIPPFLEGAPPSVIDEFYNLLKTDENKTDQQTEADVEAFIN<br>RLGGSYKVRFTQFMEEVKKARADYERIHQQAVARFSPAAKDADARMSAIA<br>DSPHLTTRQKSQQIQAIMDSLSESVRREIINALSPQEKGPDVPETNQQCPS<br>NTGMTD*KNPSKMESKTGENQDRPVLLGGWEDRDPKDEEILELLPSILMKV*<br>*NEQSKDEYHLMPIKLLKVSSQVVAGVKYKMDVQVARSQCKKSSNEKVDLT*<br>*KCKKLEGHPEKVMTLEVWEKPWENFMRVEILGTKEV* |
| 65 | Ov103-RAL2 fusion protein | **DLLSEAGDFFTKHFTDIKSLFAKDEKQLQQSVDRVKDLLATIQDKMSMLQ**<br>**PLANDMQKTTLGKIGDLISQVNSFRETMSNPKMDFTNKENKWEELLKKIF**<br>**VTEGLNKVIPLLQKLKNSA**KGPDVPETNQQCPSNTGMTDPQRRQQQQQ<br>QQQQQQRDEREIPPFLEGAPPSVIDEFYNLLKTDENKTDQQTEADVEAFIN<br>RLGGSYKVRFTQFMEEVKKARADYERIHQQAVARFSPAAKDADARMSAIA<br>DSPHLTTRQKSQQIQAIMDSLSESVRREIINALSPQE |
| 66 | OvRAL2-CPI2M fusion protein | PQRRQQQQQQQQQQQRDEREIPPFLEGAPPSVIDEFYNLLKTDENKTDQ<br>QTEADVEAFINRLGGSYKVRFTQFMEEVKKARADYERIHQQAVARFSPAA<br>KDADARMSAIADSPHLTTRQKSQQIQAIMDSLSESVRREIINALSPQEKGPD<br>VPETNQQCPSNTGMTD*KNPSKMESKTGENQDRPVLLGGWEDRDPKDEEI*<br>*LELLPSILMKVNEQSKDEYHLMPIKLLKVSSQVVAGVKYKMDVQVARSQCK*<br>*KSSNEKVDLTKCKKLEGHPEKVMTLEVWEKPWENFMRVEILGTKEV* |

Ov103 sequence - Bold;
Linkers - Highlighted;
OvRAL2 sequence - underlined;
OVCPI-2M sequence - Italics.

The purity and the molecular weight of purified recombinant proteins were analyzed by SDS-PAGE using pre-cast 4-20% Tris-glycine gels (Life Technologies) and stained with Coomassie brilliant blue R-250 (Fisher Scientific).

Male BALB/cByJ mice were purchased from The Jackson Laboratory at 6-8 weeks of age. All mice were housed in micro-isolator boxes in a room that was pathogen-free and under temperature, humidity and light cycle controlled conditions. Mice were fed autoclavable rodent chow and given water ad libitum. All protocols using mice were approved by the Institutional Animal Care and Use Committee.

Mice were immunized with 25 μg of the produced vaccine antigens (Ov-CPI-2M, Ov-103, or Ov-RAL-2, or the two- or three-antigen fusion proteins) in 0.1 ml of Tris-buffered saline (TBS) formulated with 0.1 ml of 1:5 Rehydragel LV (alum) in PBS (General Chemical). Mice were immunized s.c. in the nape of the neck, followed by two booster injections 14 and 28 days later.

The mice were challenged 14 days after the final booster as previously described (Hess et al., Int. J. Parasitology 44:637-646, 2014) with 25 L3 larvae delivered within a diffusion chamber. The diffusion chambers were implanted in a s.c. pocket on a rear flank of each mouse. Recovery of the chambers was performed 21 days later and larval survival was determined based on mobility and morphology of the remaining larvae. Protective immunity was calculated in two ways: (i) percentage of reduction in larvae was calculated as follows: reduction=((average worm survival in control mice−average worm survival in immunized mice)÷average worm survival in control mice)×100; and (ii) host protection was calculated as follows: (number of immunized mice with parasite recovery levels below the lower S.D. of parasite recovery in control mice÷total number of immunized mice)×100). Host cells within the diffusion chamber were collected and analyzed by centrifugation onto slides using a Cytospin 3 (Shandon Inc.) and then stained for differential cell counts using Hemastain 3 (Fisher Scientific).

Serum was collected at the time of recovery for antigen-specific IgG analysis. Maxisorp 96-well plates (Nunc Nalgene) were coated with 2 μg/ml of the immunizing recombinant antigen in 50 mM Tris-CI coating buffer, pH 8.8, overnight at 4° C. Plates were washed with deionized water between each step. Plates were blocked with borate buffer solution (BBS) (0.17 M boric acid, 0.12 M NaCl, 0.5% TWEEN 20, 0.025% BSA, 1 mM EDTA, pH 8.2) at room temperature for 30 min. Individual sera were diluted to an appropriate starting concentration with BBS and serially diluted; plates were sealed and incubated at 4° C. overnight. Biotinylated IgG (eBioscience) was diluted 1:250 in BBS and incubated for 1 hr at room temperature, followed by ExtrAvidin Px (Sigma) which was diluted 1:1000 in BBS and incubated for 30 min at room temperature. One component ABTS peroxidase substrate (KPL) was added and O.D.s were read after 30 min at 405 nm in a Bio-Rad iMark Microplate reader (Bio-Rad). ELISA data are presented as endpoint titers which were calculated as the serum dilution from experimental animals that had an O.D. reading three times higher than the O.D. recorded for control serum.

*Onchocerca volvulus* proteins were expressed as soluble recombinant proteins in high yield in *P. pastoris* and *E. coli* BL21(DE3) after being induced with 0.5% methanol for *P. pastoris* and 1 mM IPTG for *E. coli*, and purified with IMAC. Purified recombinant Ov-103, Ov-RAL-2 and Ov-CPI-2M expressed in *P. pastoris* or in *E. coli* migrated at the same molecular mass as calculated by the coding sequence (14.5 kDa, 17.9 kDa and 16.0 kDa, respectively) on SDS-PAGE and Coomassie staining. The fusion recombinant proteins of two or three antigen combination (Ov-103-RAL2, Ov-RAL2-CP12M and Ov-103-RAL2-CP12M) were also expressed in *P. pastoris* and *E. coli* expression systems as soluble proteins and the purified recombinant fusions were shown at the correct molecular weight as estimated by sequences on SDS-PAGE (50.6 kDa, 32.5 kDa and 35.2 kDa, respectively).

Figure 4A:
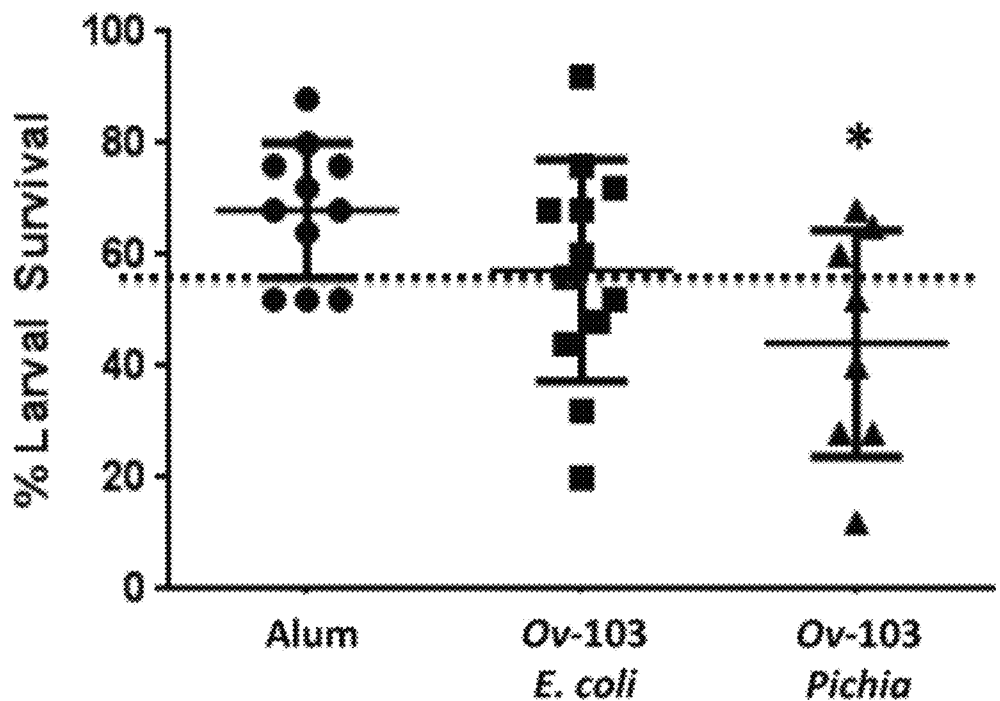
FIG. 4A-C depicts the effect of immunization with a single vaccine antigen expressed by either *Escherichia coli* or *Pichia pastoris* on the development of protective immunity to *O. volvulus* larvae in mice.
Figure 4B:
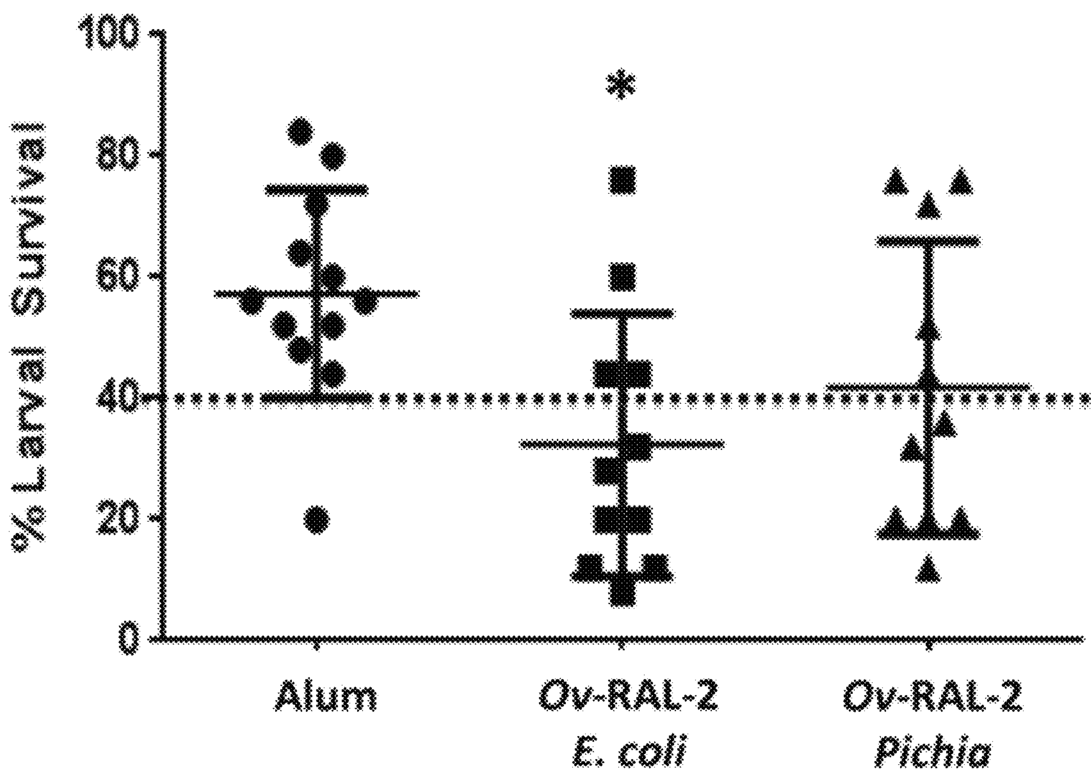
Figure 4C:
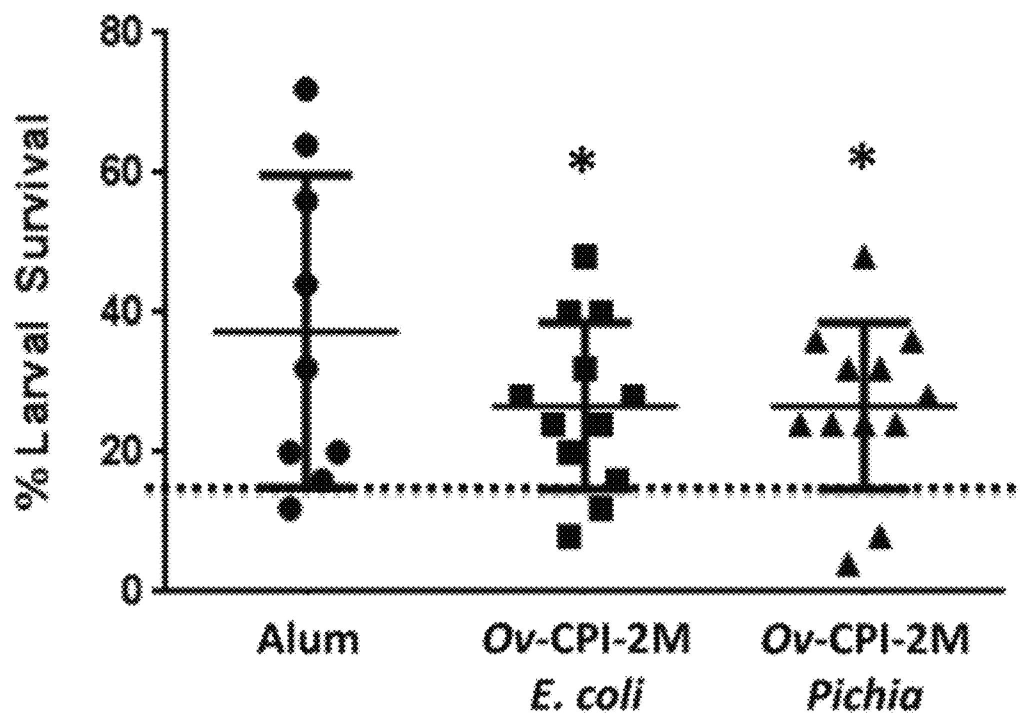

Immunization of mice with Ov-CPI-2M expressed in both *E. coli* and *P. pastoris* induced statistically significant reductions of 30% in larval survival and 17% levels of host protection (FIG. 4C). As with the other two antigens, differential cell counts showed comparable numbers of total and specific cells in the control and immunized mice, and parasite-specific antibody titers had equivalent endpoints (Table 8). There were no significant correlations between antibody endpoint titers and parasite survival.

TABLE 8

Geometric mean of IgG endpoint titers following immunization with individual, fusion, or concurrent antigen formulations.

| | Endpoint titer to antigen | | | | | |
|---|---|---|---|---|---|---|
| Immunizing Antigen | Ov-103 | Ov-RAL-2 | Ov-CPI-2M | Ov-RAL-2/103 | Ov-RAL-2/CPI-2M | Ov-RAL-2/103/CPI-2M |
| Ov-103 *E. coli* | 33,064 | | | | | |
| Ov-103 *P. pastoris* | 35,882 | | | | | |
| Ov-RAL-2 *E. coli* | | 571,055 | | | | |
| Ov--RAL-2 *P. pastoris* | | 519,490 | | | | |
| Ov-CPI-2M *E. coli* | | | 431,803 | | | |
| Ov-CPI-2M *P. pastoris* | | | 462,057 | | | |
| Ov-103/RAL-2 fusion | 317,320 | 439,250 | | 1,509,278 | | |
| Ov-RAL-2/CPI-2M fusion | | 187,884 | 266,079 | | 691,063 | |
| Ov-RAL-2/103/CPI-2M fusion | 90,464 | 146,607 | 165,510 | | | 1,112,542 |
| OV-RAL-2, 103, CPI-2M concurrent | 16,019 | 271,416 | 392,676 | | | |

In BALB/cByJ mice immunized with Ov-103 with alum prepared in both *P. pastoris* and *E. coli* expression systems, *E. coli*-expressed protein induced an 8% reduction in larval survival and a 50% level of host protection, whereas mice immunized with the *P. pastoris*-expressed protein had a statistically significant 30% reduction in parasite survival and a 63% level of host protection (FIG. 4A). Differential cell counts were performed at the conclusion of the experiments on the diffusion chamber contents. Comparable numbers of total cells ($1.4\times10^6\pm1.3\times10^6$), and percentages of lymphocytes (5±7%), neutrophils (52±20%), macrophages (37±15%) and eosinophils (12±14%) were seen in the control and immunized mice. Parasite-specific antibody titers show equivalent endpoint titers for mice immunized with *P. pastoris* and *E. coli* expressed Ov-103 when measured against both the *P. pastoris* and *E. coli* expressed proteins (Table 8). Correlation analyses were performed between parasite survival and antibody endpoints titers and there were no significant relationships between the amount of antibody produced and the survival of the larvae.

Mice immunized with *E. coli*-expressed Ov-RAL-2 induced a statistically significant 39% reduction in larval survival and a 64% level of host protection, whereas mice immunized with the *P. pastoris*-expressed protein induced a 24% reduction in parasite survival and a 55% level of host protection (FIG. 4B). As with Ov-103, differential cell counts showed comparable numbers of total cells, lymphocytes, neutrophils, macrophages and eosinophils in the control and immunized mice. Parasite-specific antibody titers show equivalent endpoint titers for both the *P. pastoris* and *E. coli* expressed proteins (Table 8). Again, correlations between parasite survival and antibody endpoints titers did not reveal any significant relationship between the amount of antibody produced and parasite survival.

Figure 5A:
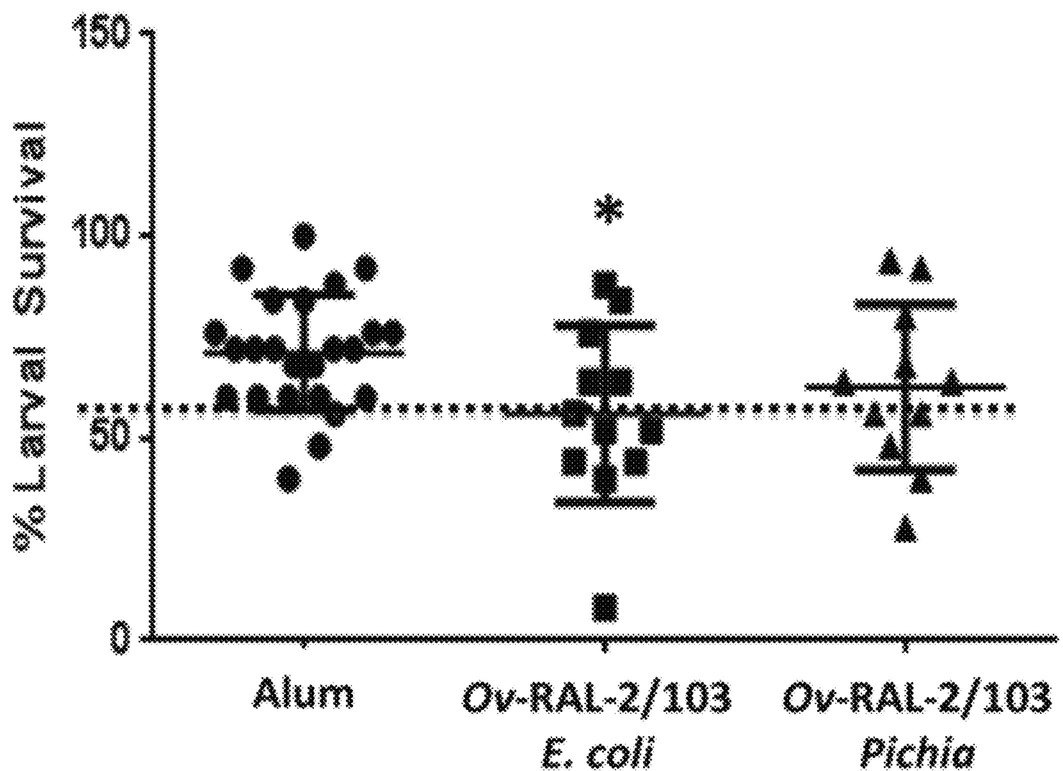
FIG. 5A-B depicts the effect of immunization with fusion antigens on the development of protective immunity to *O. volvulus* larvae in mice.
Figure 5B:
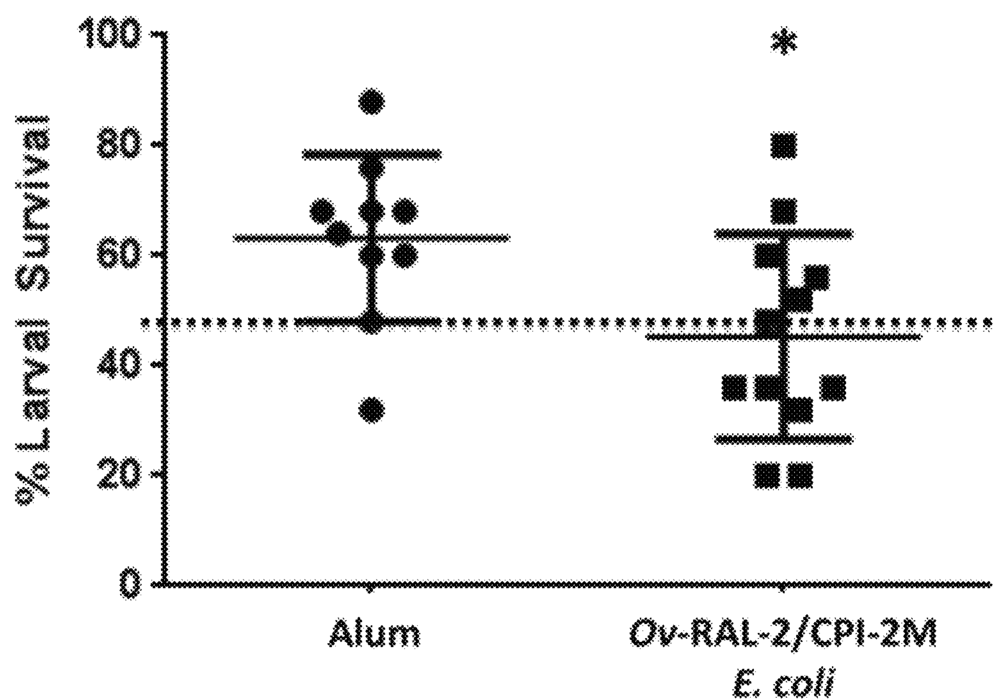
Figure 6:
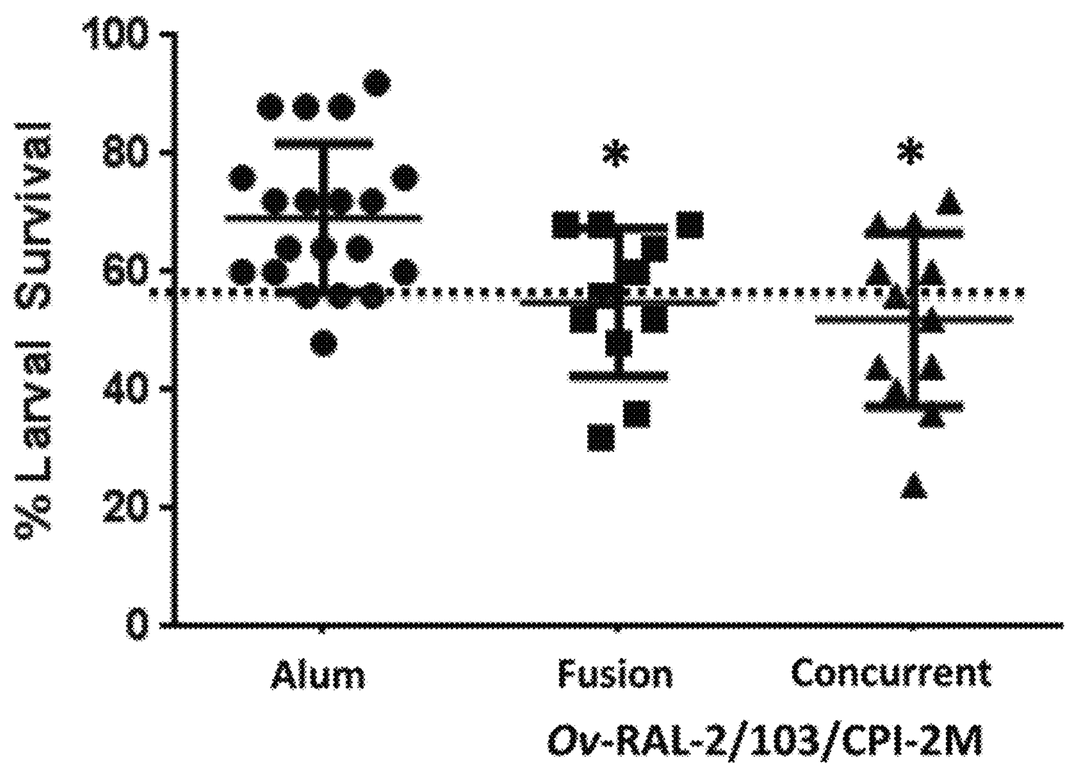
FIG. 6 depicts the comparative effect of immunization with concurrent injections of *O. volvulus* Ov-103 (expressed in *P. pastoris*), Ov-RAL-2 (expressed in *E. coli*) and Ov-CPI-2M (expressed in *E. coli*) compared with immunization with the combined fusion antigen Ov-RAL-2/103/CPI-2M (expressed in *E. coli*). Each dot represents larval recovery from an individual animal. Data presented are mean±S.D. Asterisk represents statistical difference in larval recoveries; $P \leq 0.05$.

In mice immunized with Ov-RAL-2/103 fusion protein expressed in *P. pastoris* and *E. coli, E. coli*-expressed protein significantly reduced larval survival by 21% and provided a 58% level of host protection, whereas immunization with *P. pastoris*-expressed protein only reduced larval survival by 11% and provided a 45% level of host protection (FIG. 5A). Immunization with Ov-RAL-2/CPI-2M *E. coli* fusion protein induced protective immunity with parasite reduction at 34% and a 50% level of host protection (FIG. 5B). Analysis of the cells within the diffusion chamber contents showed similar numbers of total cells, lymphocytes, neutrophils, macrophages and eosinophils. Parasite-specific antibody titer endpoints were measured against the individual antigens and the fusion protein. Antibody endpoint titers for the two fusion proteins were significantly higher than the antibody responses in these mice to the individual antigens of which the fusion was composed. The antibody response to Ov-RAL-2 and Ov-CPI-2M by mice immunized with these antigens as part of a fusion were equivalent to the responses seen in mice immunized with antigen individually. However, the parasite-specific antibody titer endpoint to Ov-103 was approximately eight-fold higher in mice immunized with the antigen as part of a fusion compared with immunization with the individual antigen (Table 8). Once again, there were no significant correlations between antibody endpoints and parasite survival.

A fusion protein consisting of Ov-103, Ov-RAL-2 and Ov-CPI-2M was created to determine whether enhanced protective immunity would be achieved with this triple fused antigen. The Ov-RAL-2/103/CPI-2M *E. coli* fusion was tested in comparison with concurrent immunization consisting of the three antigens injected simultaneously but at different locations on the mice. Immunization with the three-antigen fusion protein and the concurrent immunization resulted in significant levels of protective immunity, with the fusion inducing a 20% reduction in larval survival and a 45% level of host protection and the concurrent immunization resulting in a 25% reduction in parasite survival and a 64% level of host protection (FIG. 7). Analysis of the cells within the diffusion chamber contents showed similar numbers of total cells, lymphocytes neutrophils, macrophages and eosinophils. Antibody titer endpoints were measured against the individual antigens and the fusion protein. Mice immunized with the three antigens concurrently had antibody endpoint titers to the three antigens that were comparable with those seen in mice immunized with the three individual antigens (Table 8). Mice immunized with the three-antigen fusion protein had endpoint titers to the single antigens that were comparable with the titers seen in mice immunized with individual antigens. Antibody endpoint titers for the three-antigen fusion protein were significantly higher than the antibody responses in these mice to the individual antigens of which the fusion was composed (Table 8). There were no significant correlations between antibody endpoints and parasite survival.

Example 7. Orthologs of *O. volvulus* Proteins Induce Protective Immunity to Other Filarial Parasites

*Brugia malayi* is a filarial parasite, one of the three causative agents of lymphatic filariasis in humans. Lymphatic filariasis, also known as elephantiasis, is a condition characterized by swelling of the lower limbs. The *B. malayi* Bm-103 and Bm-RAL-2 proteins are orthologous to *volvulus* Ov-103 and Ov-RAL-2 which are candidates for development of an *O. volvulus* immunogenic composition (Table 9). The *B. malayi* gerbil model was used to confirm the efficacy of these *O. volvulus* orthologs, alone or in combination, against adult worms. Efficacy of recombinant Bm-103 and Bm-RAL-2 administered individually, concurrently, or as a fusion protein were tested in gerbils using alum as adjuvant. Immunization with Bm-103 resulted in worm reductions of 39%, 34%, and 22% on 42, 120 and 150 days post infection (dpi), respectively, and immunization with Bm-RAL-2 resulted in worm reductions of 42%, 22%, and 46% on 42, 120, and 150 dpi, respectively. Immunization with a fusion protein comprised of Bm-103 and Bm-RAL-2 resulted in improved efficacy with significant reduction of worm burden of 51% and 49% at 90 dpi, as did the concurrent immunization with Bm-103 and Bm-RAL-2, with worm reduction of 61% and 56% at 90 dpi. Immunization with Bm-103 and Bm-RAL-2 as a fusion protein or concurrently not only induced a significant worm reduction of 61% and 42%, respectively, at 150 dpi, but also significantly reduced the fecundity of female worms as determined by embryograms. Elevated levels of antigen-specific IgG were observed in all immunized gerbils. Serum from gerbils immunized with Bm-103 and Bm-RAL-2 individually, concurrently, or as a fusion protein killed third stage larvae in vitro when combined with peritoneal exudate cells.

Thus, immunization with Bm-103 and Bm-RAL-2 individually conferred protection against *B. malayi* infection in gerbils.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for determining whether a subject has been infected with *Onchocerca volvulus*, comprising identifying in a specimen from the subject antibodies to *O. volvulus* filarial proteins Ov16 (SEQ ID NO:63) and OVOC3261 (SEQ ID NO:4), or an immunoreactive fragment thereof, and optionally one or more of OVOC10469 (SEQ ID NO:1), OVOC11950 (SEQ ID NO:2), OVOC10602 (SEQ ID NO:3), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC10384 (SEQ ID NO:13), OVOC8422 (SEQ ID NO:14), OVOC9988 (SEQ ID NO:31), and OVOC6395 (SEQ ID NO:15), or an immunoreactive fragment thereof, wherein presence of antibodies to at least Ov16 and OVOC3261 in the specimen from the subject indicates that the subject has been infected with *O. volvulus*.

2. The method of claim 1, wherein the specimen comprises blood or urine.

3. The method of claim 1, wherein the immunoreactive fragment comprises the amino acid sequence of OVOC10469_Pep2 (SEQ ID NO:51), OVOC3261_Pep1 (SEQ ID NO:52), OVOC3261_Pep3 (SEQ ID NO:53), OVOC10469_Pep1 (SEQ ID NO:54), OVOC10469_Pep3 (SEQ ID NO:55), OVOC3261_Pep2 (SEQ ID NO:56), OVOC5127_Pep1 (SEQ ID NO:57), OVOC5127_Pep2 (SEQ ID NO:58), OVOC5127_Pep4, (SEQ ID NO:59), OVOC5127_Pep5 (SEQ ID NO:60), or OVOC5127_PepX (SEQ ID NO:61).

4. The method of claim 1, comprising identifying in the specimen from the subject antibodies to *O. volvulus* filarial proteins Ov16 and OVOC3261, or an immunogenic fragment thereof, and one or more *O. volvulus* filarial protein selected from OVOC10469, OVOC5127, OVOC9988, and OVOC4230, or an immunogenic fragment thereof.

5. The method of claim 1, comprising identifying in the specimen from the subject antibodies to *O. volvulus* filarial proteins Ov16, OVOC3261, OVOC10469, and OVOC5127, or an immunogenic fragment thereof.

6. The method of claim 1, wherein the antibodies to the *O. volvulus* filarial proteins are detected by a method selected from the group consisting of ELISA, dipstick tests, lateral flow, microfluidic devices, luciferase immunoprecipitation systems, luminex, multiplex-formats, and microarrays.

* * * * *

SEQUENCE LISTING

```
Sequence total quantity: 66
SEQ ID NO: 1            moltype = AA  length = 98
FEATURE                 Location/Qualifiers
source                  1..98
                        mol_type = protein
                        organism = unidentified
SEQUENCE: 1
NIAFAPNPKD SNNELFADAE SALGSEYAQF VEQSKQHKPV YFSDNQNTLE TIKLESIPNP  60
ETETAYPMFI CGFLGCMKKM NSVEEYLEHF KMHEKQGY                          98

SEQ ID NO: 2            moltype = AA  length = 103
FEATURE                 Location/Qualifiers
source                  1..103
                        mol_type = protein
                        organism = unidentified
SEQUENCE: 2
YPTEKETVEP IDTMVKDDID LVKAEVAEAE EADVEKEVAE LTEEEAAEIA EVLDEMEEEF  60
FAFLLFDFIL DLFRETLEKN SESQEASIDE VMPEIQGVSA EEA                    103

SEQ ID NO: 3            moltype = AA  length = 119
FEATURE                 Location/Qualifiers
source                  1..119
                        mol_type = protein
                        organism = unidentified
SEQUENCE: 3
FRTQSIGIRG RLMCGSKPAS NERIKLWEED SDDLLDQGYT DENGEFLLKG DTVELTPIDP  60
VFKVYHDCDD GIKPGKRKVK FKIPKSYITE GKTPKKIFDL GTLNLETIFN DEERELIVT   119

SEQ ID NO: 4            moltype = AA  length = 149
FEATURE                 Location/Qualifiers
source                  1..149
                        mol_type = protein
                        organism = unidentified
SEQUENCE: 4
SYCEDWDPED FPSFVLKLSQ NATEEFCELY EMEMEVPINK FYDMLRKWAE KYSVQAETNR  60
FIAEEMNYDK MQSKVLMERL QASNGTTEVK GVLEKALKLQ ESMHLSPDYI QNVIDTMMEN  120
LPIDKQNEAT LLWNSLYPDD IYNECGPRF                                    149

SEQ ID NO: 5            moltype = AA  length = 426
FEATURE                 Location/Qualifiers
source                  1..426
                        mol_type = protein
                        organism = unidentified
SEQUENCE: 5
APPNRDTADD LQNADMQRQW EQEQRQREEV QKEEIAKYVK YMRYLETVLN ILQATPQWKE  60
AMQSMTQEEM RGGKIAEMVD KLEPHIIEQL AKAKILELQR LEQEIKDQLN ADGGATHNIK  120
VSEILTVCLK EGFKKPSNLG IPEHLDFNNW ETFSQEDLRK LIVKIVTDMD ELEEQRKQDF  180
KQYEMKKKAE EDHKMQAKMI QTEREEYIRQ MEEQRRRHNK HEPLKHPGSR NQLRKVWEDT  240
DKLDKDAYDP TTLFGLHDRN NDGYWSYDEL NTIFLPEIEK LNNFSDVERL EELYRMRDHV  300
MKQMDTDGDH RISRAEFLAD REAQEEKPDQ GWEDIGDKDQ YTKEELEIFE KEYAKQQGWG  360
EYAYSTPAPT PDPSRMIQPD QAPMQRLDAP SDQVGDMFAQ QSHQIPVKHV EPIQSVQQQQ  420
MDEVNS                                                             426

SEQ ID NO: 6            moltype = AA  length = 231
FEATURE                 Location/Qualifiers
source                  1..231
                        mol_type = protein
                        organism = unidentified
SEQUENCE: 6
FPTEANPAVG TDNAHEDNLT TEEKMQLKKF AKTNAANFSL TDPEFIDGLK NEAAGLFSKL  60
TGLRDIINAK LDTMQPESRL FIEKLLRRFL AAFSHDGLMN ILESLKGFGK EVIDMFDGLS  120
RPIQNDILNA FPLVGSYITS DIARLMLRKL AELDLLSRKS TLTPTVDQFN DDSGKHFPRP  180
QVIEPEEPEN SDPEDAQSTD YGKKKVVTTT TFPIITGEED EILVKKIVEN K            231

SEQ ID NO: 7            moltype = AA  length = 83
FEATURE                 Location/Qualifiers
```

```
source                  1..83
                        mol_type = protein
                        organism = unidentified
SEQUENCE: 7
IPLPEELDYD GEIPNCRDGE KPLLAADIGV YTCDKNCPKG FRCEYRTMDS TSKKGICCPN  60
LKELAKIYSE DEEVDKSIKK SNI                                          83

SEQ ID NO: 8            moltype = AA  length = 209
FEATURE                 Location/Qualifiers
source                  1..209
                        mol_type = protein
                        organism = unidentified
SEQUENCE: 8
MISCFALPFP HVCYMAYCTQ VIASIMKGWN QNFRFSTVIY LFRNIFSSSV ISCVNMILSS  60
TFYALLFVSA VVIVEAMPAS ESTYSVIIIR INDTTCKIED GVVSVNGQVI GNLTEEQKEE  120
LEAYNVQTQG WFQQLHQKIE ELFKTFFGSI KSMWKHSPIS GSESSPQSST PDNIITDKLD  180
DQDRRLKDQG DSENSSLFGL KLPSFCKVN                                    209

SEQ ID NO: 9            moltype = AA  length = 128
FEATURE                 Location/Qualifiers
source                  1..128
                        mol_type = protein
                        organism = unidentified
SEQUENCE: 9
FRSLKIGRKQ STAVKGVLTC NGKPAVNVKV KLYNDSQGRY VENSMDEGKT DSEGRFLLQG  60
HETSITSIDP ILKLYHNCDV ENAQCLKRFS ILIPNDFVSE GLEPKKTFDM GTLNLGGKFF  120
DEGRECAS                                                           128

SEQ ID NO: 10           moltype = AA  length = 256
FEATURE                 Location/Qualifiers
source                  1..256
                        mol_type = protein
                        organism = unidentified
SEQUENCE: 10
QIIGSFNGNY AGDGSLNNNA NSFGERTTTT RSTSRPSLPP RPGYPSRPGY PFKPGFPPRG  60
PPIPYPHGKP SGPRYPCYGG YGGYGHPGYG PFGGNGYLGY TVCSGRGEFG GYGPGLGGGT  120
GLGGLGPGEF GGYGPGLGGG TGLGGLGPGG FGGIGPGLGG GGGLGGPGRG GFAGYGPGLG  180
GGRGLGGPGP GGFDGYGPGL GGRPYPGGYG RFYGPGPYPG DRLDPRGLSE SGRPRTRLAS  240
YNRNDRGTQF SYIRDR                                                  256

SEQ ID NO: 11           moltype = AA  length = 280
FEATURE                 Location/Qualifiers
source                  1..280
                        mol_type = protein
                        organism = unidentified
SEQUENCE: 11
MTNEYETNYP VPYRSKLTES FEPGQTLLVK GKTAEDSVRF TINLHNTSAD FSGNDVPLHI  60
SVRFDEGKIV FNTFSKGEWG KEERKSNPYK KGDDIDIRIR AHDSKYTIYV DQKEVKEYEH  120
RVPLSSVTHF SIDGDVLVTY IHWGGKYYPV PYESGLSGEG LVPGKSLLIF ATPEKKGKRF  180
HINLLKKNGD IALHFNPRFD EKAIVRNSLI AGEWGNEERE GKMILEKGIG FDLEIKNEEY  240
AFQIFINGER YATYAHRLDP REINGLQIGG DLEVSGIQMR                        280

SEQ ID NO: 12           moltype = AA  length = 141
FEATURE                 Location/Qualifiers
source                  1..141
                        mol_type = protein
                        organism = unidentified
SEQUENCE: 12
DLLSEAGDFF TKHFTDIKSL FAKDEKQLQQ SVDRVKDLLA TIQDKMSMLQ PLANDMQKTT  60
LGKIGDLISQ VNSFRETMSN PKMDFTNKEN KWEELLKKIF VTEGLNKVIP LLQKLKNSAP  120
TTFATYLFTC IVPVLINTLR E                                            141

SEQ ID NO: 13           moltype = AA  length = 114
FEATURE                 Location/Qualifiers
source                  1..114
                        mol_type = protein
                        organism = unidentified
SEQUENCE: 13
MARINRLNFL LCIVHANITS APNPKDSNDE LFADAESALG SEYAQFVEQS KQHKPVYFSD  60
NQNTLETIKL ESIPNPETET AYPMFICGFL GCMKKMNSVE EYLEHFKMHE KQGY        114

SEQ ID NO: 14           moltype = AA  length = 69
FEATURE                 Location/Qualifiers
source                  1..69
                        mol_type = protein
                        organism = unidentified
SEQUENCE: 14
FSWKFGERLD EPVLMLRDLR AKEISPPSYM KRFESDTNEQ LLRYILHPKM LRRHDLSNAL  60
FYQPLWKMR                                                          69
```

```
SEQ ID NO: 15          moltype = AA  length = 278
FEATURE                Location/Qualifiers
source                 1..278
                       mol_type = protein
                       organism = unidentified
SEQUENCE: 15
MEGSPIKETR GLEATPVFEM VRSATLTFLL AVSTVLVVSR PNVLLPPKLP WDSDWRQKPP  60
PFPPEPPPEF KGILPPEIFA KLTAIHQDQS LTIPQKIVKI EEIMNSLPED VLQRLPLPPV  120
FRLLPQNVQE MIKTVRTTKN LTMEEKWLQM IILIESLPKQ QHRLLQQMLP KFSLGPLPDF  180
QDIIPKEDWD KLTAVYQDTN LDNIEKLRRV DEIIDALPDS IRQKIPLSPP FQKLPDHIQQ  240
QLQIIHTERG LTTEQRFRKM KAIIESLPWD MKKLMFQP                          278

SEQ ID NO: 16          moltype = AA  length = 425
FEATURE                Location/Qualifiers
source                 1..425
                       mol_type = protein
                       organism = unidentified
SEQUENCE: 16
LIKVFPEISA NMSVMFANSR SNQANNGYLV EFKAGRSNLQ AGSTVDRRKV VADKTKGLVF  60
IKQSSDQLMH FCWKNRETGA VVDDLIIFPG DTEFLRVREC TDGRVYMLKF KSTDEKRLFW  120
MQDGKTDKDD ENCKKVNETL NNPPAPRAAA RGGADRADVS SFGTLAALGS AGAESELGAL  180
GNLDQSQLMQ LLSLMNHTNS TSASEATNLL PQLPLVADTS HPMTSEDSGT TSTHGATPSN  240
TPANGIVADS SSNNAMQLSQ LKEIIASITP PDGSGRKPSI DFTDVLCCAD KINDVLRKYA  300
EQLIPHLPSQ EPIYNNQEEL QQTLRTPQFR QAADIFGHAL QTGQLAPVLR QFGIDGNTAT  360
AAGNGDMVAW AAQFTTAENG KEITAKTETS PSQPGMESDV EDEETNEKAI RETEKNRTDD  420
HMDLD                                                              425

SEQ ID NO: 17          moltype = AA  length = 90
FEATURE                Location/Qualifiers
source                 1..90
                       mol_type = protein
                       organism = unidentified
SEQUENCE: 17
MNYKAPIELQ QLLSITKMLS LSVLLLFTSM AIMARPPNSD EIKELRQQQL NESKDDYDTL  60
PDVNHIPESF KESLKKQKML YLDMLRQHNL                                  90

SEQ ID NO: 18          moltype = AA  length = 257
FEATURE                Location/Qualifiers
source                 1..257
                       mol_type = protein
                       organism = unidentified
SEQUENCE: 18
LSVPAGLRPA KKVGDPKEQI VPGKQQQLQQ QQQQQLLQQQ QQQQQQQQQQ QQQQQQQQQQ  60
QQQQQQQEQQ EELQQLQESE ETGEEHRQQQ QQQHDEALTL SPTPKVPPNL SIRSRMMAAL  120
SASVGESNKE KNSSNDETDN SSKSTNSPSK PPIIFPKANK KTVVGKIAPS GISKGSARVI  180
VAPPSKLGTN NFGLNTVLQT NLVDSRGRIM KNVNSVPIKV PSSAEMRNAR TRHTARQVES  240
DADKVVPIKF GSTSRRR                                                 257

SEQ ID NO: 19          moltype = AA  length = 130
FEATURE                Location/Qualifiers
source                 1..130
                       mol_type = protein
                       organism = unidentified
SEQUENCE: 19
NNSNLDISMR EKNAVNAIEK QDLPRSHRFK RQYSCGQCGG GGGPPVVVSP CQQCKGGGAG  60
VSAIGGAGGI SAIGGGVSAI GGGFGGGGGD TVAVVCCGAT GLKGMFRNWW LHIPLLLLPM  120
SMSWIKALFL                                                         130

SEQ ID NO: 20          moltype = AA  length = 185
FEATURE                Location/Qualifiers
source                 1..185
                       mol_type = protein
                       organism = unidentified
SEQUENCE: 20
YYVPDNYWPL RIIGYHHIPV MINMWYLFQT EISNIGVDAV LVQSPLYRTL TPDVVHDIIS  60
INVEPNHTVV VEQSNPMLQA SSVEQAPAAA PLSITLIAPG ITISRTHKVD TYKSTMEMYD  120
ADKLHSNEIF KRRVRKMVLP PSRGEEVRKP PSSTDGYESE NVESYGQKGV EQAPPEIEQY  180
VKKKK                                                              185

SEQ ID NO: 21          moltype = AA  length = 633
FEATURE                Location/Qualifiers
source                 1..633
                       mol_type = protein
                       organism = unidentified
SEQUENCE: 21
MKYCLSSIIA ATIATTTTA TAIIATTITA ATISVAPFHA SSPSSSLSSS SFSSFFLVLP  60
LITTILLIVP EQAHSTATVT EHRSPPDLSI PSQTEFRVPV GTKQFRLICP VKEKNDDLLM  120
IQWKKNDEPI GFDFNNRFKL ARSDRELKIR NPQLSDGGIY QCQVVNGFGH RELNFTVTFY  180
```

```
DPAMENDQNT DSTLTLTTKA SPPIWKNETE IRNWMINPVR ITIGGALLLK CPAKGNPLPH  240
ITWLRDGKVL EREITYHYSS AILYLSDVQP SEGGKYICKL ENEHGSIEAS FHVYVENFFE  300
GLDGESWSID QTNAQLYPVI DEPFNNTVRV GRTAQFQCKV KNQQQPLIKW LKRVEDPNAI  360
RQTNANATLI HANNMHLLLL EKPETSAELS DGISLNRLII PNVRYEHSGT YLCVVTNARG  420
DIAYRSAYLN VIARSDHGEL SNLYFYGGLL VLIVVFTLIT YAVHFLRKNQ AAKSTESAPG  480
ITNIRYSFSL RPPPPNLPPP KAPALPSERQ QLMPNNQPCD RYTVNSAAAT YYPQFATPDK  540
KLQKIITESG TRPTPIRRTN GGDTKYRLKD DYISSPKWVH AKGDNIEVEM DQNLLKNRST  600
HCHNPVSIAY GRIDNIDRQQ QKSFLTIGNL QKR                              633

SEQ ID NO: 22          moltype = AA  length = 189
FEATURE                Location/Qualifiers
source                 1..189
                       mol_type = protein
                       organism = unidentified
SEQUENCE: 22
KEIIWDCYGD YEECVAESSK MDHVDVNNVE SRNIIEFCSD HTQNILPCLA TKLGLIKSMS  60
VSMFSLLLTI CEAETRNNRP AATEVQQILK HLARLYAYFC AYSNVIDLRY NKECFRYLKK  120
RCILNKPDDS CIFHHCGEKN LNLSESSPFI QQHKTTIINQ LNQSATFKNY HHRITTIFTV  180
IITFISMIQ                                                         189

SEQ ID NO: 23          moltype = AA  length = 399
FEATURE                Location/Qualifiers
source                 1..399
                       mol_type = protein
                       organism = unidentified
SEQUENCE: 23
MYNQENHDKR RNDDRFILSL PFGTNVENKS YFKPIKLSNP YSDKYLEVNK KSSDDSDQNL  60
NQALSVPQSN YDQSSESLSI DDSDLIDDST SAAQLSTSSP ISVTSASTSS FYPTLNIGNG  120
MEISAKYAKL EQSQGIKSDQ STSRVSDRYK KYTAVKRRLS ELYGIIEEKD EQLRVVRNEL  180
NGKDLEIGKL CDKIRALEYN CGRLQSMIES AGDESDQNQV KLHEIINERD GLLIRNASLS  240
RQIEFEKREW SIERERLSMD LDDVTRELEL QKMILNGESI SEIVQRWQTK VFELEGMITD  300
RDRAIRAQQV QISKLKESIA ETDRISCADS SESQTKFDFP SFTYIKRLLL QYLTRLADLH  360
FSSDEERMQL VRNMSSILHL SDEEQRQVWA NLKSKIQIS                        399

SEQ ID NO: 24          moltype = AA  length = 301
FEATURE                Location/Qualifiers
source                 1..301
                       mol_type = protein
                       organism = unidentified
SEQUENCE: 24
QCPTGSVSLL SGYRCTSSIQ CQTIIPGSYC YYGVCCTGGS DVLSKTVSYG GYCTMTVQCS  60
TTGATCISNI CQCDINSHYN GHSCVSISNF CPSNQVFIKG ECYRKVTYGF LCNYTQQCGY  120
IGAFCIGNIC SCQLDYTFDG SKCIPRSRIC PANQIAIGGQ CYPSARFGER CLYSEQCIDR  180
WYRSLSCVNG FCNIRNDDDI SKPKCRNPRA EVEYVNGTAK NCLYWPCTVG YFCEYAGGMN  240
GGRYICCGTN ANKIYGKVQL YPGTGTPLQC TEIGRCPFPD TPNCVMSYRY GYKVCCSTLN  300
C                                                                 301

SEQ ID NO: 25          moltype = AA  length = 110
FEATURE                Location/Qualifiers
source                 1..110
                       mol_type = protein
                       organism = unidentified
SEQUENCE: 25
QETSEQPGLT VEIIAEQQDA TTADQEVTTT VDTHHQHQHQ TDKVVKSRQI TGDEQTTTTT  60
TAINLNETIT NSTTDSNSTI ITTTLDLQES TTTGTTDNHH HHHHHHHHHE            110

SEQ ID NO: 26          moltype = AA  length = 185
FEATURE                Location/Qualifiers
source                 1..185
                       mol_type = protein
                       organism = unidentified
SEQUENCE: 26
MKQTTAWGNA LCVLCNCHQP QIICPPPPPA VCPRVVCPPP RPPVCPPIYC PPPVVCPPPP  60
VCPPVPFCHS QICPPCGTHT VPVAVVGCCK GCACSVRFKR DSSSVNGLML KKNLLCNNDQ  120
LMTIMEKKIG TNATEAAFAI KKEADSELKA KFSVFCAMND LIYVAHAESF CQHKKGDIIC  180
FAYKS                                                             185

SEQ ID NO: 27          moltype = AA  length = 147
FEATURE                Location/Qualifiers
source                 1..147
                       mol_type = protein
                       organism = unidentified
SEQUENCE: 27
MDCKLILPFY ILLANLEANA FHLSGYRSRS YLQGIQPYDI QPLDVQPQFI RVQTLKSQDI  60
QPYSIQSRSE DQPCEGCKIT ISCGSKNCKS KKLPYVYKPI FKLLSTRSTK KPVFTLPTQP  120
PAQWDCPCPC HVPQRCRMCS ACHESYI                                     147

SEQ ID NO: 28          moltype = AA  length = 194
FEATURE                Location/Qualifiers
```

```
source                  1..194
                        mol_type = protein
                        organism = unidentified
SEQUENCE: 28
NRIISRRLSL FIQQYCCNNI SQIYRLNDCK YSKVKMEIDK KIFIIVSKTE WCNEAIKVVF  60
GKSAEAIRNN SDAISWLASY NYTGSMDLRS KWPYDAYFDN VTRTAHGLAR IDLLCHKKRP  120
QLGPRIWKRS VQKIKQKKDR PFAVNTYGNN KGLFTITVGV LLYAAFGTCF LIANLAYLFG  180
IYIIYDASII DEVS                                                    194

SEQ ID NO: 29           moltype = AA  length = 263
FEATURE                 Location/Qualifiers
source                  1..263
                        mol_type = protein
                        organism = unidentified
SEQUENCE: 29
IGENPMDVNA IAGIIGGISN MMQNNVETID VPSSQIMGRW YQVYKAAIAF DVYRTDIFCP  60
VAYFKPNSVM GEDGFSIEEA YRVITKNGPV ETYKRDLNKV GTGQYWMYTE EYFYPRQFNI  120
ISVGPNYTNT TDGSEEEKQY QYMVVTDGNR LSLSVYARHP MIFYQKYNEE VVKFLEHAGF  180
GGKVFWNSPK PIYQGADCEW PSEKEVFARR VLKNQELAKN GGLDTATKSG SFGGSSQATD  240
VRSSITEILQ NPQLALQKLV QGH                                          263

SEQ ID NO: 30           moltype = AA  length = 242
FEATURE                 Location/Qualifiers
source                  1..242
                        mol_type = protein
                        organism = unidentified
SEQUENCE: 30
MTIIKSMLKI THVIFDLDGL LIDTEVVFSK VNQCLLSKYD KKFTPHLRGL VTGMPKKAAV  60
TYMLEHEKLS GKVDVDEYCK KYDEMAEEML PKCSLMPGVM KLVRHLKTHR IPMAICTGAT  120
KKEFEIKTRH HKELLDLISL WVLSGDDPAI KRGKPAPDPF LVTMDRFKQK PEKAENVLVF  180
EDATNGVCAA IAAGMNVVMV PDLTYMKIPE GLENKINSVL KSLEDFKPES VGLPAYDASS  240
NE                                                                 242

SEQ ID NO: 31           moltype = AA  length = 148
FEATURE                 Location/Qualifiers
source                  1..148
                        mol_type = protein
                        organism = unidentified
SEQUENCE: 31
IPQRRQQQQQ QQQQQQRDER EIPPFLEGAP PSVIDEFYNL LKTDENKTDQ QTEADVEAFI  60
NRLGGSYKVR FTQFMEEVKK ARADYERIHQ QAVARFSPAA KDADARMSAI ADSPHLTTRQ  120
KSQQIQAIMD SLSESVRREI INALSPQE                                     148

SEQ ID NO: 32           moltype = AA  length = 141
FEATURE                 Location/Qualifiers
source                  1..141
                        mol_type = protein
                        organism = unidentified
SEQUENCE: 32
DLLSEAGDFF TKHFTDIKSL FAKDEKQLQQ SVDRVKDLLA TIQDKMSMLQ PLANDMQKTT  60
LGKIGDLISQ VNSFRETMSN PKMDFTNKEN KWEELLKKIF VTEGLNKVIP LLQKLKNSAP  120
TTFATYLFTC IVPVLINTLR E                                            141

SEQ ID NO: 33           moltype = AA  length = 446
FEATURE                 Location/Qualifiers
source                  1..446
                        mol_type = protein
                        organism = unidentified
SEQUENCE: 33
MRTASQLTFM LFLVLKKKFK NIDKLFSQIS VNMSVMFANS RSSQANSGYL VEFKAGRSNL  60
QAGSTVDKRK VVADKTKGLI FIKQSSDQLM HFCWKNRETG TVVDDLIIFP GDTEFLRVKE  120
CTDGRVYMLK FKSTDEKRLF WMQDGKTDKD DENCKKINET LNNPPAPRAA ARGGADRAGA  180
SSFGTLAALG SAGADSELGA LGNLDQNQLM QLLSLMNHTN SASASEAANL LPQLPLVADT  240
PNPVASEESG TTSTQGATPS NTPANGIIAG SSSNNAVQLS QLKEIIASIT PPDGSIRKPS  300
VDFTDVLCCA DKINDVLGKY AERLIPHLPN QEPIYNNQEE LQQTLRTPQF RQAVDIFGHA  360
LQTGQLAPIL RQFGIDSNTA IAAGNGDLIA WATQFTTSEN EKEIAVKTET LPFHPGMESD  420
VEDEETNEKA VRESDKNRTD DHMDLD                                       446

SEQ ID NO: 34           moltype = AA  length = 114
FEATURE                 Location/Qualifiers
source                  1..114
                        mol_type = protein
                        organism = unidentified
SEQUENCE: 34
MLPTLYINNA VIRPVLSETK KVKVQNISSP FLIFLLLSIT KMLSLSVLLL FISMATMARP  60
PNPDEIKELH EQQLNDSKDD YDMLPDVGHI PESFKESLKK QKMLYLDMLR QQSL        114

SEQ ID NO: 35           moltype = AA  length = 298
FEATURE                 Location/Qualifiers
```

```
source                 1..298
                       mol_type = protein
                       organism = unidentified
SEQUENCE: 35
MISSRLRITI PESIVIFGIF CFFIFFCFLS FFFFFTLWSH RDTINFQTDF MTETIKFIVY  60
AVVILRMMFF DIVCFYSFLM MTIVLINTSN GLSVPAGLRP AKKVGDPREQ IVPGKEQQQQ  120
REQQQQQQQQ LQEEEQQQQQ QHDEVSNLRP TPKVPPNLSI RSRMMAALSA SPVEPNKEKN  180
SSKVETDSFS KPPIIFSKGN KKTVPGKIAP SGSSKGNARV IVAPPADLGK NNYGLNTVLQ  240
TNLVDSHGRI MKNVNSVPIK VPSSAEMKNA RTRHTARQVE SDADKVVPIK FGSTSRRR    298

SEQ ID NO: 36          moltype = AA  length = 99
FEATURE                Location/Qualifiers
source                 1..99
                       mol_type = protein
                       organism = unidentified
SEQUENCE: 36
MMRIKWIILL LLLLLPIITA EFSAPVGTNS SLTIFDKDKQ VLLRSDRLKR QCGPCGVAPS  60
PVIVCCGAAG LKEIFRSWWL HIPLLLLPMS TSWLKTMVC                        99

SEQ ID NO: 37          moltype = AA  length = 193
FEATURE                Location/Qualifiers
source                 1..193
                       mol_type = protein
                       organism = unidentified
SEQUENCE: 37
MFRLLIAIQI LRFCQANYIN DVYWKRSIIG YQHIPIILNI CYLLQTEVSN KGVVDALFLH  60
SPTYHRVEMS EETDNIESIA DKSNITVANK PNLMIYPADF QVSSNERASA SIPITITITS  120
SGDTIIKSFK HKHQSNEIFK RRVAKMAIAP VNAPEVENLA PEVENPSPST AGYESKTEEQ  180
APSESGQYGK RRK                                                    193

SEQ ID NO: 38          moltype = AA  length = 362
FEATURE                Location/Qualifiers
source                 1..362
                       mol_type = protein
                       organism = unidentified
SEQUENCE: 38
MYNLAKLLEN EHGSIEASFH VYVENFFEGL DGESWSIDQT NAQLYPIIDE PFNNTVRVGR  60
TAQFQCKVKN QQQPLIKWLK RIDDPNAIRQ ANANATLIHA NNMHLLLLEK PETSAELSDG  120
ISLNRLIIPN VRYEHSGTYL CVVTNAHGDI AYRSAYLHVI ARSDHGMLSN IYFYGGILVL  180
IVVFTLITYA VYFLRKNQAA KNSESAQDIT NTRYSFSLRP PPPNLPPPKA PALPSERQQL  240
MSDNQPCDRY AVNSAATTYY PQFATPDKKL QKIITESGGT RPTPIRRTNG GDTKYRLKDE  300
YINSPKWVHT KGDNIEVEMD QNLLKNRSSH CYNPISGAYG RTDNIDRQQQ KSFLTIGNLQ  360
KR                                                                362

SEQ ID NO: 39          moltype = AA  length = 215
FEATURE                Location/Qualifiers
source                 1..215
                       mol_type = protein
                       organism = unidentified
SEQUENCE: 39
MLKLANTEIF FIAFLVYSKE IILNCYEDYK ECVATSNKTN HVNMDNVNPQ NLIEFCFDHT  60
QNILPCLVTK LGLTKGISVS IFSLFLSTCE LEAQNNKSSS TTEMQQILRH LLRLYAYFCA  120
YSNIIDLHRN RECFRYLMKR CVLNKPDESC MFYHCGKIHF NLSKSSRKIL FTRQHDTTKI  180
VNLGNKMNQL ATFNNHQVRS AVVVTLIITF IDMIQ                            215

SEQ ID NO: 40          moltype = AA  length = 395
FEATURE                Location/Qualifiers
source                 1..395
                       mol_type = protein
                       organism = unidentified
SEQUENCE: 40
MYSQENQDDK RRNDERIALS VPYNNTNIMD RSYFKPIKLS YPYSDECLEV NKKSSDDSDQ  60
RLSQNSSTPQ SNYDQSSERL SIDDSDLIDD STSAAQLSTS SPISVTSAST SSFYPTLNIG  120
NGMEMNAKYA KIEQSEGIRS DQSSTLRISD KYKKYTAIKR RLSELCGIIE EKDKQLRVVR  180
NGLNEKDLEI GKLCDKIRAL EYNCGRLQAV IESVGDESDQ NQIKLHEIIN ERDGLLVRNA  240
SLSRQIEFEK REWSIERERL SMDLDDVTRE LELQKMILNG ENISEIVQRW QTKVFELEGM  300
IADRDRAIRA QQVRISKLKQ SLAEADRISC DDSSESQTKL DSPSFTCIKR LLLQYLTSSD  360
EERIQLLRNV STMLHLSDDE QHQVLTNLKS RIQIS                            395

SEQ ID NO: 41          moltype = AA  length = 99
FEATURE                Location/Qualifiers
SITE                   1
                       note = misc_feature - Xaa can be any naturally occurring
                        amino acid
source                 1..99
                       mol_type = protein
                       organism = unidentified
SEQUENCE: 41
XKCRDQRAEV EYVNGSAKNC LYWPCTVGYF CEYTESRNGG HYICCGTNAN NIYGKVKVYP  60
```

-continued

```
GTNKPLHCSI MNTCPFLDTP NCVMSHRYGY KVCCSTMNC                        99

SEQ ID NO: 42          moltype = AA  length = 589
FEATURE                Location/Qualifiers
source                 1..589
                       mol_type = protein
                       organism = unidentified
SEQUENCE: 42
MLMKQSDSCV DYFYDQYKGQ EYVKDDAFNT QNITDNFRKS SSDIAQLMNS QIELISQPEK  60
VNEDSAKSSH YNDDLQKSIE DDTVEATQRK KDEKLLEFLH SLIVSTIPKT IHLEGNSVNL  120
LTLTTTITPI AIITTKNTSG TANAITTRKY KKYKLNAFVN ISSDTLTELP KFLPENFNST  180
NFANVEKTEK FSNSKQVATD SIFSLKESAY LETPVIRDFS SANDSAKTDP LFTRNYVDKQ  240
IDMNTTKFNK NLKKSRLTTI STSNLTTVLS QLQTTTSIST TTSVTTTIST SITIPELTLV  300
SQSHRHLHHY HHHHHHQYEN YDHESPIIVT ALFDIGRGKW PRYTRTYEQY MNYLKHLLKL  360
ENCLVIYTDS RGAEFVRQTR NVHNTQIFEI SMHDLPLYRY REEMKGIIQR EQKDWQFSPK  420
TRYHPEANSA DYNIIVNSKP YFLYNATQNV RFRTSDRMFV WIDAGYGHGR KGIIPDHCHW  480
RPRLQRDRMT IIQLTPKHDK VSRYSITDLY RVDWVVLSGG FIAGDSHTIN RFYRFYQKLF  540
MELLDSGRID DDQTILTLML KHYTTLFNPI SSNGDWYALF RLFPCHDRQ            589

SEQ ID NO: 43          moltype = AA  length = 875
FEATURE                Location/Qualifiers
source                 1..875
                       mol_type = protein
                       organism = unidentified
SEQUENCE: 43
MKQATTWGSI CEMCPCAAKP ICPPPVICPP RICPPPVICP PQICPPCPPR ICPPPVICPP  60
QICPPCPPQI CPPCPKPQPP PPPPPPPVLP SLPPTSFKPM ITCCRTCICY IRRKRDSLND  120
YDRIHDINPV CNNDQLMMIM KKKIRTNVTE STIAIKKAAD SMLQAEFNVF CAINDLTHVA  180
HAEHFCQYKK DNSVFDSFLF RSTLKGLIEE CREGVRWWPG SLGDLDFSHI SLYRAHKYIG  240
NEEMNRSTKT KISFTRINKK WRLGHTGKKY NKVRFSRNIA KKFIGVCNII RLKKSVSRSV  300
RPFENQKSTS FNVFQLLVPK EKVEIVVDDT QAEEMNSETA QEVQLFNVRK SNADSKTDGE  360
KDTADLDVIL LTNEECSSSR QENLNKDEPE IVILDDSAPS KSDLNTSDEI ICLQDLKMVN  420
EVPTFSVTPK QKTVKELPRE TRTYGTRRGR QSRAYCEDLR KFPSIRNPVS SSSSSIHAKN  480
MPEFVDLLTQ GTLLICKKWL RRWDIVQSGV IGGNPLRICS YNVLCQQTAY KTPELYIHLT  540
KPGRAYELTW ENRWRLLTRE FSMIGADIFC LQEVQYDHYD QFFRPYFEAA GFFGKYKKRT  600
NNLLDGCAIF YKSHLQLLHY RYIEYFLNID SVLNRDNVGQ LIRLKDMRSG REFCVVNTHL  660
LFNKRRGDVK LAQLAILLAN IDQECGPESG QECPYILCGD FNFHPYSPIY NFIMNGEICF  720
TNLRRGDISG QGNAGGPFVS VNLLPEDVKI ARNCRFNYLK NRTMLLPSLN CWSHPLCFNS  780
VYQNMNGETR PMISTYHSIE AVNPDFIFYS VKSKRVQQSM LPHSVPAMNV SEREIRLIRR  840
LSLPDMNELA GTLGPWPNST TPSDHIPLIA DFVLQ                            875

SEQ ID NO: 44          moltype = AA  length = 158
FEATURE                Location/Qualifiers
source                 1..158
                       mol_type = protein
                       organism = unidentified
SEQUENCE: 44
MYCKLIISFY MLLSIANMTH LVGYRPQIYL QGIPQNIQSH DIQRLDMQQQ SLKLPDTELY  60
SIPSHDNQLQ GLQLYDMQFQ GKQSKGSEKL CSGCKISINC SGKKCVPMRT RKPIVTTPSP  120
LSTQRPVLTR PRLLADCPCP CHVSRQCRIC QPCQESFI                         158

SEQ ID NO: 45          moltype = AA  length = 230
FEATURE                Location/Qualifiers
source                 1..230
                       mol_type = protein
                       organism = unidentified
SEQUENCE: 45
MFVGMRLYLA IDVLLLLVLR IKSNRIILHR FSLFIQQHCC NNISQIHRLN DCKYSKVRMK  60
IDKKILIIVS KTEWCNEAIK VVFGKSAEAR RNRSDAISWV TPYNFTGLMN LHSKWRYDAY  120
FDNVTRTAHG LARIDLLCPK RRSHSGRRIL KRSIQENKQE KSRRSFTVNI YGSSKGIFTI  180
TVGVVIYAIF GVCFLITNMA YLSGIYTVHN TSVIPEDKKR KETSKRKEIL            230

SEQ ID NO: 46          moltype = AA  length = 279
FEATURE                Location/Qualifiers
source                 1..279
                       mol_type = protein
                       organism = unidentified
SEQUENCE: 46
MISVFLLLTV IVSYVETIGE NPMDINALAG IIGGISNMMQ NNVETIDVPS SQIMGQWYQV  60
YKAAISFDAY KTDMFCPVAY FKPNSVMGED GFSIEEAYRV ITKNGPVETF KRDLNKVGTG  120
QYWMYTEEYF YPRQFNIIGV GPNYTNATDG REKENLYEYM IVTDANRLSL SVYARHPMIF  180
YQKYNEEVVK FLEHAGFGGR VFWNSPRPIY QGTDCEWPSE KEVFARRVLK NQEAARNTGL  240
ETATKSGLFG SSLTTDAYNP IKEMLQNPQL ALQKLVQGH                         279

SEQ ID NO: 47          moltype = AA  length = 200
FEATURE                Location/Qualifiers
source                 1..200
                       mol_type = protein
                       organism = unidentified
```

```
SEQUENCE: 47
MTVIKSMLNI THVIFDLDGL LINTEIVFSQ VNQCLLSKYG KKFTSHLRGL VTGMPKKAAV  60
AHILEHERLS EKIDVDEYCK KYDEMAEEML PKCSLMPGVM KLVRHLKAHS IPMAICTGAT  120
KKEFELKTRC HKELLDLISL RVLSGDDPAV KRGKPAPDPF LVTMERFKQK PEKAENVLVF  180
EDATNGVYAA IAAEESKIVK                                             200

SEQ ID NO: 48           moltype = AA  length = 116
FEATURE                 Location/Qualifiers
source                  1..116
                        mol_type = protein
                        organism = unidentified
SEQUENCE: 48
MILEQLEVPP FLVGAPQSVI KQFYDLLKAD ETKTDAQTEA DVEAFINRLG GTYKTRFDQF  60
KQEIKQGKAA YERLHQQAVA KFSKEAREAD AKMSAIADSP SLTTQQKTQQ IQAIMD      116

SEQ ID NO: 49           moltype = AA  length = 158
FEATURE                 Location/Qualifiers
source                  1..158
                        mol_type = protein
                        organism = unidentified
SEQUENCE: 49
MLKYGILLIL ITVGAYCDLL SEAGDFFSKH FTDFKSLFAS DEKQLQQNMD RVKDLLATIQ  60
DKMTILKQLA DNSQKSTLEK ITDIISQVND FRENVFNSNV DFNQKKTKWE EVVTKIFVTD  120
GLNKVIPLLQ KAKNSAPATF ITYLLTCIVP LLINALRE                         158

SEQ ID NO: 50           moltype = AA  length = 20
FEATURE                 Location/Qualifiers
REGION                  1..20
                        note = Flexible linker
source                  1..20
                        mol_type = protein
                        organism = unidentified
SEQUENCE: 50
KGPDVPETNQ QCPSNTGMTD                                             20

SEQ ID NO: 51           moltype = AA  length = 114
FEATURE                 Location/Qualifiers
source                  1..114
                        mol_type = protein
                        organism = unidentified
SEQUENCE: 51
MARINRLNFL LCIVHANITS APNPKDSNDE LFADAESALG SEYAQFVEQS KQHKPVYFSD  60
NQNTLETIKL ESIPNPETET AYPMFICGFL GCMKKMNSVE EYLEHFKMHE KQGY       114

SEQ ID NO: 52           moltype = AA  length = 20
FEATURE                 Location/Qualifiers
source                  1..20
                        mol_type = protein
                        organism = unidentified
SEQUENCE: 52
CPSLSSYCED WDPEDFPSFV                                             20

SEQ ID NO: 53           moltype = AA  length = 29
FEATURE                 Location/Qualifiers
source                  1..29
                        mol_type = protein
                        organism = unidentified
SEQUENCE: 53
LPIDKQNEAT LLWNSLYPDD IYNECGPRF                                   29

SEQ ID NO: 54           moltype = AA  length = 25
FEATURE                 Location/Qualifiers
source                  1..25
                        mol_type = protein
                        organism = unidentified
SEQUENCE: 54
AFAPNPKDSN NELFADAESA LGSEY                                       25

SEQ ID NO: 55           moltype = AA  length = 24
FEATURE                 Location/Qualifiers
source                  1..24
                        mol_type = protein
                        organism = unidentified
SEQUENCE: 55
GCMKKMNSVE EYLEHFKMHE KQGY                                        24

SEQ ID NO: 56           moltype = AA  length = 36
FEATURE                 Location/Qualifiers
source                  1..36
```

```
                        mol_type = protein
                        organism = unidentified
SEQUENCE: 56
INKFYDMLRK WAEKYSVQAE TNRFIAEEMN YDKMQS                   36

SEQ ID NO: 57           moltype = AA  length = 35
FEATURE                 Location/Qualifiers
source                  1..35
                        mol_type = protein
                        organism = unidentified
SEQUENCE: 57
APPNRDTADD LQNADMQRQW EQEQRQREEV QKEEI                    35

SEQ ID NO: 58           moltype = AA  length = 66
FEATURE                 Location/Qualifiers
source                  1..66
                        mol_type = protein
                        organism = unidentified
SEQUENCE: 58
TDMDELEEQR KQDFKQYEMK KKAEEDHKMQ AIQTEREEYI RQMEEQRRRH NKHEPLKHPG  60
SRNQLR                                                    66

SEQ ID NO: 59           moltype = AA  length = 28
FEATURE                 Location/Qualifiers
source                  1..28
                        mol_type = protein
                        organism = unidentified
SEQUENCE: 59
DREAQEEKPD QGWEDIGDKD QYTKEELE                            28

SEQ ID NO: 60           moltype = AA  length = 30
FEATURE                 Location/Qualifiers
source                  1..30
                        mol_type = protein
                        organism = unidentified
SEQUENCE: 60
TPAPTPDPSR MIQPDQAPMQ RLDAPSDQVG                          30

SEQ ID NO: 61           moltype = AA  length = 21
FEATURE                 Location/Qualifiers
source                  1..21
                        mol_type = protein
                        organism = unidentified
SEQUENCE: 61
VSEILTVCLK EGFKKPSNLG I                                   21

SEQ ID NO: 62           moltype = AA  length = 130
FEATURE                 Location/Qualifiers
source                  1..130
                        mol_type = protein
                        organism = unidentified
SEQUENCE: 62
KNPSKMESKT GENQDRPVLL GGWEDRDPKD EEILELLPSI LMKVNEQSKD EYHLMPIKLL  60
KVSSQVVAGV KYKMDVQVAR SQCKKSSNEK VDLTKCKKLE GHPEKVMTLE VWEKPWENFM  120
RVEILGTKEV                                                130

SEQ ID NO: 63           moltype = AA  length = 181
FEATURE                 Location/Qualifiers
source                  1..181
                        mol_type = protein
                        organism = unidentified
SEQUENCE: 63
KISAENANCK KCTPMLVDSA FKEHGIVPDV VSTAPTKLVN VSYNNLTVNL GNELTPTQVK  60
NQPTKVSWDA EPGALYTLVM TDPDAPSRKN PVFREWHHWL IINISGQNVS SGTVLSDYIG  120
SGPRKGTGLH RYVFLVYKQP GSITDTQHGG NRRNFKVMDF ANKHHLGNPV AGNFFQAKHE  180
D                                                         181

SEQ ID NO: 64           moltype = AA  length = 436
FEATURE                 Location/Qualifiers
REGION                  1..436
                        note = Ov-103-RAL2-CPI2M fusion protein
source                  1..436
                        mol_type = protein
                        organism = synthetic construct
SEQUENCE: 64
DLLSEAGDFF TKHFTDIKSL FAKDEKQLQQ SVDRVKDLLA TIQDKMSMLQ PLANDMQKTT  60
LGKIGDLISQ VNSFRETMSN PKMDFTNKEN KWEELLKKIF VTEGLNKVIP LLQKLKNSAK  120
GPDVPETNQQ CPSNTGMTDP QRRQQQQQQQ QQQQRDEREI PPFLEGAPPS VIDEFYNLLK  180
TDENKTDQQT EADVEAFINR LGGSYKVRFT QFMEEVKKAR ADYERIHQQA VARFSPAAKD  240
```

-continued

```
ADARMSAIAD SPHLTTRQKS QQIQAIMDSL SESVRREIIN ALSPQEKGPD VPETNQQCPS  300
NTGMTDKNPS KMESKTGENQ DRPVLLGGWE DRDPKDEEIL ELLPSILMKV NEQSKDEYHL  360
MPIKLLKVSS QVVAGVKYKM DVQVARSQCK KSSNEKVDLT KCKKLEGHPE KVMTLEVWEK  420
PWENFMRVEI LGTKEV                                                  436

SEQ ID NO: 65          moltype = AA  length = 286
FEATURE                Location/Qualifiers
REGION                 1..286
                       note = Ov103-RAL2 fusion protein
source                 1..286
                       mol_type = protein
                       organism = synthetic construct
SEQUENCE: 65
DLLSEAGDFF TKHFTDIKSL FAKDEKQLQQ SVDRVKDLLA TIQDKMSMLQ PLANDMQKTT  60
LGKIGDLISQ VNSFRETMSN PKMDFTNKEN KWEELLKKIF VTEGLNKVIP LLQKLKNSAK  120
GPDVPETNQQ CPSNTGMTDP QRRQQQQQQQ QQQQRDEREI PPFLEGAPPS VIDEFYNLLK  180
TDENKTDQQT EADVEAFINR LGGSYKVRFT QFMEEVKKAR ADYERIHQQA VARFSPAAKD  240
ADARMSAIAD SPHLTTRQKS QQIQAIMDSL SESVRREIIN ALSPQE                 286

SEQ ID NO: 66          moltype = AA  length = 297
FEATURE                Location/Qualifiers
REGION                 1..297
                       note = OvRAL2-CPI2M fusion protein
source                 1..297
                       mol_type = protein
                       organism = synthetic construct
SEQUENCE: 66
PQRRQQQQQQ QQQQQRDERE IPPFLEGAPP SVIDEFYNLL KTDENKTDQQ TEADVEAFIN  60
RLGGSYKVRF TQFMEEVKKA RADYERIHQQ AVARFSPAAK DADARMSAIA DSPHLTTRQK  120
SQQIQAIMDS LSESVRREII NALSPQEKGP DVPETNQQCP SNTGMTDKNP SKMESKTGEN  180
QDRPVLLGGW EDRDPKDEEI LELLPSILMK VNEQSKDEYH LMPIKLLKVS SQVVAGVKYK  240
MDVQVARSQC KKSSNEKVDL TKCKKLEGHP EKVMTLEVWE KPWENFMRVE ILGTKEV     297
```